(12) United States Patent
Arber et al.

(10) Patent No.: US 12,227,766 B2
(45) Date of Patent: *Feb. 18, 2025

(54) CELL-DERIVED PARTICLES PRESENTING HETEROLOGOUS CD24 AND USE THEREOF IN THERAPY

(71) Applicant: Ichilov Tech Ltd., Tel-Aviv (IL)

(72) Inventors: Nadir Arber, Tel-Aviv (IL); Shiran Shapira, Petach-Tikva (IL)

(73) Assignee: Ichilov Tech Ltd., Tel-Avivv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/224,131

(22) Filed: Jul. 20, 2023

(65) Prior Publication Data
US 2024/0002810 A1   Jan. 4, 2024

Related U.S. Application Data

(60) Division of application No. 17/327,719, filed on May 23, 2021, now abandoned, which is a continuation-in-part of application No. PCT/IL2021/050432, filed on Apr. 15, 2021, which is a continuation-in-part of application No. 17/186,039, filed on Feb. 26, 2021, now abandoned.

(60) Provisional application No. 63/010,830, filed on Apr. 16, 2020.

(51) Int. Cl.
| | |
|---|---|
| C07K 14/705 | (2006.01) |
| C07K 14/71 | (2006.01) |
| C12N 5/00 | (2006.01) |
| C12N 5/071 | (2010.01) |
| C12N 5/077 | (2010.01) |

(52) U.S. Cl.
CPC ............ *C12N 5/0686* (2013.01); *C07K 14/71* (2013.01); *C12N 5/0656* (2013.01); *C12N 2500/90* (2013.01); *C12N 2501/33* (2013.01); *C12N 2501/599* (2013.01); *C12N 2501/998* (2013.01)

(58) Field of Classification Search
CPC ................................ C07K 14/705; C12N 5/00
See application file for complete search history.

(56) References Cited

U.S. PATENT DOCUMENTS

| | | | |
|---|---|---|---|
| 4,844,129 A | | 7/1989 | Bridgeford et al. |
| 8,568,994 B2 | | 10/2013 | Altevogt et al. |
| 10,639,350 B2 | | 5/2020 | Arber |
| 2006/0292178 A1 | | 12/2006 | Hong et al. |
| 2008/0038230 A1 | | 2/2008 | Lindeman |
| 2014/0314675 A1 | * | 10/2014 | Yamazaki et al. ... G01N 33/574 424/9.2 |
| 2018/0221445 A1 | * | 8/2018 | Arber et al. ........ A61K 38/1774 |
| 2019/0085284 A1 | * | 3/2019 | Villiger et al. ...... C12N 5/0043 |
| 2020/0399591 A1 | | 12/2020 | Hean et al. |
| 2021/0322483 A1 | | 10/2021 | Arber et al. |
| 2021/0324339 A1 | | 10/2021 | Arber et al. |
| 2023/0233618 A1 | | 7/2023 | Arber et al. |

FOREIGN PATENT DOCUMENTS

| | | | |
|---|---|---|---|
| WO | WO 2005/070120 | 8/2005 | |
| WO | WO 2018/217659 | 11/2018 | |
| WO | WO2018217659 A1 * | 11/2018 | ............. A61K 38/17 |
| WO | WO 2020/257720 | 12/2020 | |
| WO | WO 2021/210002 | 10/2021 | |

OTHER PUBLICATIONS

Teijaro et al. (2017) "Cytokine storms in infectious diseases" In Seminars in immunopathology, vol. 39, No. 5, pp. 501-503), Berlin/Heidelberg: Springer Berlin Heidelberg. (Year: 2017).*
Channappanavar et al. (2017) "Pathogenic human coronavirus infections: causes and consequences of cytokine storm and immunopathology" In Seminars in immunopathology, vol. 39, pp. 529-539, Springer Berlin Heidelberg. (Year: 2017).*
Runz et al. "Malignant ascites-derived exosomes of ovarian carcinoma patients contain CD24 and EpCAM", Gynecologic Oncology 107 (2007) 563-571. (Year: 2007).*
Advisory Action Dated Mar. 18, 2022 from US Patent and Trademark Office Re. U.S. Appl. No. 17/186,039. (3 pages).
European Search Report and the European Search Opinion Dated Aug. 16, 2021 From the European Patent Office Re. Application No. 21168720.7. (11 Pages).
Final Official Action Dated Jan. 20, 2023 from the US Patent and Trademark Office Re. U.S. Appl. No. 17/327,719. (102 pages).
Final Official Action Dated Feb. 22, 2022 from US Patent and Trademark Office Re. U.S. Appl. No. 17/327,719. (19 pages).
Final Official Action Dated Nov. 29, 2021 from US Patent and Trademark Office Re. U.S. Appl. No. 17/186,039. (22 pages).
International Search Report and the Written Opinion Dated Aug. 4, 2021 From the International Searching Authority Re. Application No. PCT/IL2021/050432 (14 Pages).
Interview Summary Dated Feb. 15, 2022 from US Patent and Trademark Office Re. U.S. Appl. No. 17/186,039. (2 pages).
Official Action Dated Aug. 2, 2021 from the US Patent and Trademark Office Re. U.S. Appl. No. 17/186,039. (26 pages).
Official Action Dated Jul. 19, 2022 from US Patent and Trademark Office Re. U.S. Appl. No. 17/327,719. (26 pages).
Official Action Dated May 25, 2023 from the US Patent and Trademark Office Re. U.S. Appl. No. 17/186,039. (99 pages).
Official Action Dated Oct. 25, 2021 from the US Patent and Trademark Office Re. U.S. Appl. No. 17/327,719. (31 pages).
Official Action Dated Jun. 30, 2022 from US Patent and Trademark Office Re. U.S. Appl. No. 17/186,039. (21 pages).

(Continued)

*Primary Examiner* — Teresa E Knight
*Assistant Examiner* — James Joseph Graber

(57) ABSTRACT

A method of producing cell derived particles is disclosed. The method comprising isolating cell-derived particles from a biological sample comprising cells modified to present CD24 so as to obtain a preparation of the cell-derived particles substantially devoid of intact cells. Cell derived particles, a culture medium and a cell culture are also disclosed.

14 Claims, 33 Drawing Sheets

Specification includes a Sequence Listing.

(56) References Cited

OTHER PUBLICATIONS

Restriction Official Action Dated May 7, 2021 From the US Patent and Trademark Office Re. U.S. Appl. No. 17/186,039. (13 Pages).
Restriction Official Action Dated Jul. 29, 2021 from the US Patent and Trademark Office Re. U.S. Appl. No. 17/327,719. (8 pages).
Barkal et al. "CD24 Signalling Through Macrophage Siglec-10 Is A Target for Cancer Immunotherapy", Nature, 572(7769): 392-396, Published Online Jul. 31, 2019.
Bradley "CD24—A Novel 'Don't Eat Me' Signal", Nature Reviews Cancer, 19(10): 541, Oct. 2019.
Chen et al. "Amelioration of Sepsis by Inhibiting Sialidase-Mediated Disruption of the CD24-SiglecG Interaction", Nature Biotechnology, 29(5): 428-435, Published Online May 6, 2011.
Chen et al. "CD24 and Siglec-10 Selectively Repress Tissue Damage-Induced Immune Responses", Science, 323: 1722-1725, Published Online Mar. 5, 2009.
Chen et al. "Siglec-G/10 in Self-Nonself Discrimination of Innate and Adaptive Immunity", Glycobiology, 24(9): 800-806, Advance Access Publication Jul. 4, 2014.
ClinicalTrials "CD24Fc as A Non-Antiviral Immunomodulator in COVID-19 Treatment (SAC-COVID)", ClinicalTrials.gov, ID: NCT04317040, Mar. 20, 2020.
Cobelli et al. "Exosomes: Biology, Therapeutic Potential, and Emerging Role in Musculoskeletal Repair and Regeneration", Annals of the New York Academy of Sciences, 1410(1): 57-67, Published Online Nov. 10, 2917.
Dinh et al. "Inhalation of Lung Spheroid Cell Secretome and Exosomes Promotes Lung Repair in Pulmonary Fibrosis", Nature Communications, 11(1): 1064-1-1064-14, Published Online Feb. 28, 2020.
Fang ct al. "CD24: From A to Z", Cellular & Molecular Immunology, 7(2): 100-103, Published Online Feb. 15, 2010.
Fang et al. "Efficient and Inexpensive Transient Expression of Multispecific Multivalent Antibodies in Expi293 Cells", Biological Procedures Online, 19(11): 1-9, 2017.
Garcia-Contreras et al. "Exosomes as Biomarkers and Therapeutic Tools for Type 1 Diabetes Mellitus", European Review for Medical and Pharmacological Sciences, 21(12): 2940-2956, Jun. 2017.
Giebel et al. "Clinical Potential of Mesenchymal Stem/Stromal Cell-Derived Extracellular Vesicles", Stem Cell Investigation, 4: 84-1-84-12, Oct. 24, 2017.
Kamerkar et al. "Exosome-Mediated Genetic Reprogramming of Tumor-Associated Macrophages by ExoASO-STAT6 Leds to Potent Monotherapy Antitumor Activity", Science Advances, 8(7): 1-17, Feb. 18, 2023.
Kay et al. "CD24, a Signal Transducer Modulating B Cell Activation Responses, is a Very Short Peptide with a Glycosyl Phosphatidylinositol Membrane Anchor", The Journal of Immunology, 147(4): 1412-1416, Aug. 15, 1991.
Keller et al. "CD24 is a marker of exosomes decreted into urine and amniotic fluid", Kidney International, (2007) 72: 1095-1102, 2007.
Li et al. "CD24 Expression on T Cells Is Required for Optimal T Cell Proliferation in Lymphopenic Host", The Journal of Experimental Medicine, 200(8): 1083-1089, Oct. 18, 2004.
Liu et al. "CD24-Siglec G/10 Discrimates Danger- From Pathogen-Associated Molecular Patterns", Trends in Immunology, 30(12): 557-561, Available Online Sep. 26, 2008.
Liu et al. "Sialoside-Based Pattern Recognitions Discriminating Infections From Tissue Injuries", Current Opinion in Immunology, 23(1): 41-45, Available Online Jan. 3, 2011.
OncoImmune "CD24Fc as A Non-Antiviral Immunomodulator in COVID-19 Treatment (SAC-COVID)", ClinicalTrials.gov, OncoImmune Inc., ClinicalTrials. gov Identifier: NCT04317040, 9 P., Mar. 20, 2020.
OncoImmune "CD24Fc for the Prevention of Acute GVHD Following Myeloablative HSCT (CATHY)", ClinicalTrials.gov, OncoImmune Inc., ClinicalTrials. gov Identifier: NCT04095858, 10 P., Sep. 19, 2019.
OncoImmunc "Phase II Trial of CD24Fc for the Prevention of Acute AVHD Following Myeloablative Allogeneic HSCT", ClinicalTrials.gov, OncoImmune Inc., ClinicalTrials.gov Identifier: NCT02663622, 10 P., Jan. 26, 2016.
OncoImmune "Safety Study of CD24Fc When Administered Intravenously in Healthy Adult Subjects", ClnicalTrials.gov, OncoImmune Inc., ClinicalTrials.gov Identifier: NCT02650895, 7 P., Jan. 8, 2016.
Parada et al. "Camouflage Strategies for Therapeutic Exosomes Evasion from Phagocytosis", Journal of Advanced Research, 31: 61-74, Published Online Jan. 8, 2021.
Runz et al. "Malignant Ascites-Derived Exosomes of Ovarian Carcinoma Patients Contain CD24 and EpCAM", Gynecologic Oncology, XP022405901, 107(3): 563-571, Available Online Sep. 27, 2007.
Sagiv et al. "CD24 Is A New Oncogene, Early at the Multistep Process of Colorectal Cancer Carcinogenesis", Gastroenterology, 131(2): 630-639, Aug. 2006.
Sagiv et al. "CD24 Plays An Important Role in the Carcinogenesis Process of the Pancreas", Biomedicine & Pharmacotherapy, 60(6): 280-284, Available Online Jun. 23, 2006.
Sagiv et al. "The Novel Oncogene CD24 and Its Arising Role in the Carcinogenesis of the GI Tract: From Research to Therapy", Expert Review of Gastroenterology & Hepatology, 2(1): 125-133, Feb. 2008.
Shapira et al. "The CD24 Protein Inducible Expression System Is An Ideal Tool to Excplore the Potential of CD24 as An Oncogene and A Target for Immunotherapy In Vitro and In Vivo", The Journal of Biological Chemistry, 186(47): 40548-40555, Published Online Oct. 5, 2011.
Stickney et al. "Development of exosome surface display technology in living human cells", Biochemical and Biophysical Research Communications, 472 (2016): 53-59, 2016.
Sun et al. "Applications of Stem Cell-Derived Exosomes in Tissue Engineering and Neurological Diseases", Reviews in the Neurosciences, 29(5): 531-546, Jul. 26, 2018.
Tian et al. "CD24 and Fc Fusion Protein Protects SIVmac239-Infected Chinese Rhesus Macaque Against Progression to AIDS", Antiviral Research, 157: 9-17, Available Online Jul. 3, 2018.
Tian ct al. "CD24Fc Protects Against Viral Pneumonia in Simian Immunodeficiency Virus-Infected Chinese Rhesus Monkeys", Cellular & Molecular Immunology, 17(8): 887-888, Published Online May 7, 2020.
Toubai et al. "Siglec-G Represses DAMP-Mediated Effects on T Cells", JCI Insight, 2(14): e92293-1-e92293-15, Published Online Jul. 20, 2017.
Official Action Dated Jul. 10, 2024 from the US Patent and Trademark Office Re. U.S. Appl. No. 18/114,317. (43 pages).
Ghalib "SARS-COV-2(COVID-19)", Journal of the Faculty of Medicine Baghdad, 61(3,4): 91-93, Apr. 15, 2020.
Khourssaji et al. "A biological profile for diagnosis and outcome of COVID-19 patients", Clinical Chemistry and Laboratory Medicine (CCIM), 58(12): 2141-2150, Oct. 15, 2020.
Soler et al. "A primer on viral-associated olfactory loss in the era of COVID-19", International Forum of Allergy & Rhinology 10(7): 814-820, Jul. 7, 2020.
Restriction Official Action Dated Dec. 26, 2023 from the US Patent and Trademark Office Re. U.S. Appl. No. 18/114,317. (7 pages).

\* cited by examiner

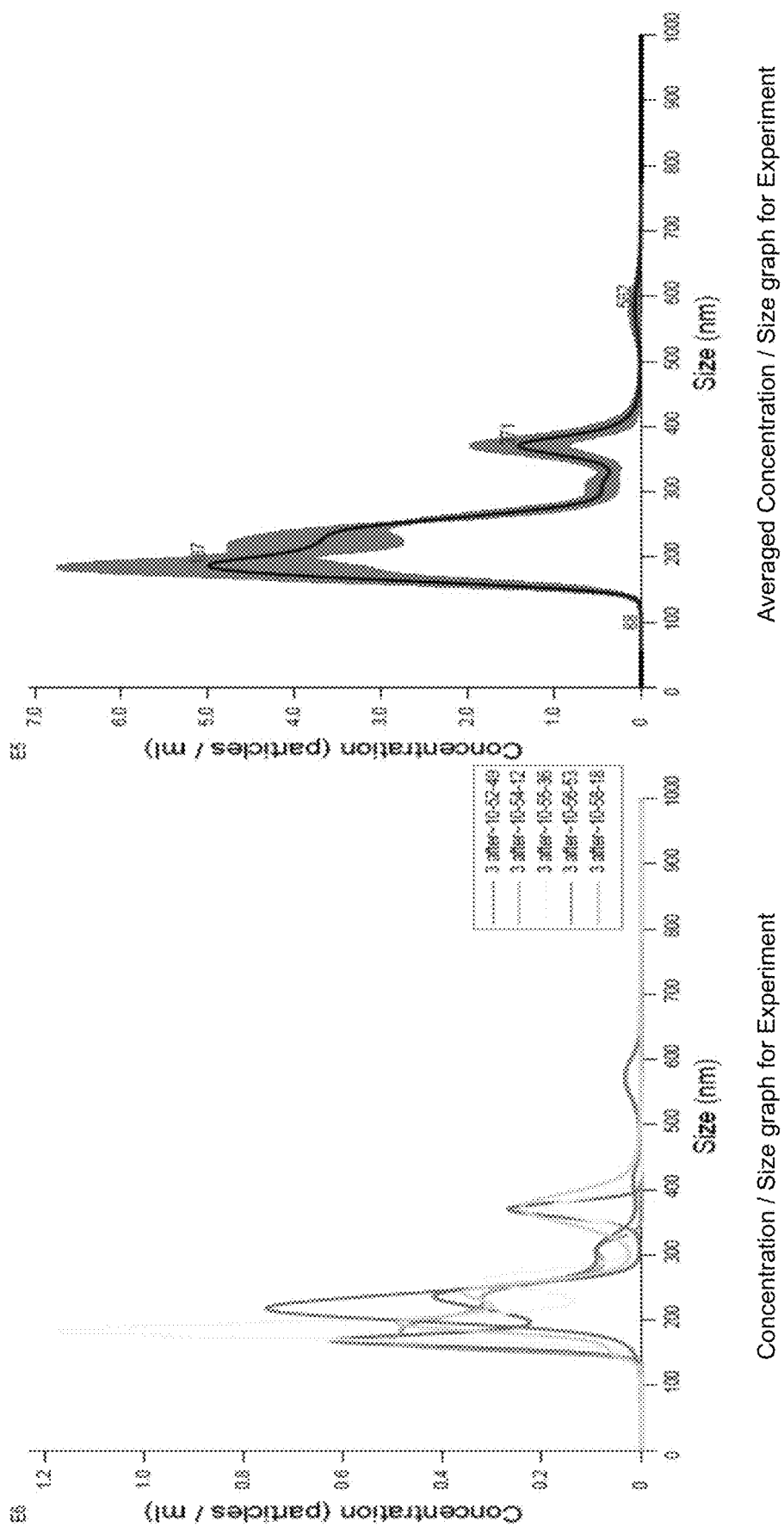

5% PEG

8% PEG

10% PEG

12% PEG

ExoQuick

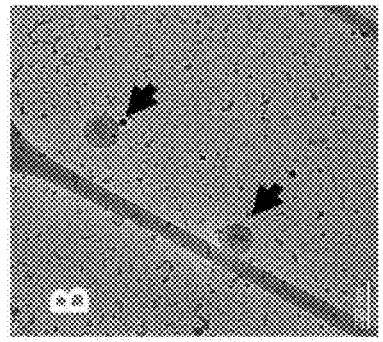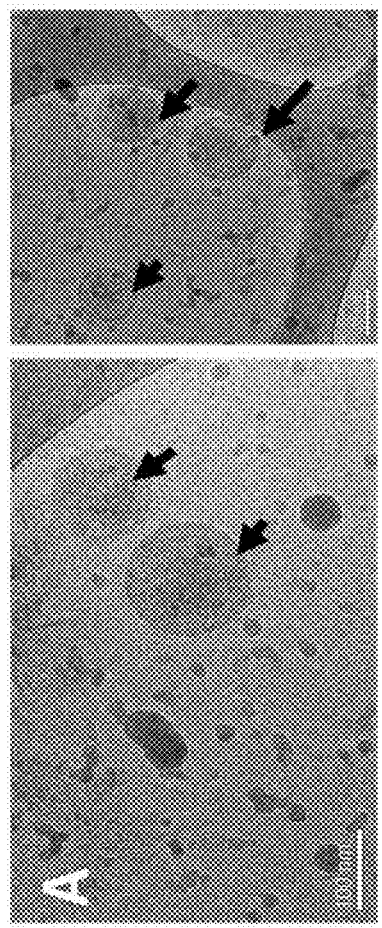
FIG. 7B
FIG. 7A

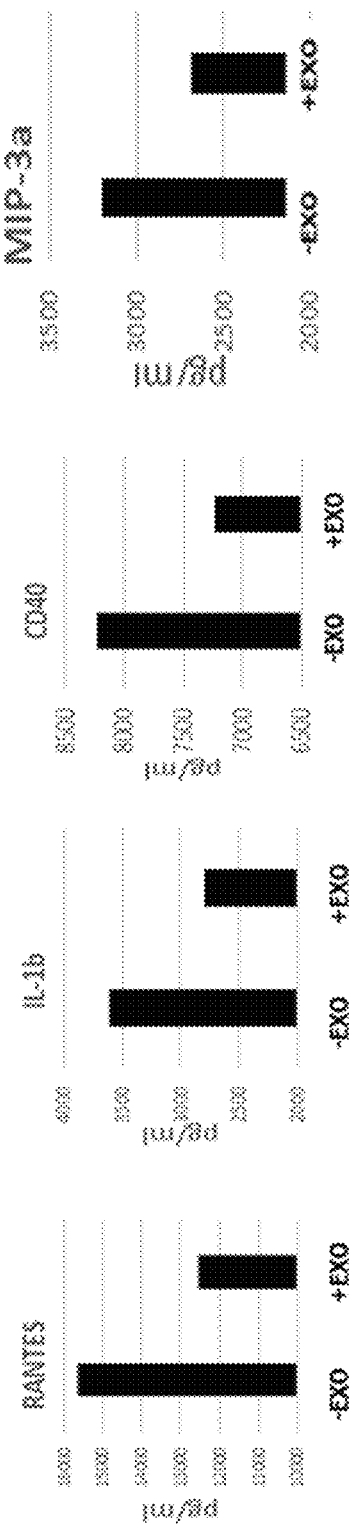
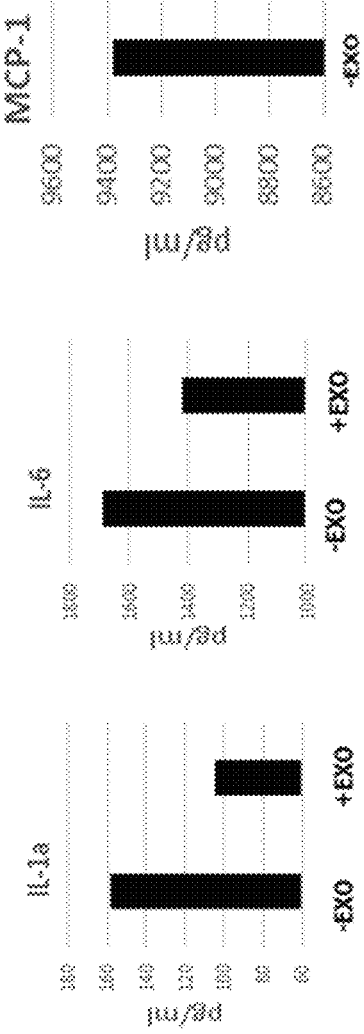

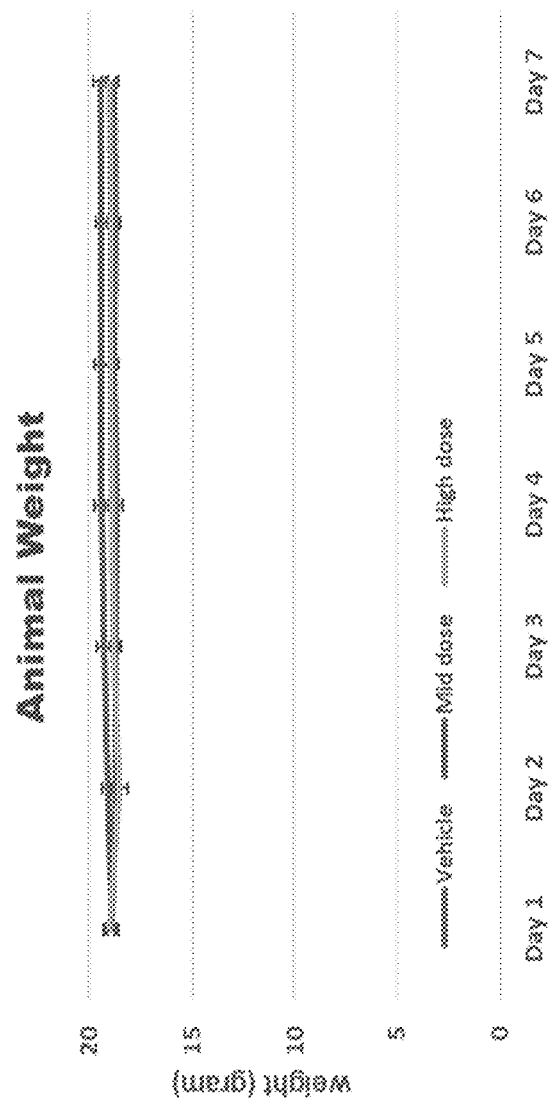

FIG. 13

| group | recovery | mouse | Leukocytes | Urobilinogen | Bilirubin (mg/dL) | Blood | Nitrite | pH | Specific Gravity | Protein (mg/dL) | Glucose | Keytone |
|---|---|---|---|---|---|---|---|---|---|---|---|---|
| Vehicle | | 8951 | negative | Normal | 0.5 | negative | negative | 5 | 1.03 | 30 | negative | negative |
| | | 8952 | negative | Normal | 0.5 | negative | negative | 6 | 1.03 | 30 | negative | negative |
| | | 8953 | negative | Normal | 0.5 | negative | negative | 6 | 1.03 | 30 | negative | negative |
| | | 8954 | negative | Normal | 0.5 | negative | negative | 5 | 1.03 | 30 | negative | negative |
| | | 8955 | negative | Normal | 0.5 | negative | negative | 6 | 1.03 | 30 | negative | negative |
| Mid dose | | 8959 | negative | Normal | 0.5 | negative | negative | 6 | 1.03 | 30 | negative | negative |
| | | 8960 | negative | Normal | 0.5 | negative | negative | 5 | 1.03 | 30 | negative | negative |
| | | 8961 | negative | Normal | 0.5 | negative | negative | 6 | 1.03 | 30 | negative | negative |
| | | 8962 | negative | Normal | 0.5 | negative | negative | 6 | 1.03 | 30 | negative | negative |
| | | 8963 | negative | Normal | 0.5 | negative | negative | 6 | 1.03 | 30 | negative | negative |
| | | 8964 | negative | Normal | 0.5 | negative | negative | 6 | 1.03 | 30 | negative | negative |
| | | 8965 | negative | Normal | 0.5 | negative | negative | 6 | 1.03 | 30 | negative | negative |
| | | 8966 | negative | Normal | 0.5 | negative | negative | 5 | 1.03 | 30 | negative | negative |
| High dose | | 8970 | negative | Normal | 0.5 | negative | negative | 5 | 1.03 | 30 | negative | negative |
| | | 8971 | negative | Normal | 0.5 | negative | negative | 6 | 1.03 | 30 | negative | negative |
| | | 8972 | negative | Normal | 0.5 | negative | negative | 6 | 1.03 | 30 | negative | negative |
| | | 8973 | negative | Normal | 0.5 | negative | negative | 5 | 1.03 | 30 | negative | negative |
| | | 8974 | negative | Normal | 0.5 | negative | negative | 5 | 1.03 | 30 | negative | negative |
| | | 8975 | negative | Normal | 0.5 | negative | negative | 6 | 1.03 | 30 | negative | negative |
| | | 8976 | negative | Normal | 0.5 | negative | negative | 6 | 1.03 | 30 | negative | negative |
| | | 8977 | negative | Normal | 0.5 | negative | negative | 6 | 1.03 | 30 | negative | negative |

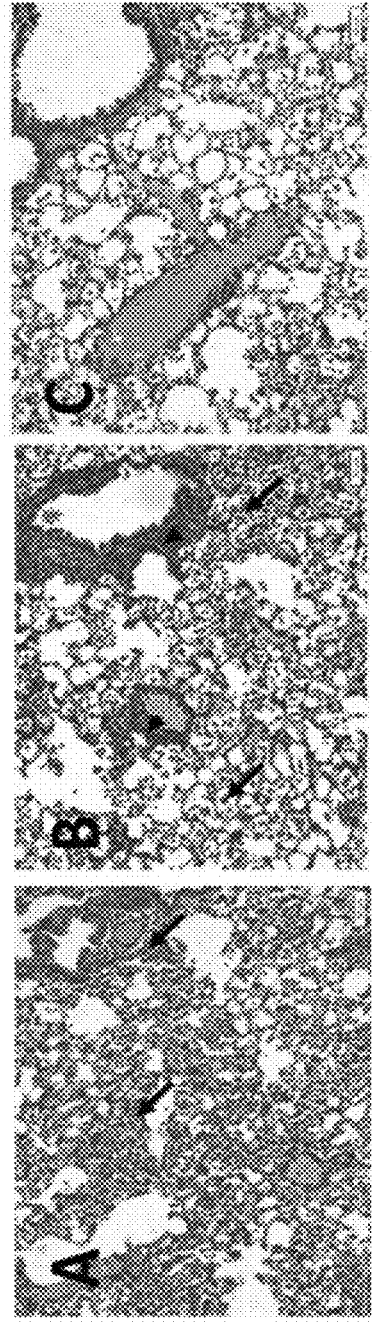

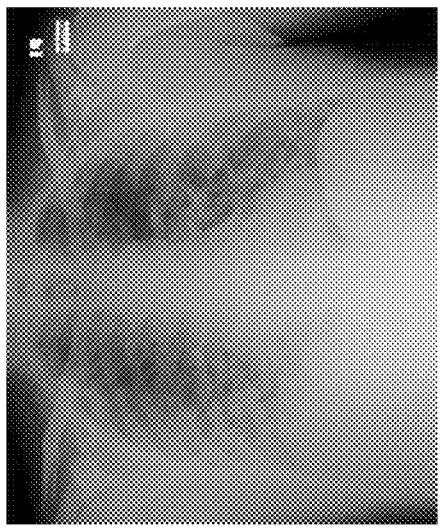
FIG. 20A Before treatment
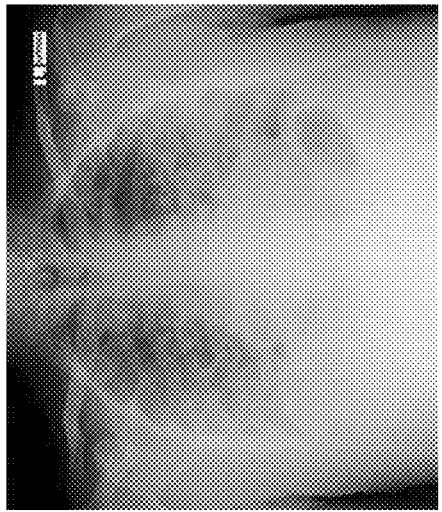
FIG. 20B After 3 days

CELL-DERIVED PARTICLES PRESENTING HETEROLOGOUS CD24 AND USE THEREOF IN THERAPY

RELATED APPLICATIONS

This application is a division of U.S. patent application Ser. No. 17/327,719 filed on May 23, 2021, which is a Continuation-in-Part (CIP) of PCT Patent Application No. PCT/IL2021/050432 having International Filing Date of Apr. 15, 2021, which claims the benefit of priority under 35 USC § 119(e) of U.S. Provisional Patent Application No. 63/010,830 filed on Apr. 16, 2020.

PCT Patent Application No. PCT/IL2021/050432 is also a Continuation-in-Part (CIP) of U.S. patent application Ser. No. 17/186,039 filed on Feb. 26, 2021, which claims the benefit of priority under 35 USC § 119(e) of U.S. Provisional Patent Application No. 63/010,830 filed on Apr. 16, 2020.

The contents of the above applications are all incorporated by reference as if fully set forth herein in their entirety.

SEQUENCE LISTING STATEMENT

The ASCII file, entitled 97294SequenceListing.xml, created on Jul. 20, 2023, comprising 17,056,586 bytes, submitted concurrently with the filing of this application is incorporated herein by reference.

FIELD AND BACKGROUND OF THE INVENTION

The present invention, in some embodiments thereof, relates to a composition comprising cell-derived particles presenting heterologous CD24 and uses of the composition is the treatment of a cytokine storm syndrome, coronavirus infection and tissue damage conditions associated with inflammation.

Inflammation is the body's response to insults, which include infection, trauma, and hypersensitivity. Clinically, pulmonary inflammation can be an acute inflammation which is typically seen in pneumonia and acute respiratory distress syndrome (ARDS), or chronic inflammation which is typically represented by asthma and chronic obstructive pulmonary disease (COPD). Specifically, ARDS is a type of respiratory failure which is characterized by rapid onset of widespread inflammation in the lungs and usually occurs when fluid builds up in the air sacs (alveoli) in the lungs, keeping the lungs from filling with enough air. As such, the main symptoms of ARDS include severe shortness of breath, labored and very rapid breathing, low blood pressure, confusion, and tiredness. ARDS may be caused by any of the following causes: sepsis, inhalation of harmful substances, severe pneumonia, head/chest or other major injury, pancreatitis, massive blood transfusions, large burns, or severe infectious diseases, such as severe COVID-19. The mortality rate for ARDS is estimated at 20-40%, depending on the age of the patient and the severity of the syndrome. Of the people who survive ARDS, some experience lasting damage to their lungs.

The SARS coronavirus 2 (SARS-CoV-2) is a newly discovered member of the family of coronaviruses. It is a respiratory virus that causes a disease known as COVID-19 which is typically characterized by fever, fatigue, dry cough, shortness of breath and ARDS. Some evidence suggests involvement of the digestive system (e.g., diarrhea) and some sensory loss, including loss of taste and/or smell. Nasal congestion, rhinitis, sore throat, and muscle pain were also reported. First discovered in December of 2019 in China, it has spread globally extremely rapidly evolving into a global pandemic. As of April 2020, there are close to 2 million confirmed COVID-19 cases worldwide, with close to 200,000 deaths.

During the course of COVID-19 disease, the virus is initially detected in airway specimens 1-2 days before the onset of symptoms and can last up to 8 days in mild cases and for longer periods in more severe cases, peaking in the second week after infection. Most patients have a high probability of a full recovery while about 5-7% develop severe illness, especially older patients (≥60 years of age) or those with background diseases (such as diabetes mellitus). Many of the severe cases of COVID-19 are associated with virus-induced ARDS, for which no effective treatment is available, and which are associated with high mortality rates.

The deterioration typically occurs around days 6-8 from the onset of the disease and can develop quickly, e.g. over a period of one day. It is usually characterized by pneumonia, with typical radiological findings, accompanied by a "cytokine storm". It has been shown that severe COVID-19 cases are characterized by markedly high levels of IL-2R, IL-6, IL-10, and TNF-α. The excessive production of pro-inflammatory cytokines leads to ARDS aggravation and widespread tissue damage resulting in multi-organ failure and death. Thus, early diagnosis and initiation of therapy to prevent progression from the viral phase of the disease to the cytokine stage by prevention of the "cytokine storm" may be very significant in the ability to prevent deterioration of the respiratory tract and development of ARDS in which the prognosis can be disastrous.

CD24 is a small, heavily glycosylated Glycosylphosphatidylinositol (GPI)-anchored protein. CD24 is a well-known oncogene playing a key role in the vast majority of human cancers. CD24 also plays an important role in controlling homeostatic proliferation of T cells and can negatively regulate inflammation. It was previously shown that CD24 is a dominant innate immune checkpoint, "do not eat me signal".

Pattern recognition receptors, such as Toll or Toll-like receptors (TLRs), recognize pathogens or components of injured cells Damage-associated molecular patterns (DAMPs) and trigger activation of the innate immune system. Another distinct class of pattern recognition receptors are the Siglecs, which exert the opposite effect and down-regulate cellular responses. CD24 was found to interact with both DAMPs and Siglec-10. CD24's link to DAMPs prevents them from binding to the TLRs, therefore inhibiting the NFκB pathway. At the same time, the CD24-Siglec-10 axis negatively regulates the activity of NFκB through Immunoreceptor Tyrosine-based Inhibition Motif domains associated with SHP-1 (FIG. 1).

In preclinical studies, a recombinant fusion protein composed of the extracellular domain of CD24 linked to a human immunoglobulin G1 (IgG1) Fc domain (i.e. CD24Fc), had been proven as potential immune checkpoint inhibitor with anti-inflammatory activity [Bradley, *Nature Reviews Cancer* (2019) 19: 541; Tian R et al., *Cellular & Molecular Immunology* (2020) 17: 887-8881. CD24Fc has been tested in a Phase I safety study in healthy subjects (www(dot)clinicaltrials(dot)gov/ct2/show/NCT02650895), as well as in a Phase II trial for the prophylactic treatment of GVHD in leukemia patients undergoing hematopoietic stem cell transplantation (www(dot)clinicaltrials(dot)gov/ct2/show/NCT2663622), with promising efficacy, tolerability and no toxicity. There was no infection-related morbidity/mortality related to CD24Fc treatment. The treatment is being tested in Phase III clinical trials for the treatment of GVHD (www(dot)clinicaltrials(dot)gov/ct2/show/NCT4095858) and of COVID-19 (www(dot)clinicaltrials (dot)gov/ct2/show/NCT4317040).

Exosomes are vesicles released by cells when multivesicular endosomes fuse with the cellular plasma membranes. Exosomes have increased stability and, hence, can play a role in enhancing bioavailability of bioactive compounds. Some studies have shown that exosomes can resist the enzymes in digestive and other biological fluids, so they are protected from degradation until they reach their target. Exosomes are in ongoing clinical research for therapeutic agents against cancer, cardiovascular, diabetic, graft-versus-host, neurological, and orthopedic diseases [Garcia-Contreras, *Eur Rev Med Pharmacol Sci* (2017) 21(12):2940-2956; Giebel et al., *Stem Cell Investig* (2017) 4:84; Cobelli et al., *Ann NY Acad Sci* (2017) 1410(1):57-67; Sun et al., *Rev Neurosci* (2018) 29(5):531-546].

In a recent trial, it was shown that lung spheroid cell-derived exosomes delivered via inhalation (using a nebulizer), can help repair lung injuries and fibrosis in mice and rats. Histological analysis of the heart, kidneys, liver, and spleens of treated animals did not reveal any apparent damage or toxicity. Animal survival and adverse effects were also monitored during these in-vivo studies [Phuong-Uyen C. Dinh, et al., *Nat Comm* (2020) 11, Article no: 1064].

Additional background art includes:

PCT publication no. WO/2020/257720 discloses exosomes for disease treatment, such as for the treatment of viral disease e.g. Coronavirus infection. According to their teachings placenta-derived exosomes contain active biological material including cytokines, mRNA, miRNA, and proteins (e.g. CD24) which may be expressed on their surface. According to WO/2020/257720 such exosomes may be used for the treatment of lung injury diseases such as acute respiratory distress syndrome (ARDS) and/or ventilator induced injury of lung infection patients (e.g. COVID-19 patients).

US Patent Application No. 2020/0399591 discloses protein engineered extracellular vesicles (EVs) and the use of same for treatment of lysosomal storage disorders (LSD). According to their teachings, EVs are obtainable from various cells such as from mesenchymal stromal cells (MSCs), amnion epithelial (AE) cells or placenta-derived cells, and are engineered for expression of lysosomal proteins. The disclosed EVs are selected to be positive for various protein markers e.g. CD24.

SUMMARY OF THE INVENTION

According to an aspect of some embodiments of the present invention there is provided a composition comprising cell-derived particles presenting heterologous CD24, wherein the cell is a non-cancerous cell and wherein the composition is substantially devoid of intact cells.

According to an aspect of some embodiments of the present invention there is provided a method of treating or preventing a cytokine storm syndrome in a subject in need thereof, the method comprising administering to the subject a therapeutically effective amount of the composition of some embodiments of the invention, thereby treating or preventing the cytokine storm syndrome in the subject.

According to an aspect of some embodiments of the present invention there is provided a method of treating or preventing a tissue injury associated with inflammation in a subject in need thereof, the method comprising administering to the subject a therapeutically effective amount of the composition of some embodiments of the invention, thereby treating or preventing the tissue injury associated with the inflammation in the subject.

According to an aspect of some embodiments of the present invention there is provided a method of treating or preventing a coronavirus infection in a subject in need thereof, the method comprising administering to the subject a therapeutically effective amount of the composition of some embodiments of the invention, thereby treating the coronavirus infection in the subject.

According to an aspect of some embodiments of the present invention there is provided a method of producing cell-derived particles, the method comprising:

(a) modifying cells to present CD24;
(b) isolating cell-derived particles from a biological sample comprising the cells modified to present CD24 so as to obtain a preparation of the cell-derived particles substantially devoid of intact cells.

According to one embodiment, the method further comprises culturing the cells modified to present CD24 following step (a) and prior to step (b).

According to one embodiment, the method further comprises culturing the cells modified to present CD24 prior to isolating cell-derived particles from a biological sample.

According to one embodiment, the method further comprises modifying cells to present CD24 to obtain the cells modified to present CD24 prior to isolating cell-derived particles from a biological sample.

According to an aspect of some embodiments of the present invention there is provided a method of producing cell derived particles, the method comprising isolating cell-derived particles from a biological sample comprising cells modified to present CD24 so as to obtain a preparation of the cell-derived particles substantially devoid of intact cells.

According to an aspect of some embodiments of the present invention there is provided cell-derived particles presenting heterologous CD24 produced according to the method of some embodiments of the invention.

According to an aspect of some embodiments of the present invention there is provided a culture medium comprising Expi293™ medium, insulin and albumin.

According to an aspect of some embodiments of the present invention there is provided a cell culture comprising cells and the medium of some embodiments of the invention.

According to some embodiments of the invention, the cells are cultured in a serum-free culture medium.

According to some embodiments of the invention, the culture medium comprises Expi293™ medium.

According to some embodiments of the invention, the cells are cultured in a suspension culture.

According to some embodiments of the invention, the suspension culture is in the absence of insulin and albumin.

According to some embodiments of the invention, the cells are cultured in a 2D culture.

According to some embodiments of the invention, the 2D culture comprises insulin and albumin.

According to some embodiments of the invention, the preparation of the cell-derived particles comprises about $1 \times 10^{10}$-$1 \times 10^{15}$ cell derived particles per liter.

According to some embodiments of the invention, when the cells are cultured in a suspension culture, the preparation of the cell-derived particles comprises at least about 3 times more cell derived particles as compared to cells cultured in a 2D culture.

According to some embodiments of the invention, there is provided the composition of some embodiments of the invention for use in treating or preventing a cytokine storm syndrome in a subject in need thereof.

According to some embodiments of the invention, there is provided the composition of some embodiments of the invention for use in treating or preventing tissue injury associated with inflammation in a subject in need thereof.

According to some embodiments of the invention, there is provided the composition of some embodiments of the invention for use in treating or preventing a coronavirus infection in a subject in need thereof.

According to some embodiments of the invention, the modifying comprises genetically modifying to present CD24.

According to some embodiments of the invention, the modifying comprises chemically modifying to present CD24.

According to some embodiments of the invention, the CD24 is as set forth in SEQ ID NO: 9 or encodable by SEQ ID NO: 8.

According to some embodiments of the invention, the cytokine storm syndrome is lung-associated.

According to some embodiments of the invention, the cytokine storm syndrome is associated with an infectious disease.

According to some embodiments of the invention, the infectious disease is virus induced.

According to some embodiments of the invention, the virus is selected from the group consisting of a coronavirus, influenza virus, Epstein-Barr virus, cytomegalovirus, flavivirus, variola and hantavirus.

According to some embodiments of the invention, the virus is a coronavirus.

According to some embodiments of the invention, the coronavirus is selected from the group consisting of a severe acute respiratory syndrome coronavirus 2 (SARS-CoV-2), a Middle East respiratory syndrome coronavirus (MERS-CoV) and a severe acute respiratory syndrome coronavirus (SARS-CoV).

According to some embodiments of the invention, the infectious disease is caused by a severe acute respiratory syndrome coronavirus 2 (SARS-CoV-2).

According to some embodiments of the invention, the infectious disease is COVID-19.

According to some embodiments of the invention, the virus is an influenza virus.

According to some embodiments of the invention, the influenza virus is H1N1 (Spanish influenza) or H5N1 (Avian flu).

According to some embodiments of the invention, the infectious disease is bacteria induced.

According to some embodiments of the invention, the bacteria is *streptococcus* group A.

According to some embodiments of the invention, the cytokine storm syndrome is associated with a medical condition selected from the group consisting of COVID-19, Acute respiratory distress syndrome (ARDS), graft versus host disease (GVHD), an autoimmune disease, sepsis, antibody-associated cytokine storm, anaphylaxis, adoptive cell therapy-associated cytokine storm, TNF-inhibition associated cytokine storm, distributive shock, inflammatory bowel disease (IBD), Chronic obstructive pulmonary disease (COPD), Cystic fibrosis (CF), asthma, Ebola virus disease (EVD), avian influenza, Spanish influenza, systemic inflammatory response syndrome (SIRS), Hemophagocytic lymphohistiocytosis and Epstein-Barr virus-related hemophagocytic lymphohistiocytosis.

According to some embodiments of the invention, the autoimmune disease is selected from the group consisting of rheumatoid arthritis, lupus, atherosclerosis, multiple sclerosis, hashimoto disease, type I diabetes, autoimmune pancreatitis, Crohn's and ulcerative colitis.

According to some embodiments of the invention, the cytokine storm syndrome is associated with an increase in at least one of tumor necrosis factor (TNF)-alpha, interferon (IFN)-gamma., IL-1α, IL-1β, IL-2, IL-5, IL-6, IL-7, IL-8, IL-12, IL-17, IL-18, IP-10, monocyte chemoattractant protein-1 (MCP-1), keratinocytes-derived chemokine (KC), MIP-la, RANTES and granulocyte colony-stimulating factor (G-CSF).

According to some embodiments of the invention, the tissue injury associated with inflammation is lung-associated.

According to some embodiments of the invention, the tissue injury associated with inflammation is associated with a medical condition selected from the group consisting of Acute respiratory distress syndrome (ARDS), Chronic obstructive pulmonary disease (COPD), Cystic fibrosis (CF), inflammatory bowel disease (IBD), and chronic wound.

According to some embodiments of the invention, the administering comprises parenteral or systemic administration.

According to some embodiments of the invention, the administering comprises intranasal administration.

According to some embodiments of the invention, the administering comprises at least one daily administration.

According to some embodiments of the invention, the administering is for at least 3 days.

According to some embodiments of the invention, the administering is for at least 5 days.

According to some embodiments of the invention, the administering is for 3-10 days.

According to some embodiments of the invention, the administering is for 5 days.

According to some embodiments of the invention, the composition is in a dry formulation.

According to some embodiments of the invention, the composition is in a liquid formulation.

According to some embodiments of the invention, the composition is for intranasal administration.

According to some embodiments of the invention, the composition is for inhalation administration.

According to some embodiments of the invention, the composition is for parenteral or systemic administration.

According to some embodiments of the invention, when the subject is diagnosed with SARS-CoV-2 the subject exhibits moderate severity of the disease according to at least one clinical parameter and one laboratory parameter:
  a. Clinical and Imaging-based evaluation
    i. Respiratory rate ≥23/min and ≤30/min
    ii. SpO$_2$ at room air ≤94% and >90%
    iii. Bilateral pulmonary infiltrates >50% within 24-48 hours or a severe deterioration compared to imaging at admission
  b. Evidence of an exacerbated inflammatory process
    i. LDH score >450 u/L
    ii. CRP >100 mg/L
    iii. Ferritin >1650 ng/ml
    iv. Lymphopenia <800 cells/mm$^3$
    v. D-dimer >1 mcg/mL According to some embodiments of the invention, the cell-derived particles are selected from the group consisting of exosomes, ARMM, microvesicles, exomeres, membrane particles, membrane vesicles and ectosomes.

According to some embodiments of the invention, the cell-derived particles have a mean particle diameter of about 30 to about 220 nm.

According to some embodiments of the invention, the cell-derived particles have a mean particle diameter of about 80 to about 220 nm.

According to some embodiments of the invention, the cell-derived particles are exosomes.

According to some embodiments of the invention, the cell is a cell of a human tissue.

According to some embodiments of the invention, the cell is a cell of an animal tissue.

According to some embodiments of the invention, the cell is a healthy cell.

According to some embodiments of the invention, the cell is a genetically modified cell.

According to some embodiments of the invention, the cell is a fibroblast cell or a kidney cell.

According to some embodiments of the invention, the cell is an embryonic kidney cell.

According to some embodiments of the invention, the cell is a HEK-293 cell.

According to some embodiments of the invention, the effective amount is $10^6$-$10^{13}$ particles per administration.

According to some embodiments of the invention, the effective amount is $10^7$-$10^{12}$ particles per administration.

According to some embodiments of the invention, the effective amount is $10^7$-$10^{10}$ particles per administration.

According to some embodiments of the invention, the effective amount is $10^7$-$10^9$ particles per administration.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 5C-5H illustrate particle concentration in the presence of different cell culture mediums. Cells were cultured with EX-Cell® medium (FIGS. 5C-D), with NutriVero™ medium (FIGS. 5E-F) or with Expi293™ medium supplemented with human serum albumin and insulin (FIGS. 5G-H). Of note, culture of cells with the Expi293™ supplemented culture medium resulted in the highest particle concentration and was uniform.

(FIG. 6A) The exosomes were bound to 96-well maxi-sorp plates and EXO-ELISA™ was performed using 20 μg/ml anti-CD24 mAb as the detecting antibody (HRP-conjugated anti-mouse antibody, diluted 1:5000, was used as secondary antibody). ELISA was developed using the chromogenic HRP substrate TMB. Color development was terminated with 1 M H2SO4 and the plates were read at 450 nm. (FIG. 6B) The exosomes were subjected to Western blot analysis for CD24. The membrane was reprobed with anti-HSP70 antibody to confirm that the sample was indeed an exosomal sample. In addition, CD24 recombinant protein was used as positive control for CD24 detection.

FIGS. 7A-7B illustrate Cryo-EM images of extracellular vesicles (EVs) isolated from T-REx™-293 cells that express high levels of human CD24. The arrows point to single vesicles (double-membrane vesicles). Scale bars are 100 nm (FIG. 7A) and 200 nm (FIG. 7B).

FIGS. 10A-10G illustrate the effect of Exo-CD24 on the secretion of different pro-inflammatory cytokines and chemokines in vitro. Results are presented for RANTES (FIG. 10A), IL-1β (FIG. 10B), CD40, a strong stimulator of cytokine secretion (FIG. 10C), MIP-3a (FIG. 10D), IL-1α (FIG. 10E), IL-6 (FIG. 10F) and MCP-1 (FIG. 10G). The graphs represent the average of duplicates in a single experiment. The Y axis represents the concentration of the analyte in pg/ml.

FIG. 11 illustrates no difference in animal weight during and following a five-day repeated inhalation administration of murine Exo-CD24.

FIG. 13 illustrates animal urine test markers at termination of a five-day repeated inhalation administration of murine Exo-CD24. Of note, no differences were observed.

FIGS. 17A-17C illustrate representative histological features for common lesion scores observed in the ARDS mouse model. (FIG. 17A) (saline) and (FIG. 17B) (low dose murine Exo-CD24, i.e. 1×10$^8$) show extensive neutrophil infiltrate in the alveolar spaces (arrows) and around the bronchi and blood vessels (arrowheads). The inflammatory infiltrate in (FIG. 17C) (high dose murine Exo-CD24, i.e. 1×10$^9$) is considerably attenuated. Arrows represent an example of neutrophils in the alveolar spaces. All images: hematoxylin and eosin (H&E) stain.

(FIGS. 18A-E) serum cytokines/chemokines, and (FIGS. 18F-J) BAL cytokines/chemokines. The bars represent the average (n=9-10) concentration in pg/ml±SEM. In each figure, the bars represent saline treatment, low concentration (1×10$^8$ particles, or high concentration (1×10$^9$) murine Exo-CD24.

FIGS. 20A-20B illustrate an improvement in lung affection in a Phase 1 clinical trial participant.

DESCRIPTION OF SPECIFIC EMBODIMENTS OF THE INVENTION

The present invention, in some embodiments thereof, relates to a composition comprising cell-derived particles presenting heterologous CD24 and uses of the composition is the treatment of a cytokine storm syndrome, coronavirus infection and tissue damage conditions associated with inflammation.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The SARS (severe acute respiratory syndrome) coronavirus 2 (SARS-CoV-2) is a newly discovered member of the family of coronaviruses. It is a respiratory virus that causes a disease known as COVID-19. Symptoms of COVID-19 can range from mild-illness characterized by fever, fatigue, dry cough and shortness of breath, to severe and acute respiratory distress syndrome (ARDS), renal dysfunction, and multi-organ failure, typically accompanied by a cytokine storm. Development of therapeutic modalities for the treatment of Coronavirus infection and the cytokine storm associate therewith is vital to the ability to overcome the pandemic.

Figure 1:
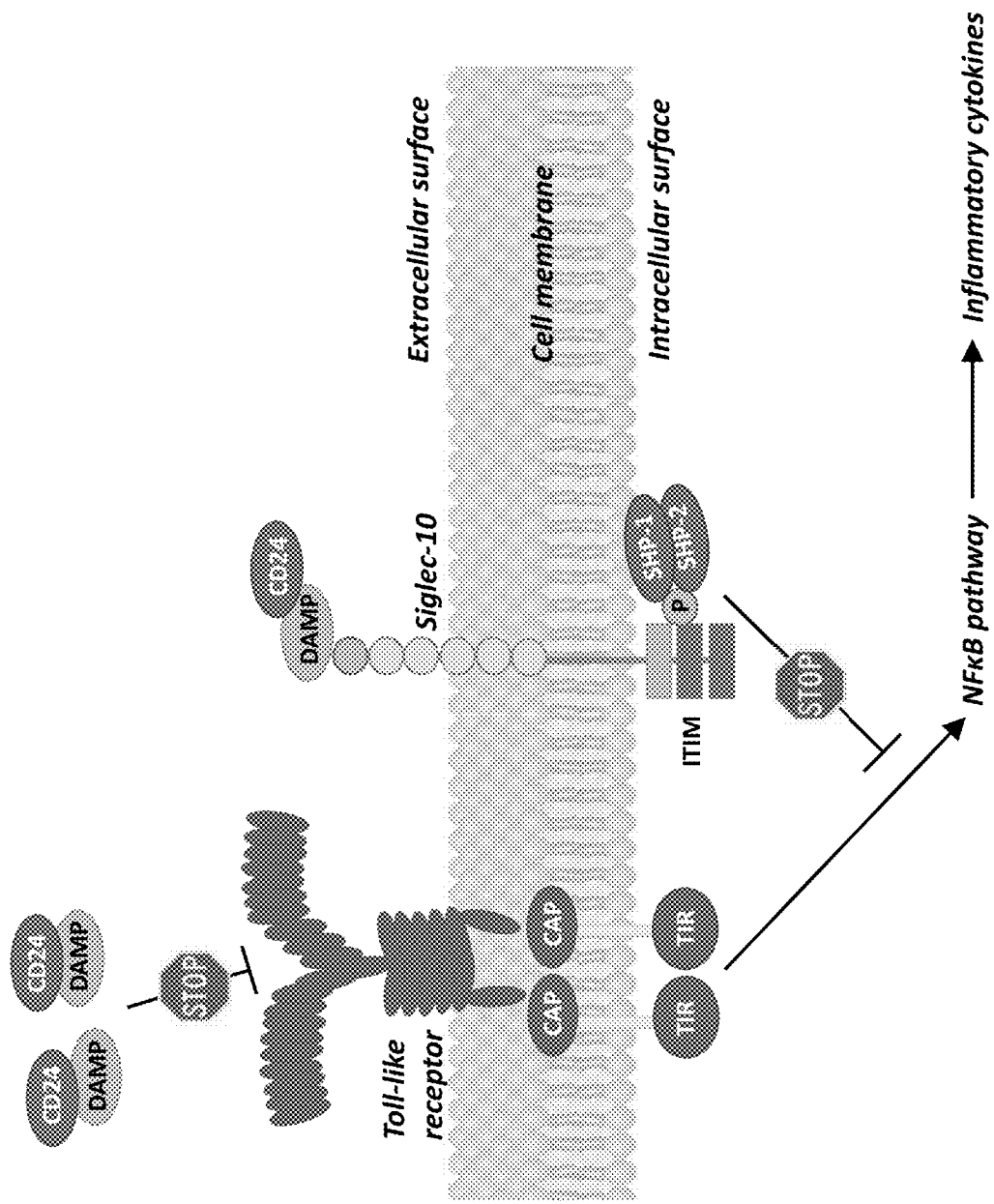
FIG. 1 illustrates negative regulation on the NFκB pathway by the CD24-Siglec-10 axis.

While reducing the present invention to practice, the present inventors have generated exosomes expressing CD24 which have the ability to suppress the hyper-activity of the immune system in the context of a SARS-Cov-2 infection and prevent the cytokine storm. The CD24-expressing exosomes of the invention can bind to DAMPs, thereby preventing their interaction with TLRs and inhibiting both NFκB activation and secretion of inflammatory cytokines. The CD24-expressing exosomes can also bind to Siglec-10 and down-regulate the exaggerated host response through the SHP-1 inhibitory pathway (as illustrated in FIG. 1).

As illustrated in the Examples section which follows, the CD24-expressing exosomes of the invention were isolated and purified from the culture medium of genetically engineered human T-REx™ cells (i.e. embryonic kidney T-REx™-293 cells), which were transfected with a plasmid comprising the human CD24 gene cloned downstream to two tetracycline-operator sequences. Specifically, following the addition of tetracycline to the cell culture medium (e.g. for 72 hours), the engineered cells constitutively expressed high levels of human CD24 which were presented on the cell membranes of the exosomes secreted therefrom (see Example 6, herein below). The generated CD24-expressing exosomes were shown to express high levels of CD24 (see Example 7, herein below), and to be non-toxic, safe and stable (when stored at −80° C. temperatures) (see Examples 8 and 10, herein below). Furthermore, the CD24-expressing exosomes, or murine versions thereof generated using the murine homolog of CD24 (HSA) in fibroblasts or in embryonic kidney cells, were shown to be highly effective in reducing cytokine levels based on both in vitro and in vivo testing (see Examples 9 and 12, herein below) as well as in reducing in vivo lung damage in an ARDS animal model (see Example 11, herein below) without inducing toxicity (see Example 10, herein below).

A GMP compliant manufacturing process has been fully established and validated for CD24-expressing exosomes enabling the clinical development thereof for human therapy. Phase I clinical trial has been completed on 35 subjects affected by severe COVID-19 disease accompanied by cytokine storm. The results of the Phase I clinical trial indicated a high safety profile as well as high efficacy for different doses of Exo-CD24 (e.g. $1\times10^8$-$1\times10^{10}$ exosome particles per day for 5 consecutive days) showing no adverse events or serious adverse events (see Example 12, herein below). All but one of the tested subjects showed clinical improvement within several days of treatment (e.g., within 1-3 days of treatment), as well as in 7- and 35-days follow-up as evident by improved lung function, oxygen saturation, respiratory rate, CRP levels and cytokine levels (see Example 12 and Tables 6-9, herein below).

Figures 6A, 6B:
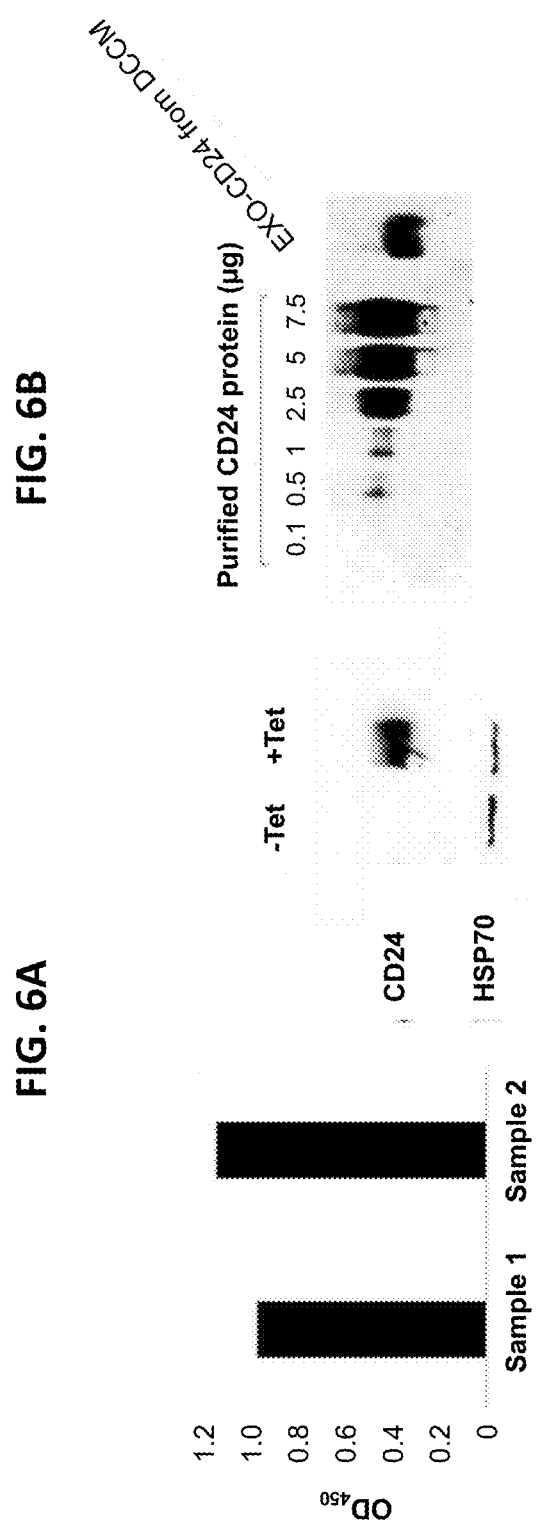
FIGS. 6A-6B illustrate an analysis of CD24 expression on the exosomal membrane of by ELISA.
Figure 6D:
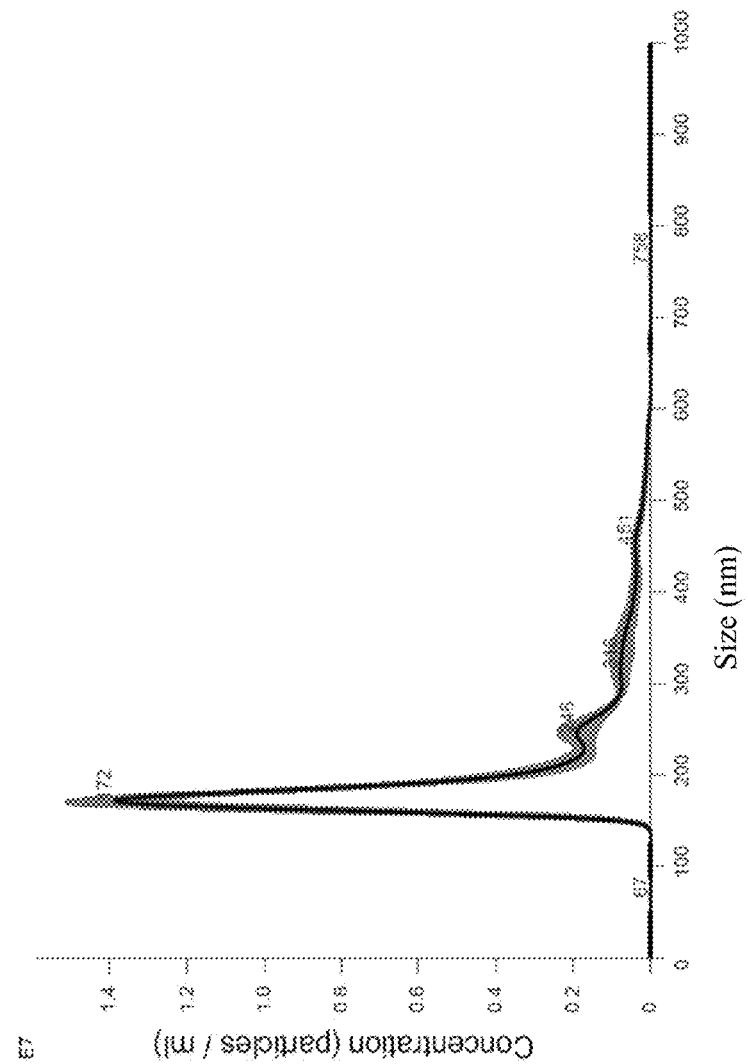
FIG. 6D illustrates size distribution of the purified exosomes obtained by suspension cultures as verified by Nano-Sight™.
Figure 6C:
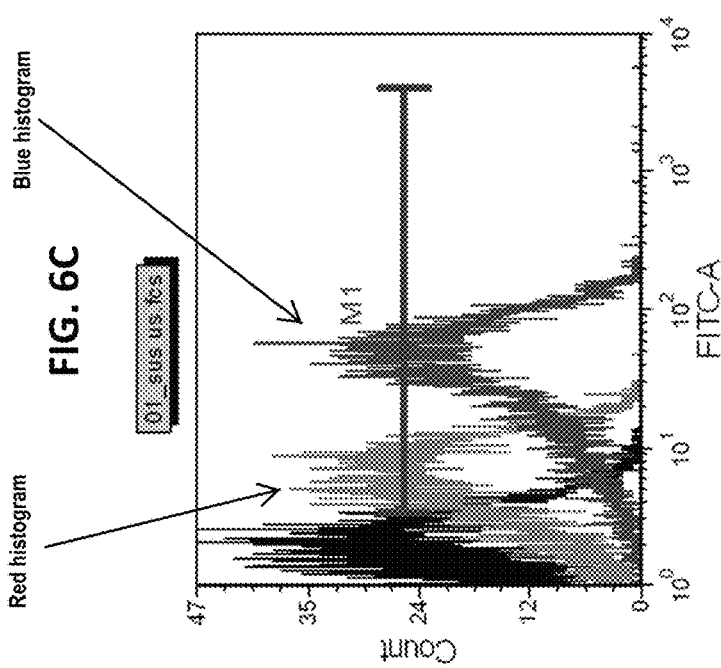
FIG. 6C illustrates expression of CD24 on exomes obtained in suspension cultures (by FACS analysis). The dark grey histogram shows the fluorescence intensity with 10 μg/ml anti-CD24 humanized mAb. The light grey histogram shows the fluorescence intensity with 1 μg/ml anti-CD24 humanized mAb.

The present inventors further uncovered means of producing increased levels of exosomes while supporting and solving biomanufacturing challenges (e.g. the balance of product quantity, quality, cost and speed). Specifically, genetically engineered human T-REx™ cells (i.e. Tet repressor-expressing HEK-293 cells cells) were grown in suspension cultures, in a shaker incubator, in the absence of serum. Specifically, the cells were cultured in Expi293™ medium supplemented with tetracycline, 72 hours later exosomes were collected, purified and examined for size distribution. As evident from the results, exosomes obtained from suspension cultures expressed CD24 and their size distribution was verified (FIGS. 6C-D). Furthermore, it was shown that increased levels of exosomes expressing CD24 and having uniform size distribution can be obtained in adherent cell cultures in which the Expi293™ medium was supplemented with 5% human serum albumin and 14 microU/ml Insulin (Example 2, below). The present inventors have further uncovered that commercial kits for harvesting exosomes, such as the CD24 presenting exosomes, can be replaced by a PEG-based method for purifying exosomes, in which a 10% PEG solution provides a pure population of exosomes having uniform size distribution (Example 2, below).

Taken together, CD24-expressing exosomes, such as Exo-CD24, is a novel therapeutic agent for the treatment of cytokine storm syndrome and ARDS, such as that caused by SARS-CoV-2, as well as for other tissue damage conditions associated with inflammation, specifically those involving damage-associated molecular patterns (DAMPs).

Thus, according to one aspect of the present invention there is provided a composition comprising cell-derived particles presenting heterologous CD24, wherein the cell is a non-cancerous cell and wherein the composition is substantially devoid of intact cells.

The term "CD24" refers to the protein product of the CD24 gene having a sequence as set forth in SEQ ID NO: 9 and homologs or fragments thereof (i.e. homologs or fragments capable of binding damage associated molecular patterns (DAMPs) and/or the pattern recognition receptors Siglecs, e.g. Siclec-10). Exemplary CD24 polypeptide sequences include, but are not limited to, those provided in GeneBank Accession Nos. NP_001278666.1, NP_001278667.1, NP_001278668.1, NP_001346013.1 and NP_037362.1, or homologs or fragments thereof.

According to one embodiment, the CD24 homolog comprises a sequence at least 80%, 81%, 829%, 83%, 849%, 85%, 86%, 87%, 88%, 89%, 90%, 91%, 92%, 93%, 94%, 95%, 96%, 97%, 98%, 99% homologous to SEQ ID NO: 9.

According to some embodiments of the invention, the term "homology" or "homologous" refers to identity of two or more nucleic acid sequences; or identity of two or more amino acid sequences; or the identity of an amino acid sequence to one or more nucleic acid sequence.

According to some embodiments of the invention, the homology is a global homology, i.e., a homology over the entire nucleic acid sequences of the invention and not over portions thereof.

The degree of homology or identity between two or more sequences can be determined using various known sequence comparison tools. Following is a non-limiting description of such tools which can be used along with some embodiments of the invention.

When starting with a polynucleotide sequence and comparing to other polynucleotide sequences the EMBOSS-6.0.1 Needleman-Wunsch algorithm (available from emboss (dot)sourceforge(dot)net/apps/cvs/emboss/apps/needle(dot) html) can be used.

According to some embodiment, determination of the degree of homology further requires employing the Smith-Waterman algorithm (for protein-protein comparison or nucleotide-nucleotide comparison).

According to some embodiments of the invention, the global homology is performed on sequences which are pre-selected by local homology to the polypeptide or polynucleotide of interest (e.g., 60% identity over 60% of the sequence length), prior to performing the global homology to the polypeptide or polynucleotide of interest (e.g., 80% global homology on the entire sequence). For example, homologous sequences are selected using the BLAST software with the Blastp and tBlastn algorithms as filters for the first stage, and the needle (EMBOSS package) or Frame+ algorithm alignment for the second stage. Local identity (Blast alignments) is defined with a very permissive cut-off—60% Identity on a span of 60% of the sequences lengths because it is used only as a filter for the global alignment stage. In this specific embodiment (when the local identity is used), the default filtering of the Blast package is not utilized (by setting the parameter "-F F"). In the second stage, homologs are defined based on a global identity of at least 80% to the core gene polypeptide sequence.

The CD24 polypeptide of some embodiments of the invention may be encoded by the sequence set forth in SEQ ID NO: 8. Additional exemplary CD24 sequences capable of encoding CD24 polypeptides include, but are not limited to, those provided in GeneBank Accession Nos. mRNAs: NM_001291737.1 NM_001291738.1 NM_001291739.1 NM_001359084.1 and NM_013230.3.

According to one embodiment, the CD24 is a human CD24 or a recombinant version thereof.

According to one embodiment, the CD24 is capable of binding damage associated molecular patterns (DAMPs) and/or the pattern recognition receptors Siglecs (e.g. Siclec-10).

According to one embodiment, the CD24 is not part of a fusion protein comprising the extracellular domain of CD24 linked to a human immunoglobulin G1 (IgG1) Fc domain (i.e. CD24Fc), e.g., as taught in Bradley, *Nature Reviews Cancer* (2019) 19: 541 and in Tian R et al., *Cellular & Molecular Immunology* (2020) 17: 887-888.

The term "heterologous" presentation as used herein refers to the recombinant expression of a gene or fragment thereof (e.g. CD24 or fragment thereof) in a cell or particle derived therefrom (e.g. on the cell membrane of the cell or cell-derived particle) which does not naturally express this gene or gene fragment.

The term "cell-derived particles" as used herein refers to externally released vesicles, also referred to as extracellular vesicle (EV), that are obtainable from a cell in any form.

According to one embodiment, the cell-derived particles include, for example, microvesicles (e.g. vesicles that shed/bud/bleb from the plasma membrane of a cell and have irregular shapes), membrane particles (e.g. vesicles that shed/bud/bleb from the plasma membrane of a cell and are round-shaped), membrane vesicles (e.g. micro vesicles), exosomes (e.g. vesicles derived from the endo-lysosomal pathway), apoptotic bodies (e.g. vesicles obtained from apoptotic cells), microparticles (e.g. vesicles derived from e.g. platelets), ectosomes (e.g. vesicles derived from e.g. neutrophils and monocytes in serum), cardiosomes (e.g. vesicles derived from cardiac cells), arrestin domain-containing protein 1 (ARRDC1)-mediated microvesicles (ARMM) (e.g. vesicles produced directly at the plasma membrane and which require arrestin-domain containing protein 1 (ARRDC1) for budding) and exomeres (e.g. vesicles smaller than 50 nm and typically carrying proteins involving metabolism).

According to one embodiment, the cell-derived particles are generated by disruption of cell membranes using synthetic means, e.g., sonication, homogenization extrusion, etc.

According to one embodiment, the cell-derived particles are cell-secreted particles (also referred to as cell-secreted vesicles).

For example, exosomes are formed by invagination and budding from the limiting membrane of late endosomes. They accumulate in cytosolic multivesicular bodies (MVBs) from where they are released by fusion with the plasma membrane. Alternatively, vesicles similar to exosomes (e.g. microvesicles or membrane particles) can be released directly from the plasma membrane. Each type of cell-derived particles express distinctive biomarkers. For example, membrane particles typically express CD133 (prominin-1), microvesicles typically express integrins, selectins, and CD40, while exosomes typically express CD63, CD81, CD9, CD82, CD37, CD53, or Rab-5b.

According to one embodiment, the cell-derived particles comprise the membrane arrangement of a cell. They may comprise any cell-originated molecules, carbohydrates and/or lipids that are typically presented in a cell membrane.

Depending on the cellular origin, cell-derived particles harbor biological material including e.g. nucleic acids (e.g. RNA or DNA), or cytoplasmic content including proteins, peptides, polypeptides, antigens, lipids, carbohydrates, and proteoglycans. For example, various cellular proteins can be found in cell-derived particles including MHC molecules, tetraspanins, adhesion molecules and metalloproteinases.

According to one embodiment, the cell-derived particles are deprived of cytoplasmic content.

The size of cell-derived particles can vary considerably, but typically cell-derived particles are of a nano-size, i.e. a diameter below 1000 nm.

Thus, according to one embodiment, the cell-derived particles are nanovesicles (i.e. nanoparticles).

According to one embodiment, the cell-derived particles have a particle size (e.g. diameter) of about 10-1000 nm, about 10-750 nm, about 10-500 nm, about 10-250 nm, about 10-100 nm, about 10-50 nm, about 10-25 nm, about 10-20 nm, about 20-1000 nm, about 20-750 nm, about 20-500 nm, about 20-250 nm, about 20-100 nm, about 20-50 nm, about 30-200 nm, about 30-100 nm, about 30-50 nm, about 50-1000 nm, about 50-750 nm, about 50-500 nm, about 50-100 nm, about 80-1000 nm, about 80-500 nm, about 80-250 nm, about 80-150 nm, about 100-1000 nm, about 100-750 nm, about 100-500 nm, about 100-250 nm, about 100-150 nm, about 200-1000 nm, about 200-750 nm, about 200-500 nm, or about 200-250 nm.

According to one embodiment, the cell-derived particles have a particle size (e.g. diameter) of about 10, 20, 30, 40, 50, 60, 70, 80, 90, 100, 150, 200, 250 300, 500 or 1000 nm.

According to one embodiment, the cell-derived particles have a particle size (e.g. diameter) of no more than about 1000 nm, 750 nm, 500 nm, 250 nm, 200 nm, 150 nm, 100 nm, 50 nm, 25 nm, 20 nm or 10 nm.

According to a specific embodiment, the cell-derived particles comprise a particle size (e.g. diameter) of about 30-220 nm (e.g., about 30-200 nm, about 30-100 nm, about 80-220, about 100-200 nm).

According to one embodiment, the cell-derived particles have an average particle size, namely the numbers provided herein relate to discrete particles or a particle population in which the average particle size (e.g. diameter) is of about 30-220 nm (e.g., about 30-200 nm, about 30-100 nm, about 80-220, about 100-200 nm).

According to a specific embodiment, the cell-derived particles comprise exosomes.

According to one embodiment, the cell-derived particles comprise exosomes having a particle size (e.g., diameter) of about 30-220 nm (e.g., about 30-150 nm).

According to a specific embodiment, the cell-derived particles comprise microvesicles.

According to one embodiment, the cell-derived particles comprise microvesicles having a particle size (e.g. diameter) of about 100-1000 nm (e.g., about 500-1000 nm, about 300-500 nm, about 100-500 nm, about 100-300 nm, about 100-200 nm).

Cell-derived particles can be identified using methods well known in the art, e.g. by electron microscopy (EM) and nanoparticle tracing analysis (NTA), and their biomarker expression can be determined using methods well known in the art, for example, by Western blot, ELISA and Flow cytometry assay (e.g. FACS).

According to one embodiment, cell-derived particles are obtained from cells of a human or animal tissue.

According to one embodiment, cell-derived particles are obtained from cells of an animal selected from a mammal, a fish, an amphibian, a reptile, and a bird.

According to one embodiment, the animal is a mammal, including but not limited to a mouse, a rat, a hamster, a guinea pig, a gerbil, a hamster, a rabbit, a cat, a dog, a pig (e.g. swine), a cow, a goat, a sheep, a primate, an elephant and a horse.

Depending on the application and available sources, the cell-derived particles of the invention are obtained from cells of a prenatal organism (e.g. fetus), postnatal organism, an adult or a cadaver. Such determinations are well within the ability of one of ordinary skill in the art.

According to one embodiment, cell-derived particles are obtained from embryonic cells.

According to one embodiment, cell-derived particles are obtained from stem cells.

According to one embodiment, cell-derived particles are obtained from differentiated cells.

According to one embodiment, the cell-derived particles are obtained from healthy cells (e.g. non-cancerous cells).

According to one embodiment, cell-derived particles are obtained from any of various cell types, normal and diseased, including but not limited to, kidney cells, fibroblast cells, liver cells, intestinal cells, cervical cells, ovarian cells, bone cells, cardiac cells, pulmonary cells, hematopoietic cells, and stem cells.

According to a specific embodiment, the cell-derived particles are obtained from kidney cells.

According to a specific embodiment, the cell-derived particles are obtained from embryonic kidney cells.

According to a specific embodiment, the cell-derived particles are obtained from HEK-293 cells (also referred to as HEK cells or 293 cells).

According to a specific embodiment, the cell-derived particles are obtained from fibroblasts.

According to a specific embodiment, the cell-derived particles are obtained from embryonic fibroblast cells.

According to a specific embodiment, the cell-derived particles are obtained from NIH3T3 cells (also referred to as 3T3 cells).

Commercially available cells, e.g. kidney cells, such as HEK-293 cells, or fibroblasts, such as NIH3T3, can be used with this aspect of the present invention. Human HEK-293 cells can be purchased from e.g. the ATCC (American Type Culture Collection—www(dot)atcc(dot)org), such as ATCC® CRL-1573™. NIH3T3 cells can be purchased from e.g. the ATCC, such as ATCC® CRL-1658™.

According to one embodiment, the cell-derived particles are not obtained from lymphocytes (e.g. B cells or T cells), neutrophils, mesenchymal stromal cells (MSCs), amnion epithelial (AE) cells or placenta-derived cells.

According to one embodiment, the cell-derived particles are obtained from cell lines or primary cultures of cells (e.g. of non-cancerous cells).

According to one embodiment, the cell-derived particles are obtained from cell lines or primary cultures transformed to stably express a repressor protein, such as the tetracycline repressor protein, or the multiple antibiotic resistance (MAR) repressor.

According to a specific embodiment, the cell-derived particles are obtained from T-REx™ Cell Lines that stably express the tetracycline repressor protein.

According to a specific embodiment, the cell-derived particles are obtained from Tet repressor-expressing HEK-293 cells (i.e. T-REx™-293 Cell Lines) that stably express the tetracycline repressor protein.

Commercially available T-REx™-293 cells can be used with this aspect of the present invention. T-REx™-293 cells can be purchased from e.g. Thermo Fisher Scientific.

According to one embodiment of the invention, the cell-derived particles are obtained from cells which do not naturally present CD24 on their cell membrane (e.g. kidney cells or fibroblasts). Methods of measuring expression of CD24 polypeptides on a cell are well known in the art and include, e.g. ELISA, Western blot analysis, and Flow cytometry assay (e.g. FACS).

According to one embodiment of the invention, the cell-derived particles are obtained from cells which do not naturally present human CD24 (e.g. animal cells, as discussed above).

According to one embodiment of the invention, the cell-derived particles are obtained from cells which are genetically manipulated to express CD24 or recombinant versions thereof (e.g. genetically modified cells, as further discussed below).

According to one embodiment of the invention, the cell-derived particles are obtained from cells which are chemically manipulated to express CD24 or recombinant versions thereof (e.g. genetically non-modified cells, as further discussed below).

Depending on the application, the cell-derived particles presenting CD24 may be obtained from cells of an organism which is syngeneic or non-syngeneic with a subject to be treated (discussed in detail herein below).

As used herein, the term "syngeneic" cells refer to cells which are essentially genetically identical with the subject or essentially all lymphocytes of the subject. Examples of syngeneic cells include cells derived from the subject (also referred to in the art as an "autologous"), from a clone of the subject, or from an identical twin of the subject.

As used herein, the term "non-syngeneic" cells refer to cells which are not essentially genetically identical with the subject or essentially all lymphocytes of the subject, such as allogeneic cells or xenogeneic cells.

As used herein, the term "allogeneic" refers to cells which are derived from a donor who is of the same species as the subject, but which is substantially non-clonal with the subject. Typically, outbred, non-zygotic twin mammals of the same species are allogeneic with each other. It will be appreciated that an allogeneic cell may be HLA identical, partially HLA identical or HLA non-identical (i.e. displaying one or more disparate HLA determinant) with respect to the subject.

As used herein, the term "xenogeneic" refers to a cell which substantially expresses antigens of a different species relative to the species of a substantial proportion of the lymphocytes of the subject. Typically, outbred mammals of different species are xenogeneic with each other. Xenogeneic cells may be derived from a variety of species, such as animals (e.g. mammals, such as major domesticated or livestock animals and primates).

According to one embodiment, the cell-derived particles of the invention are obtained from cells allogeneic with the subject.

Obtaining cell-derived particles may be carried out using any method known in the art. For example, cell-derived particles can be isolated (i.e. at least partially separated from the natural environment e.g., from a body) from any biological sample (e.g., fluid or hard tissue) comprising the cell-derived particles. Examples of fluid samples include, but are not limited to, whole blood, plasma, serum, spinal fluid, lymph fluid, bone marrow suspension, cerebrospinal fluid, brain fluid, ascites (e.g. malignant ascites), tears, saliva, sweat, urine, semen, sputum, ear flow, vaginal flow, secretions of the respiratory, intestinal and genitourinary tracts, milk, amniotic fluid, and biofluids of ex vivo or in vitro cell cultures. Examples of tissue samples include, but are not limited to, surgical samples, biopsy samples, tissues, feces, and ex vivo cultured tissues (e.g. explants). According to a specific embodiment, the tissue sample comprises a whole or partial organ (e.g. kidney, lung), such as those obtained from a cadaver or from a living subject undergoing whole or partial organ removal.

According to a specific embodiment, the biological sample comprises the biofluid (e.g. culture medium) in which cell lines or primary cultures of cells were grown or maintained.

Methods of obtaining such biological samples are known in the art, and include without being limited to, standard blood retrieval procedures, standard urine and semen retrieval procedures, lumbar puncture, fine needle biopsy, needle biopsy, core needle biopsy and surgical biopsy (e.g., organ or brain biopsy), buccal smear, lavage and standard culture medium retrieval procedures for cell cultures. Regardless of the procedure employed, once a biological sample is obtained cell-derived particles can be obtained therefrom.

The volume of the biological sample used for obtaining cell-derived particles can be in the range of between 0.1 mL-1000 L, such as about 100 mL-250 mL, 100 mL-500 mL, 100 mL-750 mL, 100 mL-1 L, about 250 mL-500 mL, about 250 mL-750 mL, about 250 mL-1 L, about 250 mL-2.5 L, about 500 mL-750 mL, about 500 mL-1 L, about 500 mL-1.5 L, about 500 mL-2.5 L, about 500 mL-5 L, about 1 L-1.5 L, about 1 L-2 L, about 1 L-2.5 L, about 1 L-3 L, about 1 L-4 L, about 1 L-5 L, about 1 L-7.5 L, about 1 L-10 L, about 5 L-7.5 L, about 5 L-10 L, about 5 L-15 L, about 5 L-20 L, about 5 L-25 L, about 5 L-50 L, about 10 L-15 L, about 10 L-20 L, about 10 L-30 L, about 10 L-40 L, about 10 L-50 L, about 10 L-60 L, about 10 L-70 L, about 10 L-80 L, about 10 L-90 L, about 10 L-100 L, about 25 L-50 L, about 25 L-75 L, about 25 L-100 L, about 25 L-250 L, about 50 L-75 L, about 50 L-100 L, about 50 L-250 L, about 50 L-500 L, about 100 L-200 L, about 100 L-250 L, about 100 L-500 L, about 100 L-750 L, about 100 L-1000 L, about 200 L-300 L, about 300 L-400 L, about 400 L-500 L, about 500 L-600 L, about 600 L-700 L, about 700 L-800 L, about 800 L-900 L, or about 900 L-1000 L.

The biological sample of some embodiments of the invention may comprise cell-derived particles in various amounts, such as but not limited to, about $1\times10^1$-$1\times10^{30}$, about $1\times10^2$-$1\times10^4$, about $1\times10^3$-$1\times10^6$, about $1\times10^4$-$1\times10^8$, about $1\times10^5$-$1\times10^{10}$, about $1\times10^6$-$1\times10^{12}$, about $1\times10^7$-$1\times10^{14}$, about $1\times10^8$-$1\times10^{16}$, about $1\times10^9$-$1\times10^{18}$, about $1\times10^{10}$-$1\times10^{15}$, about $1\times10^{10}$-$1\times10^{20}$, about $1\times10^{11}$-$1\times10^{22}$, about $1\times10^{12}$-$1\times10^{24}$, about $1\times10^{13}$-$1\times10^{26}$, about $1\times10^{14}$-$1\times10^{28}$ or about $1\times10^{15}$-$1\times10^{30}$ (e.g. at least about 10, 15, 20, 25, 50, 100, 150, 200, 250, 500, 1000, 2000, 5000, 10,000, 50,000, 100,000, 500,000, 750,000, $1\times10^6$, $1\times10^7$, $1\times10^8$, $1\times10^9$, $1\times10^{10}$, $1\times10^{15}$, $1\times10^{20}$, $1\times10^{25}$ or more cell-derived particles, as further discussed below).

According to one embodiment, cell-derived particles are obtained from a freshly collected biological sample or from a biological sample that has been stored, lyophilized (freeze-dried), cryopreserved or cooled.

According to one embodiment, cell-derived particles are obtained from a culture medium in which the cells have been cultured.

For example, cell-derived particles (e.g. cell-secreted particles, including exosomes) can be isolated from the biological sample by any method known in the art. Suitable methods are taught, for example, in U.S. Pat. Nos. 9,347,087 and 8,278,059, incorporated herein by reference.

According to one embodiment, cell-derived particles are obtained from a sample (e.g. fluid sample) by a polyethylene glycol (PEG)-based method. Such methods have been adapted from methods for isolating viruses using PEG. For example, a PEG-based method for purifying exosomes and other extracellular vesicles, termed ExtraPEG, enriches exosomes from large volumes of media rapidly and inexpensively using low-speed centrifugation, followed by a single small-volume ultracentrifugation purification step. Total protein and RNA harvested from vesicles is sufficient in quantity and quality, as discussed in Rider et al. *Scientific Reports* (2016) 6, Article number: 23978, incorporated herein by reference. An additional method of isolation of cell-derived particles, e.g. exosomes, with PEG from cell culture supernatants is discussed in Weng et al., *Analyst* (2016) 141(15):4640-6, incorporated herein by reference.

According to one embodiment, cell-derived particles are obtained from a sample (e.g. fluid sample) using a commercially available exosome purification kit. Such a kit includes, but is not limited to, ExoQuick® available from e.g. System Biosciences.

For example, cell-derived particles (e.g. cell-secreted particles, including exosomes) may be obtained from a fluid sample by first collecting the biofluid (e.g. cell culture medium) and centrifuging (e.g. at 3000×g for 10-30 minutes, e.g. for 15 minutes, at about 4° C.) to remove cells and cell debris. The supernatant may then be filtered using, for example, a 0.22 micron pore size filter. Next, an exosome isolation kit may be used, such as the one commercially available from SBI System Biosciences, e.g. ExoQuick® Exosome Isolation and RNA Purification Kit. Specifically, per the vendor's guidelines, ExoQuick®-CG exosome precipitation solution may be added to the biofluid (e.g. 3.3 ml/10 ml biofluid), the tubes mixed (e.g. by gentle inversion) and stored in a refrigerator (e.g. for at least 12 hours, such as overnight). On the following day, the ExoQuick-CG/biofluid mixture may be centrifuged (e.g. at 2500×g for 30 minutes, at about 4° C.), and the supernatant aspirated. The residual ExoQuick®-CG solution may be removed (e.g. by centrifugation at 2500×g for 5 minutes), followed by aspiration of all traces of fluid. The exosomes in the pellet may be re-suspended in saline (e.g. 0.5-2.5 ml) and transferred to a dialysis cassette. Dialysis may be performed against, for example, 4-6 L, e.g. 5 L, of fresh PBS (e.g. overnight, at about 4° C.). The exosomes may then be transferred into a centrifugal filter, such as Amicon tube (e.g. 10000 MW), and centrifuged (e.g. at about 15° C.) until they reach the preferred volume. The purified exosomes may then be filtered (e.g. sterile), using for example a sterile 0.22 micron pore size filter, into cryo-tube (e.g. a 2 ml PP, round bottom, natural screw cap, sterile, Greiner, Lot 121263).

According to another exemplary embodiment, cell-derived particles (e.g. cell-secreted particles, including exosomes) may be obtained from a fluid sample by first collecting the biofluid (e.g. cell culture medium) and adding PEG solutions (comprising, for example, Mn (e.g. at a molecular weight of 5,000-7,000, e.g. at a molecular weight average of 6000), ultra-pure water and sodium chloride (e.g. 0.5 M)) thereto. The PEG solutions may be used at different concentrations, e.g. at a concentration of 1-20% PEG, e.g. 5-15% PEG, e.g. 5-10% PEG, e.g. 10-12% PEG. The fluid sample comprising the PEG solution is typically refrigerated overnight (at about 4° C.). The following day, samples are typically centrifuged at about 4° C., for about 1 hour at maximum speed. The particles are obtained by suspending the resulting pellets in saline (NaCl 0.9%).

According to one embodiment, the primary culture, tissue or cell line is cultured in a culture medium prior to obtaining a cell-derived particles therefrom. One of ordinary skill in the art is capable of determining the length of time of which the cells may be cultured and the type of medium used for culturing. According to one embodiment, the cells are cultured for 12 hours, 24 hours, 36 hours, 48 hours, 72 hours, 4 days, 5 days, 6 days, 7 days, 10 days, 14 days, 21 days, 30 days or more.

As used herein the phrase "culture medium" refers to a liquid substance used to support the growth of cells. The culture medium used by the invention according to some embodiments can be a water-based medium which includes a combination of substances such as salts, nutrients, minerals, trace elements, vitamins (e.g. fat-soluble vitamins such as A, D, E, and K), carbohydrates, lipids, amino acids, proteins such as cytokines, growth factors and hormones, or any combination thereof, all of which are needed for cell growth (i.e. proliferation) and/or for production of cell-derived particles.

For example, a culture medium according to an aspect of some embodiments of the invention can be a synthetic tissue culture medium comprising a basal medium such as the Dulbecco's Modified Eagle's Medium (DMEM, available for example from Gibco-Invitrogen Corporation products, Grand Island, NY, USA), Expi293™ medium (available for example from Thermo Fisher Scientific), EX-Cell® medium (available for example from Merck or Sigma Aldrich), NutriStem® hPSc medium (e.g. NutriStem® hPSC XF Medium, available for example from Biological Industries), NutriVero™ medium (e.g. NutriVero™ Flex 10, available for example from Biological Industries), supplemented with the necessary additives as is further described herein under. The concentration of the basal medium depends on the concentration of the other medium ingredients such as the serum albumin as discussed below.

According to one embodiment of the invention, the culture medium comprises the Expi293™ medium.

According to one embodiment, the cells are cultured in a defined culture medium prior to obtaining cell-derived particles therefrom. A "defined" culture medium refers to a chemically-defined culture medium manufactured from known components at specific concentrations. For example, a defined culture medium may be animal origin-free, protein-free and/or serum-free (e.g. may be an Expi293™ medium).

According to one embodiment of the invention, the culture medium comprises the Expi medium (e.g. Expi293™).

According to one embodiment, the cells are cultured in a defined culture medium prior to obtaining cell-derived particles therefrom. A "defined" culture medium refers to a chemically-defined culture medium manufactured from known components at specific concentrations. For example, a defined culture medium may be animal origin-free, protein-free and/or serum-free (e.g. may be an Expi medium).

According to some embodiments of the invention, the culture medium is xeno-free.

According to one embodiment, the culture medium is serum-free.

As used herein the phrase "serum-free" refers to being devoid of a human or an animal serum.

It should be noted that the function of serum in culturing protocols is to provide the cultured cells with an environment similar to that present in vivo (i.e., within the organism from which the cells are derived). However, the use of serum, which is derived from either an animal source (e.g., bovine serum) or a human source (human serum), is limited by the significant variations in serum components between the donor individuals (from which the serum is obtained) and the risk of having xeno contaminants (in case of an animal serum is used).

According to some embodiments of the invention, the serum-free culture medium does not comprise serum or portions thereof.

According to some embodiments of the invention, the serum-free culture medium is devoid of serum albumin (e.g., albumin which is purified from human serum or animal serum).

According to some embodiments of the invention, the serum-free culture medium comprises serum albumin (e.g., human serum albumin).

According to one embodiment, the concentration of albumin in the culture medium is about 0.5-30% (v/v), 0.5-10% (v/v), 0.5-5% (v/v), e.g. about 0.5-1% (v/v), e.g. about 1-3% (v/v), e.g. about 1-5% (v/v), e.g. about 2-4% (v/v), e.g. about 2-6% (v/v), e.g. about 3-5% (v/v), e.g. about 3-7.5% (v/v), e.g. about 5-7.5% (v/v), e.g. about 5-10% (v/v), e.g. about 7.5-10% (v/v), e.g. about 10-15% (v/v), e.g. about 10-20% (v/v), e.g. about 15-25% or e.g. about 20-30%.

According to a specific embodiment, the concentration of albumin in the culture medium is about 3-5% (v/v).

The term "albumin" as used herein refers to the blood protein which acts as a carrier protein for a wide range of endogenous molecules including, for example, hormones, fatty acids, and metabolite.

According to one embodiment, the albumin is a human serum albumin (HSA).

The albumin used in the culture medium of some embodiments of the invention can be a purified, a synthetic or a recombinantly expressed albumin (e.g., human albumin protein, such as set forth in GenBank Accession No.: NP_000468.1). For example, the recombinant albumin e.g. Albagen which is a recombinant human serum albumin with deletion of the N-terminal residue (Asp).

According to one embodiment, albumin comprises HSA—human serum albumin 200 gr/ml solution for infusion, commercially available from e.g. Kedrion Biopharma.

Commercially available human serum albumin can be obtained, for example, from Proteintech or Sigma Aldrich.

According to a specific embodiment, the concentration of albumin in the culture medium is about 0.5% (v/v).

According to a specific embodiment, the concentration of albumin in the culture medium is about 1% (v/v).

According to a specific embodiment, the concentration of albumin in the culture medium is about 5% (v/v).

According to a specific embodiment, the concentration of albumin in the culture medium is about 10% (v/v).

According to some embodiments of the invention, the culture medium (e.g. serum-free culture medium) comprises insulin.

The term "insulin" as used herein refers to a peptide hormone that plays a vital role in the regulation of carbohydrate and lipid metabolism.

According to one embodiment, the insulin is human insulin. Human insulin typically consists of two polypeptide chains, the A and B chains which contain 21 and 30 amino acid residues, respectively.

The insulin used in the culture medium of some embodiments of the invention can be a purified, a synthetic or a recombinantly expressed insulin protein (e.g., human insulin protein such as set forth in GenBank Accession Nos.: NP_000198.1, NP_001172026.1, NP_001172027.1, or NP_001278826.1).

The insulin used in the culture medium of some embodiments of the invention is a naturally occurring insulin, e.g., human insulin, as well as insulin analogues e.g. a human insulin wherein one or more of the amino acids have been exchanged with other amino acids.

Commercially available insulin can be obtained for example from Invitrogen.

According to a specific embodiment, the insulin comprises recombinant insulin, such as Actrapid®, commercially available from e.g. Novo Nordisk.

According to one embodiment, the concentration of insulin in the culture medium is about 1-50 microU/ml, e.g. about 1-5 microU/ml, e.g. about 5-10 microU/ml, e.g. about 10-15 microU/ml, e.g. about 15-25 microU/ml, or e.g. about 25-50 microU/ml.

According to a specific embodiment, the concentration of insulin in the culture medium is about 5 microU/ml.

According to a specific embodiment, the concentration of insulin in the culture medium is about 10 microU/ml.

According to a specific embodiment, the concentration of insulin in the culture medium is about 15 microU/ml.

According to a specific embodiment, the concentration of insulin in the culture medium is about 20 microU/ml.

According to a specific embodiment, the Expi293™ medium is not supplemented with serum, i.e. is serum-free.

According to a specific embodiment, the Expi293™ medium is supplemented with insulin (e.g. 1-50 microU/ml Insulin, e.g. 5-40 microU/ml Insulin, e.g. 10-20 microU/ml Insulin, e.g. 14 microU/ml Insulin).

According to a specific embodiment, the Expi293™ medium is supplemented with human serum albumin (e.g. 1-20%, e.g. 1-15%, e.g. 1-10%, e.g. 5% human serum albumin).

According to a specific embodiment, the Expi293™ medium, is supplemented with human serum albumin (e.g. 1-20%, e.g. 1-15%, e.g. 1-10%, e.g. 5% human serum albumin) and insulin (e.g. 1-50 microU/ml Insulin, e.g. 5-40 microU/ml Insulin, e.g. 10-20 microU/ml Insulin, e.g. 14 microU/ml Insulin).

According to one embodiment, the cell culture medium is supplemented with an antibiotic, e.g. tetracycline.

According to a specific embodiment, when the cells are T-REx™ Cell Lines (e.g. T-REx™-293 cells) that stably express the tetracycline repressor protein, the cells are preferably first cultured in a culture medium comprising tetracycline (e.g. 0.1-5 pg/ml, e.g. 1 µg/ml, e.g. for 2-5 days, e.g. for 72 hours) in order to induce expression of the gene of interest (i.e. CD24 which is under the control of tetracycline-operator sequences) prior to obtaining cell-derived particles therefrom.

According to one aspect of the invention, there is provided a culture medium comprising Expi293™ medium, insulin and albumin.

According to one embodiment, there is provided a cell culture comprising cells and the medium of some embodiments of the invention.

According to one embodiment, the cells comprise cells modified to present CD24, e.g. genetically modified cells or chemically modified cells.

According to one embodiment, the cells comprise kidney or fibroblast cells modified to present CD24, e.g. genetically modified cells or chemically modified cells.

According to one embodiment, the cells comprise HEK-293 cells modified to present CD24, e.g. genetically modified cells or chemically modified cells.

According to one embodiment, the cells comprise NIH3T3 cells modified to present CD24, e.g. genetically modified cells or chemically modified cells.

According to one embodiment, the cells are cultured under adherent conditions, i.e. in a 2-dimensional (2D) culture.

The term "2-dimensional culture" or "2D culture" refers to the growth of cells under matrix adherence.

As used herein, the term "matrix" refers to any substance to which the cells can adhere and which therefore can provide the cell attachment function. Such a matrix may contains extracellular components to which the cells can attach and thus it may provide a suitable culture substrate.

According to one embodiment, the matrix is an extracellular matrix or a synthetic matrix.

The extracellular matrix can be composed of components derived from basement membrane or extracellular matrix components that form part of adhesion molecule receptor-ligand couplings. MATRIGEL® (Becton Dickinson, USA) is one example of a commercially available matrix which is suitable for use with the present invention. MATRIGEL® is a soluble preparation from Engelbreth-Holm-Swarm tumor cells that gels at room temperature to form a reconstituted basement membrane; MATRIGEL® is also available as a growth factor reduced preparation. Other extracellular matrix components and component mixtures which are suitable for use with the present invention include foreskin matrix, laminin matrix, fibronectin matrix, proteoglycan matrix, entactin matrix, heparan sulfate matrix, collagen matrix and the like, alone or in various combinations thereof.

According to some embodiments of the invention the matrix is devoid of animal contaminant (i.e. is a xeno-free matrix).

In cases where complete animal-free culturing conditions are desired, the matrix is preferably derived from a human source or synthesized using recombinant techniques.

Such matrices include, for example, human-derived fibronectin, recombinant fibronectin, human-derived laminin, foreskin fibroblast matrix or a synthetic fibronectin matrix. Human derived fibronectin can be from plasma fibronectin or cellular fibronectin, both of which can be obtained from Sigma, St. Louis, Mo., USA. Human derived laminin and foreskin fibroblast matrix can be obtained from Sigma, St. Louis, Mo., USA. A synthetic fibronectin matrix can be obtained from Sigma, St. Louis, Mo., USA.

According to some embodiments of the invention the matrix is a glass microcarrier or beads.

According to one embodiment, the 2D cultures comprise coated surfaces onto which the cells can adhere. Coating strategies for 2D cultures of cells are discussed in Cimino et al., *Stem Cells International* (2017) Article ID 6597815, incorporated herein by reference.

According to one embodiment, the 2D cultures are not coated, e.g. with extracellular matrix (ECM) proteins, such as collagen, or other commercially available cell adhesion factors.

According to one embodiment, culturing cells in 2D cultures is affected by seeding the cells (e.g. kidney cells, e.g. HEK-293 cells, or fibroblasts, e.g. such as NIH3T3) in a culture plate at a cell density which promotes cell survival, proliferation and production of cell-derived particles. Typically, a plating density (or a seeding density) of between about $2.5 \times 10^6$ cells/175 cm$^2$ to about $6 \times 10^6$ cells/175 cm$^2$ is used.

According to one embodiment, culturing cells in an adherent culture is affected in serum-free medium, e.g. serum-free Expi293™ medium (discussed above).

According to one embodiment, the serum-free medium is supplemented with human serum albumin and/or insulin (discussed above).

According to one embodiment, culturing cells in an adherent culture is affected in medium comprising serum replacement.

As used herein the phrase "serum replacement" refers to a defined formulation, which substitutes the function of serum by providing cells with components needed for growth and viability. For example, a serum replacement can include Knockout Serum Replacement (described in PCT publication no. WO 1998/030679) consisting of e.g. vitamins, transferrin or substitutes, insulin or insulin substitutes, trace elements, collagen precursors, and albumin.

Various serum replacement formulations are known in the art and are commercially available, such as from Gibco-Invitrogen Corporation.

In cases where serum is used in the cell medium, such as to support the survival and growth of cells, or production of exosomes in adherent cell cultures (e.g. for expansion of genetically modified cells, discussed below), serum (i.e. an undefined mixture of different soluble proteins and growth factors) can be obtained from commercial sources, such as e.g. Fetal bovine serum (FBS, Biological Industries), Human AB Serum, Porcine serum, Horse serum, Rabbit serum and Goat serum, all of which are commercially available from e.g. Biological Industries.

According to some embodiments of the invention, the serum (e.g. FBS) in the culture medium is at most e.g. about 5% (v/v), e.g. about 10% (v/v), e.g. about 15% (v/v), e.g. about 20% (v/v), e.g. about 25% (v/v), e.g. about 30% (v/v).

In order to provide the cells with sufficient and constant supply of nutrients and growth factors while in the 2D culture, the culture medium can be replaced on a daily basis, or, at a pre-determined schedule such as every 2-7 days (e.g. 2-3 days). For example, replacement of the culture medium when the cells are grown in 2D culture and adhere to the plate can be performed by aspirating the medium from the culture dish and addition of fresh medium.

According to one embodiment, the cells are cultured is a suspension culture.

According to one embodiment, a suspension culture is a three-dimensional (3D) culture.

The term "3-dimensional culture" or "3D culture" refers to a cell culture with cells positioned relative to each other in three dimensions, i.e. width, depth and height.

As used herein the phrase "suspension culture" refers to a culture in which the cells are suspended in a medium rather than adhering to a surface.

Conditions for culturing the cells in suspension are devoid of substrate adherence, e.g., without adherence to an external substrate such as components of extracellular matrix, a glass microcarrier or beads.

According to some embodiments of the invention, at least some of the cells in the suspension culture adhere to the vessel surface.

Culturing cells in a suspension culture according to the method of some embodiments of the invention is affected by seeding the cells in a culture vessel at a cell density which promotes cell survival, proliferation and production of cell-derived particles. Typically, a plating density (or a seeding density) of between about $1 \times 10^6$ cells/ml to about $10 \times 10^6$ cells/ml is used.

According to one embodiment, culturing cells in a suspension culture is affected in serum-free medium, e.g. serum-free Expi293™ medium (discussed above).

According to one embodiment, the serum-free medium (e.g. Expi293™ medium) is not supplemented with human serum albumin and/or insulin (discussed above).

In order to provide the cells with sufficient and constant supply of nutrients and growth factors while in the suspension culture, the culture medium can be replaced on a daily basis, or, at a pre-determined schedule such as every 2-7 days (e.g. 2-3 days). For example, replacement of the culture medium can be performed by subjecting the cells in the suspension culture to centrifugation for about 1-10 minutes (e.g. 1-5 minutes, e.g. 3 minutes), at 1500 rpm and resuspension of the formed cell pellet in a fresh medium.

The culture vessel used for culturing the cells in suspension according to the method of some embodiments of the invention can be any tissue culture vessel (e.g. flask such as an Erlenmeyer flask). Such a determination is well within the skill of a person of skill in the art.

Furthermore, the suspension culture can be affected in a controlled culturing system (e.g. a computer-controlled culturing system) in which culture parameters such as temperature, agitation, pH, and $CO_2$ is automatically performed using a suitable device. Once the culture parameters are recorded, the system is set for automatic adjustment of culture parameters as needed for cells survival, proliferation and for production of cell-derived particles.

According to some embodiments of the invention, culturing of the suspension culture is affected under conditions comprising a dynamic suspension culture.

The phrase "dynamic suspension culture" refers to conditions in which the cells are subject to constant movement while in the suspension culture.

According to one embodiment, the dynamic suspension culture utilizes a Wave reactor, a stirred reactor or a spinner flask (e.g. glass spinner flask). According to one embodiment, the dynamic suspension culture utilizes a shaker incubator.

According to some embodiments of the invention, culturing of the suspension culture is affected under conditions comprising a static (i.e., non-dynamic) suspension culture.

The phrase "static suspension culture" refers to conditions in which the cells are subject to stationary conditions while in the suspension culture.

According to a specific embodiment, the culture medium and culturing conditions are capable of maintaining the cells for 2-50 passages, e.g. for 5-40 passages, e.g. for 5-30 passages, e.g. for 5-25 passages, e.g. for 5-20 passages, e.g. for 5-15 passages, e.g. for 5-10 passages, e.g. for 10-30 passages, e.g. for 10-20 passages, e.g. for 10-15 passages, e.g. for 15-30 passages, e.g. for 15-25 passages, e.g. for 15-20 passages, e.g. for 20-40 passages, e.g. for 20-30 passages, e.g. for 20-25 passages, e.g. for 30-40 passages, e.g. for 40-50 passages.

As used herein the term "passage" or "passaging" as used herein refers to splitting the cells in the culture vessel to 2 or more culture vessels, typically including addition of fresh culture medium. Passaging is typically done when the cells reach a certain density in culture.

In order to increase the number of cell-derived particles in a sample (e.g. cell culture), the sample may be treated by membrane extrusion, sonication, or other techniques well known in the art prior to isolation of particles therefrom.

According to one embodiment, the sample may be further purified or concentrated prior to use. For example, a heterogeneous population of cell-derived particles can be quantitated (i.e. total level of cell-derived particles in a sample), or a homogeneous population of cell-derived particles, such as a population of cell-derived particles with a particular size, with a particular marker profile, obtained from a particular type of biological sample (e.g. urine, serum, plasma, culture medium, etc.) or derived from a particular cell type (e.g. kidney cells or fibroblasts) can be isolated from a heterogeneous population of cell-derived particles and quantitated.

According to one embodiment, cell-derived particles are purified or concentrated from a biological sample using size exclusion chromatography, density gradient centrifugation, differential centrifugation, nanomembrane ultrafiltration, immunoabsorbent capture, affinity purification, microfluidic separation, or combinations thereof.

Size exclusion chromatography, such as gel permeation columns, centrifugation or density gradient centrifugation, and filtration methods can be used. For example, cell-derived particles can be isolated by differential centrifugation, anion exchange and/or gel permeation chromatography (as described e.g. in U.S. Pat. Nos. 6,899,863 and 6,812,023), sucrose density gradients, organelle electrophoresis (as described e.g. in U.S. Pat. No. 7,198,923), magnetic activated cell sorting (MACS), or with a nanomembrane ultrafiltration concentrator. Thus, various combinations of isolation or concentration methods can be used as known to one of skill in the art.

Sub-populations of cell-derived particles may be obtained using other properties of the cell-derived particles such as the presence of surface markers. Surface markers which may be used for fraction of cell-derived particles include but are not limited to cell type specific markers and MHC class II markers. MHC class II markers which have been associated with cell-derived particles include HLA DP, DQ and DR haplotypes. Other surface markers associated with cell-derived particles include, but are not limited to, CD9, CD81, CD63, CD82, CD37, CD53, or Rab-5b (Thery et al. Nat. Rev. Immunol. 2 (2002) 569-579; Valadi et al. Nat. Cell. Biol. 9 (2007) 654-659). Any method known in the art for measuring expression of a protein can be used, such as but not limited to, ELISA, Western blot analysis, FACS, and Immunohistochemical analysis.

Additionally or alternatively, sub-populations of cell-derived particles may be obtained using other properties of the cell-derived particles such as the expression of immune modulators, cytoskeletal proteins, membrane transport and fusion proteins, tetraspanins and/or proteins belonging to the heat-shock family. Additionally or alternatively, sub-populations of cell-derived particles may be obtained using other properties of the cell-derived particles such as the expression of membrane markers or components from the cells from which they were derived (e.g. kidney cells, fibroblasts, etc.). Any method known in the art for measuring expression or activity of a protein can be used, such as but not limited to, ELISA, Western blot analysis, FACS, Immunohistochemical analysis, In situ activity assay and In vitro activity assays.

Furthermore, the contents of the cell-derived particles may be extracted for characterization of cell-derived particles containing any of the above mentioned polypeptides.

According to a specific embodiment, cell-derived particles are selected for presentation of CD24 (e.g. human CD24 or a recombinant version thereof).

According to one embodiment, cell-derived particles are selected for expression of exosomal biomarkers, e.g. CD63, HSP70, CD81, CD9, CD82, CD37, CD53, or Rab-5b.

As an example, cell-derived particles having CD24 presentation on their surface may be isolated using antibody coated magnetic particles e.g. using Dynabeads*, superparamagnetic polystyrene beads which may be conjugated with anti-human CD24 antibody either directly to the bead surface or via a secondary linker (e.g. anti-mouse IgG). The beads may be between 1 and 4.5 μm in diameter. Accordingly, the antibody coated Dynabeads® may be added to a cell-derived particles sample (e.g. prepared as described above) and incubated at e.g. 2-8° C. or at room temperature from 5 minutes to overnight. Dynabeads® with bound cell-derived particles may then be collected using a magnet. The isolated, bead bound cell-derived particles may then be resuspended in an appropriate buffer such as phosphate buffered saline and used for analysis (qRT-PCR, sequencing, western blot, ELISA, flow cytometry, etc. as discussed below). Similar protocols may be used for any other surface marker for which an antibody or other specific ligand is available. Indirect binding methods such as those using biotin-avidin may also be used.

Determining the level of cell-derived particles (e.g. exosomes) in a sample can be performed using any method known in the art, e.g. by ELISA, using commercially available kits such as, for example, the ExoELISA® kit (System Biosciences, Mountain View, CA), magnetic activated cell sorting (MACS) or by FACS using an antigen or antigens which bind general cell-derived particles (e.g. exosome) markers, such as but not limited to, CD24, CD63, CD9, HSP70, CD81, CD82, CD37, CD53, or Rab-5b.

As mentioned, the cell-derived particles according to the present invention are devoid of intact cells.

As used herein, the phrase "substantially devoid of intact cells", when relating to the compositions of the present invention relates to a composition that comprises less than about 0.5%, 1%, 2%, 3%, 4%, 5%, 10%, 15%, or 20% intact cells per ml fluid sample. However, the biological sample may contain some cells or cell contents. The cells can be any cells which are derived from the subject or from the cell culture (as discussed in detail above).

According to one embodiment, the composition of the present invention which is substantially free of intact cells comprises no more than 1 intact cell per about 100 cell-derived particles, no more than 1 intact cell per about 1,000 cell-derived particles, no more than 1 intact cell per about 10,000 cell-derived particles, no more than 1 intact cell per about 100,000 cell-derived particles, no more than 1 intact cell per about 1 million cell-derived particles, no more than 1 intact cell per about 10 million cell-derived particles, no more than 1 intact cell per about 100 million cell-derived particles, no more than 1 intact cell per about 1 billion cell-derived particles, no more than 1 intact cell per about 10 billion cell-derived particles, or essentially does not comprise any intact cells.

Measuring the number of intact cells in a composition can be carried out using any method known in the art, such as by light microscopy or cell staining methods.

According to one embodiment, at least 10%, 20%, 30%, 40%, 50%, 60%, 70%, 80%, 90%, or 100% of the polypeptides (e.g. CD24) in the preparation are in the cell-derived particles.

According to a specific embodiment, at least 50% of the polypeptides (e.g. CD24) in the preparation are in the cell-derived particles.

According to one embodiment, the composition of cell-derived particles according to the present invention is animal origin-free (e.g. free of animal proteins such as bovine serum albumin).

According to one embodiment, once an isolated cell-derived particles sample has been prepared it can be preserved in saline.

According to one embodiment, cell-derived particles are used as a fresh sample.

According to one embodiment, cell-derived particles are cooled (e.g. in 4° C.) prior to use.

According to one embodiment, cell-derived particles are used as a non-fresh sample. For example, the cell-derived particles may be lyophilized (freeze-dried) and rehydrated (e.g. with sterile water or saline) prior to use. According to one embodiment, the cell-derived particles are cryopreserved prior to use.

Thus, according to one embodiment, once an isolated cell-derived particles sample has been prepared it can be stored, such as in a sample bank or freezer (e.g. at −70° C. to −80° C.) and retrieved for therapeutic purposes as necessary. Following thawing and prior to use, the cell-derived particles sample can be stored at 4° C. for 4-14 hours, e.g. for 12, 10, 9, 8, 7, 6 hours, e.g. for 8 hours. Alternatively, the cell-derived particles sample can be directly used without storing the sample (e.g. within 4-14 hours, e.g. within 12, 10, 9, 8, 7, 6 hours, e.g. within 8 hours, when stored at 4° C.).

As mentioned, the cell-derived particles are obtained from cells which do not naturally present CD24. Accordingly, in order to obtain cell-derived particles presenting heterologous CD24, the cells from which the cell-derived particles are obtained (e.g. secreted) may be modified to present CD24, or alternatively, the particles (e.g. exosomes) may be modified to heterologously present CD24. Such a step may be effected on a fresh batch of cells or cell-derived particles or on cells or cell-derived particles which were frozen and thawed.

According to one aspect of the invention, there is provided a method of producing cell-derived particles, the method comprising:

(a) modifying cells to present CD24;
(b) isolating cell-derived particles from a biological sample comprising the cells so as to obtain a preparation of the cell-derived particles substantially devoid of intact cells.

According to one embodiment, the method of producing cell-derived particles further comprises culturing the modified cells prior to isolating cell-derived particles therefrom.

According to one embodiment, the method is affected in vitro.

According to one embodiment, the method is affected ex vivo.

According to one embodiment, modifying comprises genetically engineering the cells (i.e. from which the cell-derived particles are obtained) to present CD24 on the cell membrane. The heterologous genetic material will then be incorporated into the cell-derived particles by the typical cellular machinery.

Any method known in the art for genetically modifying cells can be used in accordance with the present invention. For example, to express exogenous CD24 in mammalian cells, a polynucleotide sequence encoding a CD24 (e.g. as set forth in SEQ ID NO: 8) is preferably ligated into a nucleic acid construct suitable for mammalian cell expression. Such a nucleic acid construct typically includes a promoter sequence for directing transcription of the polynucleotide sequence in the cell in a constitutive or inducible manner.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). For example, the vector may include enhancer elements (e.g. that can stimulate transcription up to 1,000 fold from linked homologous or heterologous promoters), polyadenylation sequences (e.g. that can increase the efficiency of CD24 mRNA translation), a eukaryotic replicon (e.g. which enables the vector to be amplifiable in eukaryotic cells using an appropriate selectable marker), and/or additional polynucleotide sequences (e.g. that allow, for example, the translation of several proteins from a single mRNA, such as an internal ribosome entry site (IRES) and sequences for genomic integration of the promoter-chimeric polypeptide). In addition, a typical cloning vectors may also contain a transcription and translation initiation sequence, transcription and translation terminator and a polyadenylation signal. By way of example, such constructs will typically include a 5' long terminal repeats (LTRs), a tRNA binding site, a packaging signal, an origin of second-strand DNA synthesis, and a 3' LTRs or a portion thereof.

Examples for mammalian expression vectors include, but are not limited to, pCDNA4, pcDNA4/TO, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, pCI, pMbac, pPbac, pBK-RSV, pBK-CMV, pTRES, which are commercially available from e.g. Thermo Fisher Scientific, Invitrogen, Promega, Strategene, Clontech, and their derivatives. Non-viral vectors that can be used include e.g. cationic lipids, polylysine, and dendrimers.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 19861 and include, for example, stable or transient transfection, lipofection, electroporation and infection with recombinant viral vectors, such as adenovirus, lentivirus, retrovirus, Herpes simplex I virus, or adeno-associated virus (AAV). In addition, see U.S. Pat. Nos. 5,464,764 and 5,487,992 for positive-negative selection methods.

According to one embodiment, to express exogenous CD24 in mammalian cells an expression vector (e.g. plasmid DNA) carrying the CD24 gene or fragment thereof is transfected into the cells by lipofection (e.g. using for example Lipofectamine®, commercially available from e.g. Invitrogen). Other useful lipids for lipid-mediated transfer of the gene include, for example, DOTMA, DOPE, and DC-Chol [Tonkinson et al., Cancer Investigation, 14(1): 54-65 (1996)].

The above described methods can be further applied to genetically engineer cells (i.e. from which the cell-derived particles are obtained) to express additional peptides, polypeptides or heterologous moieties (e.g. binding agents e.g. for specific targeting of a target cell, as discussed below) which may be beneficial for therapeutics. Such determinations are well within the skill of one of skill in the art.

According to another embodiment of the invention, the cell-derived particles are obtained from cells which are chemically manipulated to present CD24 or recombinant versions thereof (e.g. genetically non-modified cells).

Any chemical modification of cells known in the art for eliciting membrane expression can be used according to the present teachings, including but not limited to, click chemistry. According to click chemistry, conjugation of a polypeptide to a cell surface is performed by a reaction between a pair of functional groups that rapidly and selective react (i.e., "click") with each other. In some embodiments, the click chemistry can be performed under mild, aqueous conditions. Such methods are described in U.S. Patent Application No. 2021/015896.

A variety of reactions that fulfill the criteria for click chemistry are known in the field, and one skilled in the art could use any one of a number of published methodologies [see, e.g., Hein et al., Pharm Res 25(10):2216-2230 (2008)]. A wide range of commercially available reagents for click chemistry could be used, such as those from Sigma Aldrich, Jena Bioscience, or Lumiprobe.

Following modification of the cells (e.g. human or animal cells) to express the heterologous material (e.g. to present CD24 on the cell membrane), the cells are typically assessed for expression of CD24. Methods of measuring expression of CD24 proteins on a cell are well known in the art and include, e.g. ELISA, Western blot analysis, and Flow cytometry assay (e.g. FACS).

The modified cells are then cultured for an ample amount of time to allow cell expansion and to produce cell-derived particles (e.g. for 1, 2, 3, 4, 5, 6, 12, 24, 48, 72, 96 hours, for several days e.g. 1, 2, 3, 4, 5, 6, 7, 8, 9, 10, 12, 14, 21 or 30 days, or for several weeks e.g. 1, 2, 3, 4, 5, 6, 7, 8, 10, 12 or 14 weeks) prior to isolating of the cell-derived particles (as discussed in detail above).

As mentioned above, the cell derived particles may be obtained from a culture medium of various volumes (e.g. 0.1 mL-1000 L). According to one embodiment, a culture medium comprises about $1\times10^4$-$1\times10^{30}$ particles/1 L, about $1\times10^6$-$1\times10^{28}$ particles/1 L, about $1\times10^8$-$1\times10^{26}$ particles/1 L, about $1\times10^{10}$-$1\times10^{24}$ particles/1 L, about $1\times10^{10}$-$1\times10^{16}$ particles/1 L, about $1\times10^{10}$-$1\times10^{14}$ particles/1 L, about $1\times10^{10}$-$1\times10^{12}$ particles/1 L, about $1\times10^{11}$-$1\times10^{14}$ particles/1 L, about $1\times10^{12}$-$1\times10^{22}$ particles/1 L, about $1\times10^{12}$-$1\times10^{16}$ particles/1 L, about $1\times10^{12}$-$1\times10^{14}$ particles/1 L, about $1\times10^{12}$ $1\times10^{13}$ particles/1 L, about $1\times10^{14}$-$1\times10^{20}$ particles/1 L, or about $1\times10^{16}$-$1\times10^{18}$ particles/1 L.

According to one embodiment, a culture medium comprises at least about $1\times10^6$ particles/1 L.

According to one embodiment, a culture medium comprises at least about $1\times10^8$ particles/1 L.

According to one embodiment, a culture medium comprises at least about $1\times10^{10}$ particles/1 L.

According to one embodiment, a culture medium comprises at least about $1\times10^{12}$ particles/1 L.

According to one embodiment, a culture medium comprises at least about $1\times10^{14}$ particles/1 L.

According to one embodiment, a culture medium comprises at least about $1\times10^{16}$ particles/1 L.

According to one embodiment, a culture medium comprises at least about $1\times10^{18}$ particles/1 L.

According to one embodiment, a culture medium comprises at least about $1\times10^{20}$ particles/1 L.

According to one embodiment, a culture medium comprises at least about $1\times10^{25}$ particles/1 L.

According to one embodiment, culturing the modified cells can be effected in two-dimensional (2D) cultures or three-dimensional (3D) cultures, as discussed above.

Moreover, culturing can be effected in any culture medium, e.g. defined culture medium, such as a serum-free medium, as discussed above.

According to one embodiment, when the cells are cultured in a suspension culture, the preparation of the cell-derived particles comprises at least 2-10 times more cell derived particles as compared to cells cultured in a 2D culture. Accordingly, smaller volumes of culture medium can be used in 3D cultures to produce the same or larger amounts of cell derived particles compared to 2D cultures.

According to one embodiment, when the cells are cultured in a suspension culture, the preparation of the cell-derived particles comprises at least 2-7 times more cell derived particles as compared to cells cultured in a 2D culture.

According to one embodiment, when the cells are cultured in a suspension culture, the preparation of the cell-derived particles comprises at least 2-5 times more cell derived particles as compared to cells cultured in a 2D culture.

According to one embodiment, when the cells are cultured in a suspension culture, the preparation of the cell-derived particles comprises at least about 2 times more cell derived particles as compared to cells cultured in a 2D culture.

According to one embodiment, when the cells are cultured in a suspension culture, the preparation of the cell-derived particles comprises at least about 3 times more cell derived particles as compared to cells cultured in a 2D culture.

According to one embodiment, when the cells are cultured in a suspension culture, the preparation of the cell-derived particles comprises at least about 4 times more cell derived particles as compared to cells cultured in a 2D culture.

According to one embodiment, when the cells are cultured in a suspension culture, the preparation of the cell-derived particles comprises at least about 5 times more cell derived particles as compared to cells cultured in a 2D culture.

According to a specific embodiment, cells modified to present CD24 are cultured in 2D cultures comprising, for example, DMEM medium supplemented with 5-10% serum, for an ample amount of time to allow cell expansion (e.g. for 12, 24, 48, 72, 96 hours). Then the expanded population of cells are washed, the medium is replaced to serum-free medium (e.g. Expi293™ medium) and the cells are cultured in 2D cultures or in 3D cultures for an ample amount of time to allow production of cell-derived particles (e.g. for 12, 24, 48, 72, 96 hours, for several days, e.g. 1, 2, 3, 4, 5, 6, 7, 8, 9, 10 days or more) prior to isolation of the cell-derived particles (as discussed in detail above). In cases where the cells are cultured in 2D cultures, the culture medium may be supplemented with insulin and human serum albumin, or with serum replacement, as discussed above.

According to another embodiment, the exogenous material (e.g. CD24) can be introduced directly into cell-derived particles (e.g. exosomes) by a various techniques known in the art. For example, cell-derived particles (e.g. obtained from any cell type which does not naturally express CD24) may be loaded by the use of a transfection reagent or using a chemical modification (as discussed above). Despite the small size of cell-derived particles (e.g. exosomes are typically between 30-200 nm), previous publications have illustrated that it is possible to load the cell-derived particles with the exogenous material (see for example European Patent No. EP2419144). For example, conventional transfection reagent can be used for transfection of cell-derived particles with CD24, such as but not limited to, cationic liposomes.

The cell-derived particles may be modified to target a desired cell or tissue (e.g. lung tissue). This targeting is achieved by expressing on the surface of the cell-derived particles a heterologous moiety (also referred to as binding agent) which binds to a cell surface moiety expressed on the surface of the cell to be targeted. For example, the cell-derived particles can be targeted to particular cell types or tissues by expressing on their surface a heterologous moiety such as a protein, a peptide or a glycolipid molecule. For example, suitable peptides are those which bind to cell surface moieties such as receptors or their ligands found on the cell surface of the cell to be targeted. Examples of suitable heterologous moieties are short peptides, scFv and complete proteins, so long as the binding agent can be expressed on the surface of the cell-derived particles and does not interfere with expression of the CD24.

According to some embodiments of the invention, the cell-derived particles are loaded with an additional therapeutic moiety such as a drug, e.g., an anti-viral agent, anti-inflammatory agent or a toxic moiety (e.g. such a small molecule, e.g., therapeutic drug for the treatment of Coronavirus infection, as discussed below) or with immune modulators.

Determination that the cell-derived particles comprise specific components (e.g. CD24, or additional components e.g. immune modulators or additional therapeutic moiety) can be carried out using any method known in the art, e.g. by Western blot, ELISA, FACS, MACS, RIA, Immunohistochemical analysis, In situ activity assay, and In vitro activity assays. Likewise, determination that the cell-derived particles comprise a heterologous moiety (e.g. binding agent), a cytotoxic moiety or a toxic moiety, can be carried out using any method known in the art.

According to one embodiment, the cell-derived particles presenting heterologous CD24 of the invention comprise the product termed Exo-CD24.

According to a specific embodiment, the preparation of the cell-derived particles comprises $1 \times 10^3$-$1 \times 10^{30}$ particles (e.g. Exo-CD24) per batch of production (e.g. about $1 \times 10^5$-$1 \times 10^{2}$, about $1 \times 10^{10}$-$1 \times 10^{20}$, about $1 \times 10^{12}$-$1 \times 10^{16}$ or about $1 \times 10^{12}$-$1 \times 10^{13}$ particles per batch of production).

According to one embodiment, the preparation of the cell-derived particles comprises $1 \times 10^3$-$1 \times 10^{30}$ particles per liter (e.g. Exo-CD24).

According to one embodiment, the preparation of the cell-derived particles comprises $1 \times 10^3$-$1 \times 10^{20}$ particles per liter (e.g. Exo-CD24).

According to one embodiment, the preparation of the cell-derived particles comprises $1 \times 10^5$-$1 \times 10^{15}$ particles per liter (e.g. Exo-CD24).

According to one embodiment, the preparation of the cell-derived particles comprises $1 \times 10^6$-$1 \times 10^{13}$ particles per liter (e.g. Exo-CD24).

According to one embodiment, the preparation of the cell-derived particles comprises $1 \times 10^6$-$1 \times 10^{12}$ particles per liter (e.g. Exo-CD24).

According to one embodiment, the preparation of the cell-derived particles comprises $1 \times 10^7$-$1 \times 10^{10}$ particles per liter (e.g. Exo-CD24).

According to one embodiment, the preparation of the cell-derived particles comprises $1 \times 10^7$-$1 \times 10^9$ particles per liter (e.g. Exo-CD24).

According to one embodiment, the preparation of the cell-derived particles comprises at least about 1000, 2000, 5000, 10,000, 50,000, 100,000, 500,000, 750,000, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, $1 \times 10^{13}$, $5 \times 10^{13}$ or more cell-derived particles per liter (e.g. Exo-CD24).

According to a specific embodiment, the preparation of the cell-derived particles comprises at least about $1 \times 10^5$ cell derived particles per liter (e.g. Exo-CD24).

According to a specific embodiment, the preparation of the cell-derived particles comprises at least about $1 \times 10^6$ cell derived particles per liter (e.g. Exo-CD24).

According to a specific embodiment, the preparation of the cell-derived particles comprises at least about $1 \times 10^7$ cell derived particles per liter (e.g. Exo-CD24).

According to a specific embodiment, the preparation of the cell-derived particles comprises at least about $1 \times 10^8$ cell derived particles per liter (e.g. Exo-CD24).

According to one embodiment, there is provided a method of treating or preventing a cytokine storm syndrome in a subject in need thereof, the method comprising administering to the subject a therapeutically effective amount of the composition of some embodiments of the invention, thereby treating or preventing the cytokine storm syndrome in the subject.

According to one embodiment, there is provided a composition of some embodiments of the invention for use in treating or preventing a cytokine storm syndrome in a subject in need thereof.

The term "treating" refers to inhibiting or arresting the development of a pathology and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology (as further discussed below).

The term "treating" also includes preventing the development of a pathology from occurring in a subject who may be at risk for the pathology, but has not yet been diagnosed as having the pathology. It will be appreciated that the treating may be performed alone or in conjunction with other therapies.

As used herein, the terms "subject" or "subject in need thereof" include animals, preferably mammals, including human beings, at any age or of any gender which may suffer from a pathology or who is at risk of developing the pathology (as discussed below).

The term "cytokine storm syndrome", also referred to as "cytokine storm", "cytokine release syndrome" or "inflammatory cascade", as used herein refers to the systemic inflammatory condition involving elevated levels of circulating cytokines, causing immune-cell hyperactivation, and typically leading to multisystem organ dysfunction and/or failure which can lead to death. Often, a cytokine storm is referred to as being part of a sequence or cascade because one pro-inflammatory cytokine typically leads to the production of multiple other pro-inflammatory cytokines that can reinforce and amplify the immune response.

Diagnosis of cytokine storm syndrome can be carried out using any method known in the art, such as by a subject's physical evaluation, blood tests and imaging-based evaluation. Early symptoms of cytokine storm may include, for example, high fever, fatigue, anorexia, headache, rash, diarrhea, arthralgia, myalgia, and neuropsychiatric symptoms, or any combination thereof. However, early symptoms may quickly (e.g. within hours or within days) turn into more severe and life-threating symptoms. Accordingly, subjects having cytokine storm syndrome typically have respiratory symptoms, including cough and tachypnea that can progress to acute respiratory distress syndrome (ARDS), with hypoxemia that may require mechanical ventilation. Severe symptoms of cytokine storm may include, for example, uncontrollable hemorrhaging, severe metabolism dysregulation, hypotension, cardiomyopathy, tachycardia, dyspnea, fever, ischemia or insufficient tissue perfusion, kidney failure, liver injury acute liver injury or cholestasis, multisystem organ failure, or any combination thereof. Blood tests typically illustrate hyperinflammation as measured, for example, by C-reactive protein (CRP) levels, and blood-count abnormalities, such as leukocytosis, leukopenia, anemia, thrombocytopenia, and elevated ferritin and d-dimer levels.

According to one embodiment, cytokine storm syndrome is typically associated with elevated serum levels of at least 40%, at least 50%, at least 60%, at least 70%, e.g. at least 50% (compared to basal state) of one or more cytokine, such as but not limited to, IFN-α, IFN-γ, TNF-α, IL-1 (e.g. IL-1α, IL-1β), IL-2, IL-5, IL-6, IL-7, IL-12, IL-178, IL-18, IL-21, IL-17, IL-33 and HMGB-1, or chemokine, such as but not limited to, IL-8, MIG, IP-10, MCP-1 (e.g., MIP-1α, MIP-1β), and BLC. Assessment of cytokine levels can be carried out using any method known in the art, such as but not limited to, by ELISA or immunoassay.

According to one embodiment, the subject may be a subject at any stage of the cytokine storm, e.g. a subject showing preliminary signs of a cytokine storm (e.g. elevated CRP levels, elevated cytokine levels, having early symptoms of cytokine storm as discussed above), a subject showing mild signs of cytokine storm (e.g. showing signs of organ dysfunction, requiring oxygen, blood tests showing hyperinflammation), a subject having severe signs of cytokine storm (e.g. requiring mechanical ventilation, hemorrhaging, having multisystem organ dysfunction and/or failure) or a subject after the severe stage of a cytokine storm.

Cytokine storms can be triggered by various pathogens, therapies, cancers, autoimmune and autoinflammatory conditions, and monogenic disorders, as further discussed below.

According to one embodiment, the cytokine storm syndrome is associated with an infectious disease.

According to a specific embodiment, the cytokine storm is viral-induced.

Viral infectious diseases commonly associated with a cytokine storm include, but at not limited to, malaria, avian influenza, smallpox, pandemic influenza, adult respiratory distress syndrome (ARDS), severe acute respiratory syndrome (SARS). According to one embodiment, the infectious agents include, but are not limited to, Ebola, Marburg, Crimean-Congo hemorrhagic fever (CCHF), South American hemorrhagic fever, dengue, yellow fever, Rift Valley fever, Omsk hemorrhagic fever virus, Kyasanur Forest, Junin, Machupo, Sabia, Guanarito, Garissa, Ilesha, or Lassa fever viruses. According to one embodiment, the viral infectious agents include, but are not limited to, coronavirus, rhinovirus, paramyxoviridae, Orthomyxoviridae, adenovirus, parainfluenza virus, metapneumovirus, respiratory syncytial virus, influenza virus, Epstein-Barr virus, cytomegalovirus, flavivirus, variola and hantavirus.

According to one embodiment, the cytokine storm is induced by a virus causing a respiratory infection, such as but not limited to, influenza virus or coronavirus.

According to one embodiment, the cytokine storm is induced by a coronavirus.

Exemplary coronaviruses include, but are not limited to, severe acute respiratory syndrome coronavirus 2 (SARS-CoV-2), a Middle East respiratory syndrome coronavirus (MERS-CoV) and a severe acute respiratory syndrome coronavirus (SARS-CoV). Additional examples are provided herein below.

According to one embodiment, the cytokine storm is induced by an influenza virus. Exemplary influenza viruses include, but are not limited to, H1N1 (Spanish influenza) and H5N1 (Avian flu).

According to one embodiment, the cytokine storm is bacterial-induced. Exemplary bacterial pathogens which can induce a cytokine storm include, but are not limited to, *streptococcus* species (e.g. *streptococcus* group A) and *Staphylococcus aureus*.

According to one embodiment, the cytokine storm syndrome is associated with a medical condition. Disease conditions commonly associated with a cytokine storm include, but at not limited to, COVID-19, Acute respiratory distress syndrome (ARDS), an autoimmune disease, antibody-associated cytokine storm, anaphylaxis, adoptive cell therapy-associated cytokine storm, TNF-inhibition associated cytokine storm, distributive shock, sepsis, systemic inflammatory response syndrome (SIRS), cachexia, septic shock syndrome, traumatic brain injury (e.g., cerebral cytokine storm), graft versus host disease (GVHD), inflammatory bowel disease (IBD), Acute respiratory distress syndrome (ARDS), Acute Respiratory Distress Syndrome secondary to drug use or inhalation of toxins, Chronic obstructive pulmonary disease (COPD), Cystic fibrosis (CF), asthma, acute pancreatitis, severe burns or trauma, wound healing, Ebola virus disease (EVD), avian influenza, Spanish influenza, Hemophagocytic lymphohistiocytosis (HLH), Epstein-Barr virus-related hemophagocytic lymphohistiocytosis, familiar hemophagocytic lymphohistiocytosis, systemic or non-systemic juvenile idiopathic arthritis-associated macrophage activation syndrome and NLRC4 macrophage activation syndrome.

According to one embodiment, the cytokine storm syndrome is lung-associated.

According to one embodiment, the cytokine storm syndrome is airway-associated.

According to one embodiment, the cytokine storm syndrome is associated with acute respiratory distress syndrome (ARDS), asthma, Chronic obstructive pulmonary disease (COPD), Cystic fibrosis (CF), interstitial lung disease and Bronchiolitis obliterans organizing pneumonia (BOOP).

According to one embodiment, the cytokine storm syndrome is associated with an autoimmune or autoinflammatory disease or condition. Exemplary autoimmune and autoinflammatory diseases or conditions which are associated with cytokine storm include, but are not limited to, rheumatoid arthritis (RA), lupus (SLE), atherosclerosis, multiple sclerosis (MS), hashimoto disease, type I diabetes, autoimmune pancreatitis, graft-versus-host disease (GVHD), sepsis, Ebola, avian influenza, smallpox, systemic inflammatory response syndrome (SIRS), hemophagocytic lymphohistiocytosis, Crohn's and ulcerative colitis, familial Mediterranean fever (FMF), TNF receptor-associated periodic syndrome (TRAPS), hyperimmunoglobulinemia D with periodic fever syndrome (HIDS), familial cold autoinflammatory syndrome (FCAS), the Muckle-Wells syndrome (MWS), neonatal-onset multisystem inflammatory disease (NOMID), deficiency of ADA2 (DADA2), NLRC4 inflammasomopathies, X-linked lymphoproliferative type 2 disorder (XLP), the Takenouchi-Kosaki syndrome, and the Wiskott-Aldrich syndrome (WAS).

According to one embodiment, the cytokine storm syndrome is associated with a monogenic disorder. An exemplary monogenic disorder which is associated with cytokine storm includes, but is not limited to, cystic fibrosis (CF). Moreover, in patients with primary Hemophagocytic lymphohistiocytosis (HLH), autosomal recessive monogenic abnormalities in granule-mediated cytotoxicity, e.g. PRF1, UNC13D, STXBP1, RAB27A, STX11, SH2D1A, XIAP, and NLRC4, lead to cytokine storm.

According to one embodiment, the cytokine storm syndrome is associated with a medical treatment. Exemplary medical treatments which are associated with cytokine storm include, but are not limited to, treatment with adoptive cell therapy, e.g. activated immune cells, e.g., IL-2 activated T cells, Chimeric Antigen Receptor (CAR) T cells; TNF-Inhibition treatment.

Additional information relating to cytokine storm syndrome, its causes, diseases associated therewith and methods of diagnosis thereof are discussed in Fajgenbaum and June, N Engl J Med (2020) 383:2255-2273, incorporated herein by reference.

According to one embodiment, the cell-derived particles presenting heterologous CD24 of some embodiments of the invention are able to reduce cytokine storm or its harmful effects in a subject by about 10%, 20%, 30%, 40%, 50%, 60%, 70%, 80%, 90% or by 100% as compared to a subject not being treated.

Any of the above described methods of assessing cytokine storm syndrome can be utilized for assessing reduction or improvement of symptoms associated with the cytokine storm.

According to one embodiment, there is provided a method of treating or preventing a coronavirus infection in a subject in need thereof, the method comprising administering to the subject a therapeutically effective amount of the composition of some embodiments of the invention, thereby treating the coronavirus infection in the subject.

According to one embodiment, there is provided a composition of some embodiments of the invention for use in treating or preventing a coronavirus infection in a subject in need thereof.

As used herein "Coronavirus" refers to enveloped single-stranded RNA viruses that belong to the family Coronaviridae and the order Nidovirales.

Coronaviruses include, but are not limited to, the human coronavirus (HCoV, which typically cause common cold including e.g. HCoV-229E, HCoV-OC43, HCoV-NL63, HCoV-HKU1), transmissible gastroenteritis virus (TGEV), murine hepatitis virus (MHV), bovine coronavirus (BCV), feline infectious peritonitis virus (FIPV), severe acute respiratory syndrome coronavirus (SARS-CoV), Middle East respiratory syndrome coronavirus (MERS-CoV) or severe acute respiratory syndrome coronavirus 2 (SARS-CoV-2).

According to a specific embodiment, the human coronavirus is SARS-CoV-2 (i.e. causing COVID-19 disease).

According to a specific embodiment, the human coronavirus is SARS-CoV.

Methods of determining the presence of a coronavirus infection in a subject are well known in the art and are either based on serology, protein markers, electron microscopy or nucleic acid assays including, but not limited to, PCR and sequencing.

According to one embodiment, the subject may be a healthy subject or a subject at any stage of the infection, e.g. a subject being asymptomatic for the infection, a subject showing preliminary signs of the infection, a subject being in a symptomatic stage of the infection, or a subject after the symptomatic stage of the infection.

According to one embodiment, the subject is afflicted with the coronavirus infection, yet does not necessarily show symptoms of the infection (i.e. is an asymptomatic carrier). The subject may be contagious or not contagious.

Symptoms associated with Coronavirus infection (e.g. with SARS-CoV-2) include, for example, fever, chills (with or without repeated shaking), cough, fatigue, runny or stuffy nose, sore throat, nausea, loss of smell and/or taste, shortness of breath, inflammation in the lung, alveolar damage, diarrhea, organ failure, pneumonia and/or septic shock.

According to one embodiment, the symptoms may be present during the primary infection. According to one embodiment, the symptoms may persist for a prolonged period of time, e.g. for several weeks or months following the infection (i.e. secondary effects of the viral infection). For example, the secondary effects of Coronavirus infection (e.g. SARS-CoV-2), may include, but are not limited to, fatigue, shortness of breath, cough, joint pain, muscle pain, chest pain, depression, heart palpitations and pulmonary fibrosis.

According to one embodiment, the secondary effects of Coronavirus infection include Multisystem Inflammatory Syndrome in Children (MIS-C), e.g. inflammation of different organs including e.g. heart, lungs, kidneys, brain, skin, eyes, or gastrointestinal organs.

According to a specific embodiment, the subject is selected as being high risk for the Coronavirus (e.g. for SARS-CoV-2) or for complications associated therewith (e.g. for pulmonary fibrosis or ARDS) prior to treatment (e.g. a diabetes subject, an immunocompromised subject, a subject suffering from a lung condition such as e.g. COPD, a subject suffering from a heart condition, a cancer patient, etc.).

According to a specific embodiment, the subject is selected as being positive for Coronavirus (e.g. for SARS-CoV-2) prior to treatment.

According to a specific embodiment, when the subject is diagnosed with SARS-CoV-2 the subject exhibits moderate severity of the disease according to at least one clinical parameter and one laboratory parameter as follows:
  a. Clinical and Imaging-based evaluation
    i. Respiratory rate >23/min and <30/min
    ii. $SpO_2$ at room air ≤94% and >90%
    iii. Bilateral pulmonary infiltrates >50% within 24-48 hours or a severe deterioration compared to imaging at admission
  b. Evidence of an exacerbated inflammatory process
    i. LDH score >450 u/L
    ii. CRP >100 mg/L
    iii. Ferritin >1650 ng/ml
    iv. Lymphopenia <800 cells/mm3
    v. D-dimer >1 mcg/mL According to one embodiment, the cell-derived particles presenting heterologous CD24 of some embodiments of the invention are able to treat coronavirus infection or alleviate the symptoms associated therewith in a subject by about 10%, 20%, 30%, 40%, 50%, 60%, 70%, 80%, 90% or by 100% as compared to a subject not being treated.

Any of the above-described methods of assessing coronavirus infection can be utilized for assessing reduction or improvement of symptoms associated with the coronavirus infection.

According to one embodiment, there is provided a method of treating or preventing a tissue injury associated with inflammation in a subject in need thereof, the method comprising administering to the subject a therapeutically effective amount of the composition of some embodiments of the invention, thereby treating or preventing the tissue injury associated with the inflammation in the subject.

According to one embodiment, there is provided a composition of some embodiments of the invention for use in treating or preventing tissue injury associated with inflammation in a subject in need thereof.

The term "tissue injury associated with inflammation" as used herein refers to any damage to a tissue including muscle tissue, nerve tissue, epithelial tissue and connective tissue as a result of an inflammatory response.

As used herein the term "inflammation", also referred to as "inflammatory response", refers to the response of the immune system to an infection (e.g. pathogen), to an autoimmune disorder, to an injury or trauma (e.g. mechanical ventilation, myocardial infarction) or to irritation (e.g. exposure to industrial chemicals or polluted air) in a body tissue. Inflammation may generally be characterized as causing a tissue to have one or more of the following characteristics: redness, heat, swelling, pain and dysfunction. Though inflammation is an essential component of innate immunity, if left untreated, it may result in severe and irreparable tissue damage.

Any method known in the art can be used to diagnose an inflammation, including but not limited to, serum protein electrophoresis (SPE), C-reactive protein (CRP) levels, erythrocyte sedimentation rate (ESR) and plasma viscosity. Furthermore, any method known in the art can be used for evaluation of tissue damage, such as blood tests assessing, for example, liver enzymes, heart enzymes, kidney enzymes, and imaging-based evaluation (e.g. ultrasound, MRI, CT scan).

According to one embodiment, the tissue damage is a result of an acute inflammation. Acute inflammation is typically a short-term process which may last for a few minutes to a few days.

According to one embodiment, the tissue damage is a result of a chronic inflammation. Chronic inflammation is typically regarded as low levels of inflammation that persist through time (e.g. for several weeks, months or years).

According to one embodiment, the inflammation is associated with damage-associated molecular patterns (DAMPs). DAMP molecules are endogenous "inflammatory mediators" which regulate immune responses and inflammation. Exemplary DAMP molecules include, but are not limited to, high mobility group box 1 protein (HMGB-1), heat-shock proteins (HSPs), uric acid, altered matrix proteins, and S100 proteins (e.g. S100A8, S100A9, and S100A12). DAMP molecules are typically released from activated or necrotic cells and represent danger signals that mediate inflammatory responses through the receptor for advanced glycation end-products (RAGE, also known as AGER) and Toll-like receptors (TLR).

According to one embodiment, the tissue injury associated with inflammation is lung-associated.

According to one embodiment, the tissue injury associated with inflammation is associated with a medical condition selected from the group consisting of Acute respiratory distress syndrome (ARDS), Chronic obstructive pulmonary disease (COPD), Cystic fibrosis (CF), inflammatory bowel disease (IBD), Crohn's disease, tissue reperfusion injury following myocardial infarction, ischemic reperfusion injury, rheumatoid arthritis (RA), atherosclerosis, type 2 diabetes, systemic lupus erythematosus (SLE), glomerulonephritis, chronic wound, multiple sclerosis (MS) and Age-Related Macular degeneration (ARMD).

Administration of the cell-derived particles presenting heterologous CD24 according to some embodiments of the invention, may at least partially prevent, reduce or inhibit one or more of the pathological complications associated with tissue damage associated with inflammation.

Complications associated with inflammation that may be influenced according to some embodiments include activation of complement proteins, deposition of activated complement proteins and the membrane attack complex in tissues, cellular and tissue damage caused by generation of reactive oxygen species and other radicals, and deposition of C-reactive protein at sites of inflammation. Reduction in the incidence and/or severity of one or more of the aforementioned complications may reduce the amount of tissue damage occurring at a site of inflammation.

According to one embodiment, the cell-derived particles presenting heterologous CD24 of some embodiments of the invention are able to reduce tissue damage associated with inflammation by about 10%, 20%, 30%, 40%, 50%, 60%, 70%, 80%, 90% or by 100% as compared to the tissue damage in a subject in the absence of treatment.

Any of the above-described methods of assessing tissue damage can be utilized for assessing reduction or improvement of tissue damage associated with inflammation.

For in vivo therapy, the cell-derived particles presenting heterologous CD24 (e.g. Exo-CD24) or compositions comprising same can be administered to the subject per se or as part of a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the cell-derived particles presenting heterologous CD24 accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include systemic, oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, intratumoral or intraocular injections.

According to one embodiment, administering comprises a route selected from the group consisting of intravenous, intra-arterial, intratumoral, subcutaneous, intramuscular, transdermal and intraperitoneal.

According to a specific embodiment, the composition is for inhalation mode of administration.

According to a specific embodiment, the composition is for intranasal administration.

According to a specific embodiment, the composition is for oral administration.

According to a specific embodiment, the composition is for local injection.

According to a specific embodiment, the composition is for systemic administration.

According to a specific embodiment, the composition is for intravenous administration.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically.

Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

According to one embodiment, the composition (e.g. for nasal inhalation) is in a dry formulation.

According to one embodiment, the composition (e.g. for nasal inhalation) is in a liquid formulation.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g. cell-derived particles presenting heterologous CD24, e.g. Exo-CD24) effective to alleviate or ameliorate symptoms of a disorder (e.g., viral infection) or prolong the survival of the subject being treated.

According to an embodiment of the present invention, an effective amount of the cell-derived particles presenting heterologous CD24 (e.g. Exo-CD24) of some embodiments of the invention, is an amount selected to treat or prevent cytokine storm syndrome or the harmful effects associated therewith.

According to an embodiment of the present invention, an effective amount of the cell-derived particles presenting heterologous CD24 (e.g. Exo-CD24) of some embodiments of the invention, is an amount selected to treat or prevent Coronavirus infection.

According to an embodiment of the present invention, an effective amount of the cell-derived particles presenting heterologous CD24 (e.g. Exo-CD24) of some embodiments of the invention, is an amount selected to treat or prevent tissue injury associated with inflammation.

According to an embodiment of the present invention, an effective amount of the cell-derived particles presenting heterologous CD24 (e.g. Exo-CD24) of some embodiments of the invention is $1\times10^5$-$1\times10^{20}$ particles per administration.

According to an embodiment of the present invention, an effective amount of the cell-derived particles presenting heterologous CD24 (e.g. Exo-CD24) of some embodiments of the invention is $1\times10^5$-$1\times10^{15}$ particles per administration.

According to an embodiment of the present invention, an effective amount of the cell-derived particles presenting heterologous CD24 (e.g. Exo-CD24) of some embodiments of the invention is $1\times10^6$-$1\times10^{13}$ particles per administration.

According to an embodiment of the present invention, an effective amount of the cell-derived particles presenting heterologous CD24 (e.g. Exo-CD24) of some embodiments of the invention is $1\times10^6$-$1\times10^{12}$ particles per administration.

According to an embodiment of the present invention, an effective amount of the cell-derived particles presenting heterologous CD24 (e.g. Exo-CD24) of some embodiments of the invention is $1\times10^7$-$1\times10^{10}$ particles per administration.

According to an embodiment of the present invention, an effective amount of the cell-derived particles presenting heterologous CD24 (e.g. Exo-CD24) of some embodiments of the invention is $1\times10^7$-$1\times10^9$ particles per administration.

According to an embodiment of the present invention, an effective amount of the cell-derived particles presenting heterologous CD24 (e.g. Exo-CD24) of some embodiments of the invention is $1\times10^7$ particles per administration.

According to an embodiment of the present invention, an effective amount of the cell-derived particles presenting heterologous CD24 (e.g. Exo-CD24) of some embodiments of the invention is $1\times10^8$ particles per administration.

According to an embodiment of the present invention, an effective amount of the cell-derived particles presenting heterologous CD24 (e.g. Exo-CD24) of some embodiments of the invention is $1\times10^9$ particles per administration.

According to an embodiment of the present invention, an effective amount of the cell-derived particles presenting heterologous CD24 (e.g. Exo-CD24) of some embodiments of the invention is $1\times10^{10}$ particles per administration.

According to an embodiment of the present invention, an effective amount of the cell-derived particles presenting heterologous CD24 (e.g. Exo-CD24) of some embodiments of the invention is $1\times10^{11}$ particles per administration.

According to an embodiment of the present invention, an effective amount of the cell-derived particles presenting heterologous CD24 (e.g. Exo-CD24) of some embodiments of the invention is $1\times10^{12}$ particles per administration.

Determination of a therapeutically effective amount is well within the capability of those skilled in the art, especially in light of the detailed disclosure provided herein, as discussed in detail above.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the active ingredient at a sufficient amount to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

According to one embodiment, the composition is administered at least once, twice or three times daily (e.g. at least one daily administration).

According to one embodiment, the composition is administered once, twice or three times daily (e.g. once daily administration).

According to one embodiment, the composition is administered for 1-90 days, 1-60 days, 1-45 days, 1-30 days, 1-21 days, 1-14 days, 1-12 days, 1-10 days, e.g. 1-8 days, e.g. 1-5 days, 1-3 days, e.g. 1-2 days, 3-30 days, 3-21 days, 3-15 days, 3-12 days, 3-10 days, e.g. 3-7 days, e.g. 3-6 days, 3-5 days, 3-4 days, 5-30 days, 5-21 days, 5-15 days, 5-12 days, 5-10 days, e.g. 5-8 days, e.g. 5-7 days, 5-6 days.

According to one embodiment, the composition is administered for at least 1, 2, 3, 4, 5, 6, 7, 8, 9, 10, 12, 14 or 21 days (e.g. for at least 3 days, e.g. for at least 5 days, e.g. for at least 7 days).

According to one embodiment, the composition is administered for 1, 2, 3, 4, 5, 6, 7, 8, 9, 10, 12 or 14 days (e.g. for 3 days, e.g. for 5 days, e.g. for 7 days).

According to one embodiment, the composition is administered on consecutive days.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Compositions comprising a preparation of the invention formulated in a compatible pharmaceutical carrier may also be prepared, placed in an appropriate container, and labeled for treatment of an indicated condition, as is further detailed above.

The cell-derived particles presenting heterologous CD24 of the invention (e.g. Exo-CD24) can be suitably formulated as pharmaceutical compositions which can be suitably packaged as an article of manufacture. Such an article of manufacture comprises a label for use in treating inflammation associated with tissue damage, cytokine storm syndrome and Coronavirus infection, the packaging material packaging a pharmaceutically effective amount of the cell-derived particles presenting heterologous CD24.

It will be appreciated that the cell-derived particles presenting heterologous CD24 (e.g. Exo-CD24) or compositions comprising same of the present invention may be administered in combination with other known treatments, including but not limited to, anti-viral drugs, anti-inflammatory agents, anti-microbial drugs, anti-fungal drugs, dietary supplements (e.g. vitamins, minerals), or any other compound with the ability to reduce or abrogate inflammation associated with tissue damage, cytokine storm syndrome and Coronavirus infection.

Non-limiting examples of anti-viral drugs include, but are not limited to abacavir; acemannan; acyclovir; acyclovir sodium; adefovir; alovudine; alvircept sudotox; amantadine hydrochloride; amprenavir; aranotin; arildone; atevirdine mesylate; avridine; chloroquine; cidofovir; cipamfylline; cytarabine hydrochloride; delavirdine mesylate; desciclovir; didanosine; disoxaril; edoxudine; efavirenz; enviradene; envlroxlme; famciclovir; famotine hydrochloride; fiacitabine; fialuridine; fosarilate; trisodium phosphonoformate; fosfonet sodium; ganciclovir; ganciclovir sodium; hydroxychloroquine; idoxuridine; indinavir; kethoxal; lamivudine; lopinavir; lobucavir; memotine hydrochloride; methisazone; nelfinavir; nevlrapme; penciclovir; pirodavir; remdesivir; ribavirin; rimantadine hydrochloride; ritonavir; saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zidovudine; zinviroxime, interferon, cyclovir, alpha-interferon, and/or beta globulin.

According to a specific embodiment, the anti-viral drug comprises Remdesivir.

Non-limiting examples of anti-inflammatory agents include, but are not limited to, NSAIDs (Non-Steroidal Anti-inflammatory Drugs), corticosteroids (such as prednisone) and anti-histamines.

Anti-inflammatory agents which may be used according to the present teachings include, but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

According to one embodiment, the antimicrobial agent is an antibacterial agent such as an antibiotic.

Exemplary antibiotics include, but are not limited to, penicillins (e.g., amoxicillin and amoxicillin-clavulanate), clavulanate acid, trimethoprim-sulfamethoxazole, fluoroquinolone (e.g., ofloxacin, ciprofloxacin, levofloxacin, trovafloxacin), cephalosporins (e.g., cefuroxime, ceflacor, cefprozil, loracarbef, cefindir, cefixime, cefpodoxime proxetil, ceflbuten, and ceftriaxone), macrolides, azalides (e.g., erythromycin, clarithromycin, and azithromycin), sulfonamides, ampicillin, tetracycline, chloramphenicol, minocycline, doxycycline, vancomycin, bacitracin, kanamycin, neomycin, gentamycin, erythromycin, spectinomycin, zeomycin, streptomycin and combinations thereof.

Exemplary antifungal agents include, but are not limited to, terbinafine, clotrimazole, econazole, nystatin, selenium sulfide and ketoconazole.

According to one embodiment, the cell-derived particles presenting heterologous CD24 (e.g. Exo-CD24) or compositions comprising same of the present invention may be administered in combination with an immunotherapy.

According to one embodiment, the cell-derived particles presenting heterologous CD24 (e.g. Exo-CD24) or compositions comprising same of the present invention may be administered in combination with a monoclonal antibody treatment. For example, but not limited to, with bamlanivimab (Eli Lilly), etesevimab (Eli Lilly), casirivimab (Regeneron), imdevimab (Regeneron), or combination thereof.

According to a specific embodiment, the cell-derived particles presenting heterologous CD24 (e.g. Exo-CD24) or compositions comprising same of the present invention may be administered in combination with any one or combination of Actmera® (Tocilizumab), Remdesivir, Baricitinib (e.g. such as in combination with Remdesivir), Dexamethasone, Anticoagulation drugs (e.g., Clexane, Eliquis® (apixaban)), Nexium® (esomeprazole), Proton-pump inhibitors (PPIs), Tavanic (Levofloxacin), Acetylcysteine, Inhaled Corticosteroid (ICS), Aerovent, Solvex (Bromhexine Hydrochloride), Sopa K (Potassium gluconate), Chloroquine (e.g. Hydroxychloroquine), Antibiotic (e.g. Azenil/Azithromycin/Zitromax®, Amoxicillin/Moxypen Forte®, Ceftriaxone/Rocephin®).

Any of the above described agents may be administered individually or in combination, together or sequentially.

The cell-derived particles presenting heterologous CD24 (e.g. Exo-CD24) or compositions comprising same of some embodiments of the present invention may be administered prior to, concomitantly with or following administration of the latter.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical, and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 8 is expressed in a DNA sequence format (e.g., reciting T for thymine), but it can refer to either a DNA sequence that corresponds to an CD24 nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Plasmid Construction

Initially, a DNA fragment coding for a full-length murine CD24 fragment was amplified by PCR using the plasmid pHR'CMV-HSA as a template using primers NheI-kozak-HSA F-(5'-ATATATGCTAGCGCTACCGGACTCA-GATCTgCCatgggcagagcgatgg-3', SEQ ID NO: 1) and HSA-EcoRI R-(5'-ATATATGAATTCGAAGCTT-GAGCTCgtactaacagtagagatgtagaag-3', SEQ ID NO: 2). The PCR product was digested by NheI and EcoRI and inserted into the pIRES-GFP plasmid, which was cleaved with the same enzymes. The resulting plasmid was named CD24/HSA-IRES-GFP. The DNA and protein sequences are set forth in SEQ ID Nos: 3-6.

HSA TraNsient Expression in NIH3T3 or EXPI-293 Cells

For animal efficacy studies: NIH3T3 mouse fibroblast cells were seeded at a density of $8 \times 10^5$ cells in 10-cm tissue culture plates in complete medium (supplemented with 5% FBS). After 24 hours, cells were transfected with CD24/HSA-IRES-GFP using Lipofectamine® 2000 (Invitrogen, 11668-019) according to the manufacturer protocol. Briefly, 80 µl Lipofectamine® were added to 170 µl OPTI-MEM™ medium (Gibco, 11058021) in an eppendorf tube. 25 µg plasmid were added to a final volume of 250 µl with OPTI-MEM™ medium in a separated tube. Plasmid solution was added to the Lipofectamine® solution and the mixed stock incubated for 5 minutes at room temperature (RT). 5 ml of medium were removed for higher transfection efficiency. Then 500 µl of Plasmid-Lipofectamine® complexes were added to each plate. After 4 hours, 5 ml of DMEM 5% FBS were added to the plates. After 24 hours, transfection efficiency was evaluated according to GFP expression and medium replaced to serum free medium (6 ml) (DCCM) for 72 hours. The secreted exosomes were collected and processed as described below.

For animal toxicity studies: Expi293™ cells were used. Expi293™ cells are human cells derived from the 293 cell line and are a core component of the Expi293™ expression system. They grow to high density in Expi293™ expression medium and enable high protein expression levels throughout many passages after thawing. The cells were transfected with murine HSA/CD24 plasmid as discussed above for NIH3T3 mouse fibroblast cells. However, for transfection of Expi293F™ cells, ExpiFectamine™ was used as the transfection agents. The secreted exosomes were collected and processed as described below.

Preparation of the CD24 Expressing Exosomes—Termed as EXO-CD24

The Human CD24 gene (as set forth in SEQ ID No: 8) was cloned downstream to two tetracycline-operator sequences, resulting in pCDNA4/TO-CD24 plasmid (as set forth in SEQ ID No: 7), which was then transfected into Tet repressor-expressing HEK-293 cells (T-REx™-293), allowing tight on/off regulation, thereby resulting in a very low background or leaky CD24-expression. pCDNA4/TO-CD24 was transfected into 293T-REx™ cells, using the calcium phosphate transfection method. 48 hours after transfection, the cells were seeded into DMEM medium supplemented with 10% fetal bovine serum (FBS, sourced from US farms, United States department of Agriculture (USDA)-approved), containing the selectable marker Zeocin™ (InvivoGen, 100 µg/ml). The cells were seeded at different levels: 500, 1,000, 3,000, 5,000, and 10,000 cells. Several clones were isolated as individual clones based on visual assessment. Upon growth of clearly defined colonies that likely originated from a single cell, separate clones were collected and seeded onto 24-well plates. When cultures reached 90% confluence, the colonies were sub-cultured to 6-well plates. Then, upon reaching 90% confluence, colonies were sub-cultured to 25 cm flasks.

Isolated clones were characterized by Western immunoblotting with anti-CD24 antibodies and FACS analysis. Stability of the pCDNA4/TO-CD24 clones was established and their CD24 gene-tetracycline inducibility was confirmed. Clone 15 with high inducible expression was chosen. A total amount of $7 \times 10^7$ cells were seeded in a cell factory system (50% confluence), in growth medium, to a total volume of 200 ml complete medium supplemented with 1 µg/ml tetracycline. 5% of USDA-approved serum, sourced from US farms was added (the serum received a Certificate of Analysis according to the certified laboratory Biological Industries and a Certificate of Origin according to the Ministry of Agricultural and Development Animal Health Division of Chile). After 48 hours of incubation, the biofluid was removed and cells were washed twice with 100 ml phosphate buffered saline (PBS). Following the wash, 200 ml of serum- and protein-free Expi293™ medium supplemented with 1 µg/ml tetracycline was added for 72 hours (37° C., 5% CO2). Following incubation, the biofluid was collected into 50 ml tubes and centrifuged at 3000×g for 15 minutes (4° C.) to remove cells and cell debris. The supernatant was filtered using a 0.22-micron pore size filter. ExoQuick®-CG (SBI system biosciences) exosome precipitation solution was added to the biofluid (3.3 ml/10 ml biofluid) and the tubes were mixed by gentle inversion. The tubes were refrigerated overnight (at least 12 hours). On the following day, the ExoQuick®-CG/biofluid mixture was centrifuged at 2500×g for 30 minutes, 4° C., and the supernatant was aspirated. The residual ExoQuick®-CG solution was removed by centrifugation at 2500×g for 5 minutes, followed by aspiration of all traces of fluid. The exosomes in the pellet were re-suspended in saline (0.5-2.5 ml) and transferred to a dialysis cassette. Dialysis was performed against 5 L of freshly prepared PBS, overnight, 4° C. The exosomes were transferred into an Amicon tube (10000 MW) and centrifuged at 15° C. until they reached the preferred volume. The purified exosomes were (sterile) filtered, using a sterile 0.22-micron pore size filter, into a 2 ml cryo-tube (PP, round bottom, natural screw cap, sterile, Greiner, Lot 121263). Approximately 50-100 µl were used for evaluation of exosome concentration and the remaining exosomes were kept at 4° C.

Variations to the above described protocol:
Growth Media

In addition to the Expi293™ medium discussed above, additional induction mediums were tested in order to increase the total number of exosomes generated. The cells were transfected and grown as discussed above and only the growth medium was replaced. Specifically, four different cell culture mediums were tested:
1. EX-Cell® medium (Sigma Aldrich)
2. NutriStem® hPSc medium (Biological Industries)
3. NutriVero™ medium (Biological Industries)
4. Expi293™ medium (ThermoFisher Scientific)+5% human serum albumin+14 microU/ml Insulin The different culture mediums were further supplemented with 1 µg/ml tetracycline for induction of CD24 expression, as further discussed below. The exosomes were then examined by NanoSight™, Nano-tracking analysis device.

Suspension Cultures

In addition to the growth of cells in adherent cultures, discussed above, the cells were further cultured in suspension cultures, in a shaker incubator, without the addition of human serum albumin and without insulin. The cells were grown to high density culture with Expi293™ medium as discussed above. The medium was replaced with Expi medium supplemented with tetracycline for 72 hours. The exosomes were then collected, purified and tested using the NanoSight™.

Exosome Isolation

Exosome isolation by a polyethylene glycol (PEG)-based method was examined and compared to the ExoQuick® discussed above. Specifically, PEG solution was prepared by combining PEG [with Mn (number average molecular weight) of 6000 (sigma, 81260)] with ultra-pure water and sodium chloride (0.5 M). PEG solutions were added to culture media at several concentrations between 5% and 12% and refrigerated overnight. The following day, samples were centrifuged for 1 hour at maximum speed. The resulting pellets were suspended and particles were characterized using a nanoparticle tracker (NanoSight™).

Quantification of Concentration of CD24 Expressing Exosomes (EXO-CD24)

Exosomes were captured intact on the high protein binding microtiter plate (maxi-sorb, Nunc). The wells were incubated with an anti-CD63 primary antibody which recognizes the tetraspanin protein on the exosomal surface. Horseradish Peroxidase enzyme-linked secondary antibody was used for signal amplification. A colorimetric substrate (extra-sensitive TMB) was used for the assay read-out. The accumulation of the colored product was proportional to the amount of specific CD63 antigen present in each well. The results were quantified by a microtiter plate reader at 450 nm absorbance.

For expression of CD24, the exosomes were bound to 96-well maxi-sorp plates and ExoELISA™ was performed using 20 µg/ml anti-CD24 mAb as the detecting antibody (HRP-conjugated anti-mouse antibody, diluted 1:5000, was used as secondary antibody). ELISA was developed using the chromogenic HRP substrate TMB. Color development was terminated with 1 M H2SO4 and the plates were read at 450 nm.

The ExoELISA-ULTRA™ protein standard was diluted 1:1000 in coating buffer in a microcentrifuge tube. This dilution was used as the first standard of the standard curve. Then, serial dilutions (blank, 1, 1:2, 1:4, 1:8, 1:16, 1:32, 1:64) of the first standard were performed in coating buffer. 50 µl of freshly prepared protein standard and exosome samples were added to the appropriate well of the micro-titer plate. The plate was covered with sealing film/cover. The plate was incubated at 37° C. for 1 hour (a micro-titer plate shaker was used for all subsequent incubation). After incubation, the plate was inverted to empty all contents. The plate was washed 3 times for 5 minutes with 100 µl 1× wash buffer (a micro-titer plate shaker was used for all subsequent washing). CD63 primary antibody was diluted 1:100 in blocking buffer and 50 µl was added to each well. The plate was incubated at room temperature for 1 hour with shaking. The plate was then washed 3 times for 5 minutes each with 100 µl 1× wash buffer. The secondary antibody was diluted 1:5000 in blocking buffer and 50 µl was added to each well. The plate was incubated at room temperature for 1 hour with shaking. The plate was then washed 3 times for 5 minutes each with 100 µl 1× wash buffer. 50 µl of super sensitive TMB ELISA substrate was added and incubated at room temperature for 5-15 minutes with shaking. 50 µl of stop buffer were added and the plate was read (spectrophotometric plate reader at 450 nm) immediately to provide a fixed endpoint for the assay. The product was dispensed into the final vials (Amber Glass, 2 mL, 13 mm) at 0.5 mL per vial. All activity was performed in a Class A laminar flow hood located within a Class B production clean room. Sterility and LAL test were performed. The presence of residual BSA was tested using a commercial kit (Biotest, E11-113).

Western Blot Analysis

The expression of CD24 on the purified exosomal membranes was also examined by Western Blot analysis using an anti-CD24 monoclonal antibody prepared in-house. The membrane was reprobed with anti-HSP70 antibody to confirm that the sample was indeed an exosomal sample. In addition, purified CD24 recombinant protein was used as positive control for CD24 detection.

Exosome Tracking Analysis with Nanosight™

The Nanoparticle Tracking Analysis (NTA) device (Version: NTA 3.4 Build 3.4.003) was used to characterize nanoparticles in solution, enabling a validation of the quantification of the exosomes, as well as determine particle size. Each particle was individually but simultaneously analyzed by direct observation and measurement of diffusion events. This particle-by-particle methodology produces high resolution results for nanoparticle size distribution and concentration, while visual validation provides users with additional confidence in their data. Both particle size and concentration were measured. Using this technique allowed to validate the quantification of the exosomes in the product. The following settings were used: Script Used: SOP Standard Measurement 01-13-58PM 02J~; Camera Type: sCMOS, Laser Type: Blue488, Camera Level: 14, Slider Shutter: 1259; Slider Gain: 366, FPS 25.0. The following analysis settings were used: Detect Threshold: 7, Blur Size: Auto, Max Jump Distance: Auto: 11.1-21.4 pi; Number of Frames: 1498, Temperature: 25.2-25.3° C., Viscosity: (Water) 0.882-0.886 cP. The following parameters were evaluated during analysis of recordings monitored for 60 s: the diameter of the particles, the mode of distribution, the standard deviation, and the concentration of vesicles in the suspension. Before NTA measuring, an aliquot of the isolated vesicles was thawed at room temperature and diluted 100 times in saline. The measurements were performed at least twice. Five videos (60 sec each) of Brownian motion of nanoparticles were recorded and analyzed. The samples were measured with a manual shutter. As a laser beam is passed through the chamber containing the particle suspension, the camera captures scattered light at dozens of frames per second to track the Brownian motion of the particles. The NTA software tracked several particles individually and uses the Stokes-Einstein equation to calculate the hydrodynamic diameter of the particles.

Storage and Handling

Product preparation was carried out in a clean room within the hospital, under GMP guidelines, and maintained at −80° C. until use. The cells with the exosomes were sent to Hylabs laboratories for sterility testing and *mycoplasma* and microorganisms assessment. The appearance of the diluted exosomes was a clear solution to white turbidity, depending on particle concentration. The Exo-CD24 product was packed in an empty, sterile, 3.5-5 ml tube with a swivel stopper allowing the Exo-CD24 product to be removed with a sterile syringe. The Exo-CD24 product was transferred from the clean room to the patient refrigerated (on ice).

GMP Production and Sterility Testing

Exo-CD24 was manufactured at the facility of Accellta Ltd. (Technion City, Malat Building, Haifa, Israel) that complies with good manufacturing practice (GMP) standards of manufacturing. The following tests were performed at Hy Laboratories (hylabs, Israel): *Mycoplasma* nested PCR; Sterility (Batch no. 1, Batch no. 2, and Batch no. 3); Validation of Sterility (Batch no. 1); Sterility after 1 month (Batch #1); Endotoxin (LAL) Test and Validation (Batch no. 1, Batch no. 2, and Batch no. 3), and sterility and validation tests were performed for the secreting cells at Hy Laboratories. Acceptance criteria for Sterility testing were as follows: Less than 5000 Units: No Growth; More than 5000 Units: Growth, Positive. Validation testing for the sterility test was done with a growth promotion test under aerobic conditions, monitoring for bacteria up to 3 days, and fungi up to 5 days.

Effect of EXO-CD24 on Secretion of Pro-Inflammatory Cytokines In-Vitro

U937 cells were maintained in suspension culture in Roswell Park Memorial Institute (RPMI)-1640 supplemented with 10% (v/v) heat-inactivated fetal bovine serum (FBS), at 37° C. in a humidified atmosphere of 5% CO2. Cell differentiation was induced by exposing them ($80\times10^3$ cells/well, 24 wells plate) to 100 ng/ml of phorbol 12-myristate 13-acetate (PMA) for 72 hours. After 72 hours, 10 µg/ml hrHMGB1 and Exo-CD24 were added for 24 hours. Biofluids were collected and cytokine levels were examined using "Multi-plex array" (Human XL Cytokine Discovery Fixed Panel, AML).

Animal Husbandry

This study was performed under the approval by "The Israel Board for Animal Experiments", in compliance with "The Israel Animal Welfare Act" and Ethics Committee, and performed at the Science in Action (SIA) CRO, Ness Ziona, Israel. SIA is certified to perform animal studies by the Israeli ministry of health animal care and use national committee.

Animals were purchased from Envigo (Indiana, USA) and acclimatized for 7-8 days upon arrival. Identification was done by a cage card containing the study name, animal number and relevant details as to treatment group. The mice were numbered with non-erasable marking pen on the tail. Animal handling was performed according to guidelines of the National Institute of Health (NIH) and the Association for Assessment and Accreditation of Laboratory Animal Care (AAALAC). Animals were housed in polyethylene cages (5/cage) measuring 35×30×15 cm, with stainless steel top grill facilitating pelleted food and drinking water in plastic bottle; bedding: steam sterilized clean paddy husk were used and bedding material was changed along with the cage at least twice a week. Animals were provided ad libitum a commercial rodent diet, sterilized. Animals had free access to acidified autoclaved drinking water obtained from the municipality supply. The food arrived from the vendor with a Certificate of Analysis. The water was treated as above. Environment conditions: Animals were housed in IVC cages in dedicated HVAC (Heat, Ventilation and Air Conditioning) animal facility at temperature of 22±2° C. and RH (Relative Humidity) of 55±15%. Temperature and humidity were monitored continuously. The facility had no exposure to outside light, and it was maintained on automatic alternating cycles of 12 hours light and 12 hours dark. Animals were allocated randomly into the study groups. The route of administration of the therapeutic was intratracheal.

In Vivo Toxicity in an Animal Model Female Balb/c mice, 30 in total, were purchased from Envigo (Indiana, USA). They were divided into three treatment groups and were treated by daily inhalation for 5 days, with either saline, mid-dose ($5\times10^8$/mice) or high-dose murine Exo-CD24 ($1\times10^9$/mice). A detailed clinical observation was carried out prior to dosing, frequently for the first three hours post first dosing, and two times a week thereafter (prior to administration) and before termination. Mortality/morbidity was determined by cage-side, twice-daily observation. Body weight was determined pre-test, prior to dosing on Day 1 and once weekly afterwards. The mice were fed once pre-test and weekly during the dosing. Ophthalmoscopic examination was carried out once pre-test and once before necropsy. Urine analysis was carried out on all surviving animals at necropsy on both study and recovery animals. Clinical pathology, including hematology and clinical chemistry testing, were carried out on all main study and recovery animals once prior to necropsy. The following tissues were preserved for future investigation: abnormal tissues, brain, heart (sections of left and right ventricles and atria, septum with papillary muscle), kidneys, liver, lungs, spleen, thymus and thyroid. The following organs were weighed: brain, heart, kidneys, liver, lungs, spleen, and thymus. Tissues from the high dose and vehicle groups were processed to slides and evaluated by a certified pathologist by microscopic evaluation. Recovery groups were evaluated based on the results of the control and high dose main study groups.

In Vivo Efficacy in an Animal Model

A total of 35 female, 8-week-old, BALB/C mice were divided into four test groups. In groups 1-3, acute respiratory distress syndrome (ARDS) was induced using LPS of *E. coli* origin, serotype 055:B5 (ChemCruz, Batch/lot No.: C3120). To induce ARDS, BALB/c mice were anaesthetized and orally intubated with a sterile plastic catheter and challenged with intratracheal instillation of 800 µg of LPS dissolved in 50 µL of normal PBS. Naive mice (without LPS instillation, study group 4) served as a control. The treatment consisted of daily inhalation of aerosolized murine Exo-CD24 exosomes via endotracheal tube as indicated in Table 1, below. Treatment started 3 hours after LPS administration. The study was terminated 72 hours after the LPS challenge to collect tissues for analysis. Sample collection was done as follows: Serum bleeding was performed for cytokine analysis. Bronchial Alveolar Lavage (BAL) differential cell count by was done by fluorescent activated cell sorting (FACS), for T and B lymphocytes, eosinophils, neutrophils, dendritic cells and monocytes/macrophages. BAL fluid samples were taken for cytokine analysis. Lungs were isolated from all animals sacrificed on Day 3, for histopathology using hematoxylin and eosin (H&E) staining.

TABLE 1

Group Designation

| Group number | Experimental group | N | Treatment | Treatment frequency | ROA |
|---|---|---|---|---|---|
| 1 | LPS | 10 | Murine Exo-CD24 $1 \times 10^8$/mice | Daily (30 µl in the first day and 50 µl in the next 2 days) | Intratracheal |
| 2 | LPS | 10 | Murine Exo-CD24 $1 \times 10^9$/mice | Daily (30 µl in the first day and 50 µl in the next 2 days) | Intratracheal |
| 3 | LPS | 10 | Saline | Daily (30 µl in the first day and 50 µl in the next 2 days) | Intratracheal |
| 4 | NON | 5 | Naive | NONE | NONE |

Histology

The lungs of 34 animals were harvested, fixed in 4% formaldehyde and transferred to Patho-Logica (Ness-Ziona, Israel) in fixative. The tissues were sectioned and, placed in cassettes and processed routinely for paraffin embedding. Each animal had one tissue block prepared. Paraffin blocks were sectioned at approximately 4-micron thickness. The sections were put on glass slides and stained with H&E. A semi-quantitative analysis of Acute Lung Injury (ALI) was performed using a severity scoring scale of 0-2 (Table 2, below) based on the American Thoracic Society Documents, 2011. The final score was determined by summing up the score of Fibrin, neutrophils and thickened alveolar walls for each mouse and averaging the results for each group.

TABLE 2

Acute Lung Injury (ALI) scoring

| Group 1 | Group 2 | Group 3 |
|---|---|---|
| 4.6 ± 0.84 | 4.0 ± 0.81 | 4.7 ± 1.11 |

Phase 1 Clinical Trial

A Phase I clinical study has been initiated to evaluate the safety of Exo-CD24 exosomes in patients with moderate/severe COVID-19 disease. Patients with a moderate/severe COVID-19 infection and factors predictive of a cytokine storm from the Corona department of Tel Aviv Sourasky Medical Center (TASMC) who have provided an informed consent were recruited in four groups:

Group 1, open-label: The first group of five patients received $1 \times 10^8$ Exo-CD24 exosome particles, Group 2, open label: the second group of another five patients received $5 \times 10^8$ Exo-CD24 exosome particles.

Group 3, open-label, 20 patients received Exo-CD24 exosomes at a concentration of $1 \times 10^9$ exosome particles.

Group 4, open-label, 5 patients received Exo-CD24 exosomes at a concentration of $1 \times 10^{10}$ exosome particles.

Compassionate use, 1 patient received Exo-CD24 exosomes at a concentration of $1 \times 10^8$ exosome particles.

Exo-CD24 exosomes were diluted in normal saline for inhalation and given once daily (QD) for 5 days. Study treatments were given as an add-on to standard of care. The treatment was given by medical staff in a separate room with no other patients present. Following the 5 days of treatment, patients remained in follow-up for 30 additional days.

Primary and secondary end points as described in the clinical approved protocol.

Primary Safety Objective: To evaluate the safety of CD24 exosomes in patients with moderate/severe COVID-19 disease e.g., inducing bronchospasms, superinfection, severe clinical deterioration, all-cause mortality and viral load.

Exploratory Objectives: (1) To evaluate the efficacy of CD24 exosomes in reducing respiratory rate in patients with moderate/severe COVID-19 disease; (2) To evaluate the efficacy of CD24 exosomes in increasing blood oxygen saturation (SpO2) in patients with moderate/severe COVID-19 disease; (3) To evaluate the efficacy of CD24 exosomes in preventing the need for ventilation in patients with moderate/severe COVID-19 disease; (4) To evaluate the efficacy of CD24 exosomes in increasing the lymphocyte count in patients with moderate/severe COVID-19 disease; and (5) To evaluate the efficacy of CD24 exosomes in improving the neutrophil-to-lymphocyte ratio (NLR) in patients with moderate/severe COVID-19 disease.

Primary Safety Endpoints: (1) Number of adverse events and adverse events leading to premature study termination; and (2) Viral load.

Exploratory Endpoints: (1) a composite endpoint comprised of alive at Day 5 without bronchospasms, unexpected infections, or a significant clinical deterioration compared to Baseline; (2) proportion of patients with respiratory rate less or equal to ($\leq$) 23/min for 24 hours; (3) decrease/improvement in respiratory rate from baseline to Day 5; (4) proportion of patients with SpO2 saturation of more than (>) 93% for at least 24 hours; (5) increase/improvement in SpO2 saturation from baseline to Day 5; (6) proportion of patients with no artificial ventilation after 5 days of treatment; (7) proportion of patients with an increase of 25% in the absolute lymphocyte count, sustained for more or equal to ($\geq$) 48 hours after 5 days of treatment; (8) change in the absolute lymphocyte count from baseline to Day 5; (9) proportion of patients with an increase of 20% in the NLR, sustained for more or equal to ($\geq$) 48 hours after 5 days of treatment; and (10) change in the NLR from Baseline to Day 5.

Study population: Male and female patients, age 18-85 years, with moderate/severe COVID-19 disease defined as below and cytokine storm predictive parameters.

Inclusion Criteria:
(1) a COVID-19 diagnosis confirmed with a SARS-coV-2 viral infection positive polymerase chain reaction (PCR) test;
(2) Age 18-85 years;
(3) Severity of disease according to the following criteria (at least one clinical parameter and one laboratory parameter are required):
   (a) Clinical and Imaging-based evaluation:
      (i) respiratory rate of more than (>) 23/min and less than (<) 30/min;

(ii) SpO2 at room air of less or equal to (≤) 94% and more or equal to (≥) 90%; and
(iii) bilateral pulmonary infiltrates of more than (>) 50% within 24-48 hours or a severe deterioration compared to imaging at admission;
(b) Evidence of an exacerbated inflammatory process:
(i) LDH score of more than (>) 450 u/L;
(ii) CRP of more than (>) 100 mg/L
(iii) Ferritin of more than (>) 1650 ng/ml;
(iv) Lymphopenia of less than (<) 800 cells/mm$^3$; and
(v) D-dimer of more than (>) 1 mcg/mL
(4) Willing and able to sign an informed consent.

Exclusion Criteria:
(1) Age of less than (<) 18 years or of more than (>) 85 years;
(2) Any concomitant illness that, based on the judgment of the Investigator is terminal;
(3) Ventilated patient;
(4) Pregnancy (positive urine pregnancy test [women of childbearing potential only]) or breastfeeding;
(5) Unwilling or unable to provide informed consent;
(6) Participation in any other study in the last 30 days.

Example 1

Nanosight™ Results

Figure 2B:
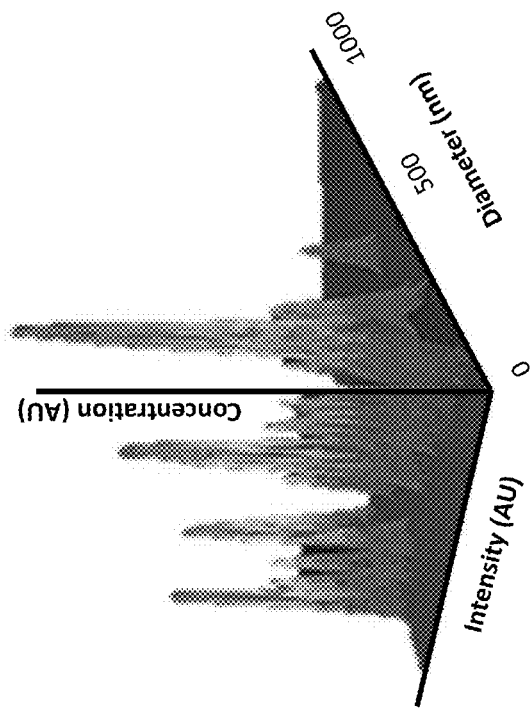
FIGS. 2A-2B illustrate exosome tracking analysis of Batch no. 1 using NanoSight™ system, showing the size range of the particles (FIG. 2A), as well as a 3D representation of the particles (FIG. 2B).
Figure 2A:
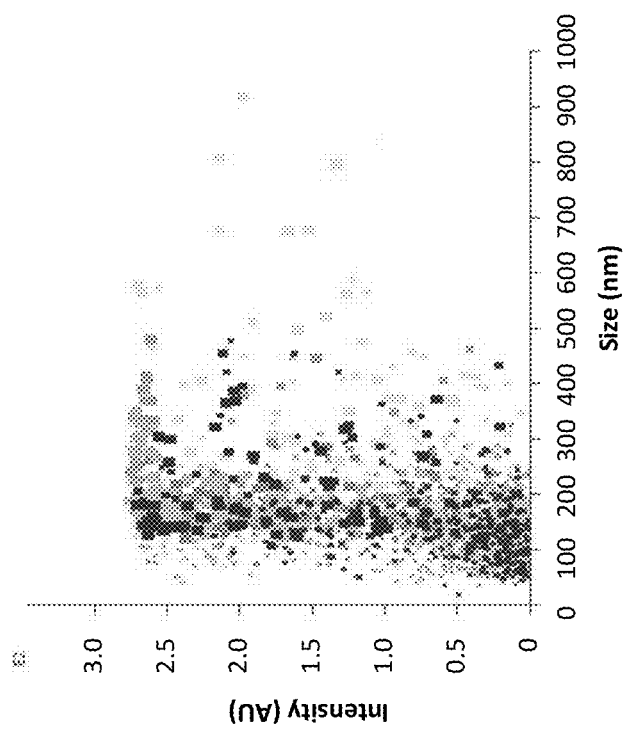

In the first GMP manufacturing (Batch no. 1) of the Exo-CD24 product, the analyzed data showed a concentration of $4.75 \times 10^7 \pm 0.43 \times 10^7$ particles/ml in the tested solution with Mode of 154.1±8.0 (FIGS. 2A-B).

Figure 3A:
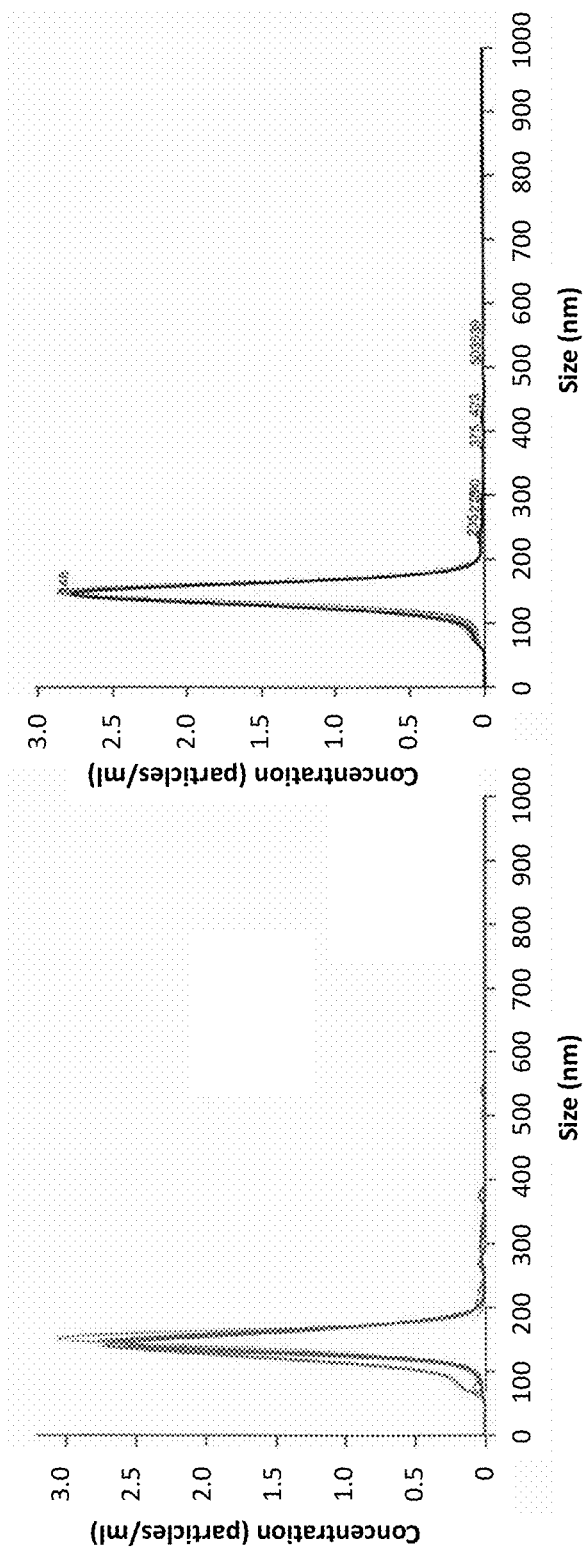
FIGS. 3A-3B illustrate tracking analysis of Batch no. 3 showing concentration and distribution (FIG. 3A) and averaged concentration from 5 measurement replicates (FIG. 3B).
Figure 3B:
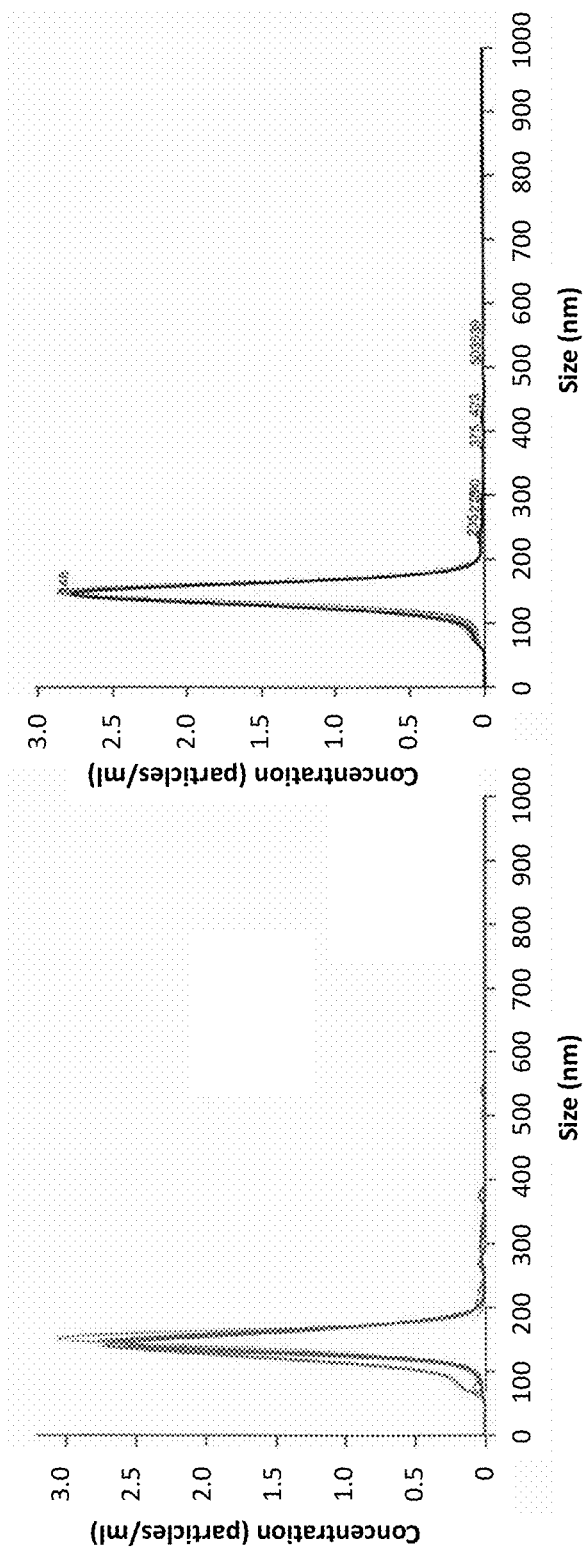
Figure 4B:
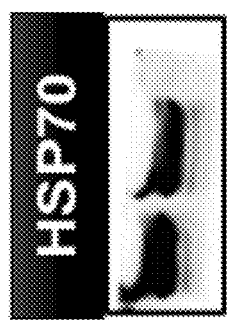
FIGS. 4A-4B illustrate a validation of the number of particles and confirmation of antigen expression on the exosomes as carried out by ExoELISA™ (FIG. 4A). Of note, the number of particles obtained by quantification of the exosomal CD63 marker was $0.9 \times 10^{11}$/ml. Additional quantification of the exosomal HSP70 marker was performed using the Western Blot analysis (FIG. 4B).
Figure 4A:
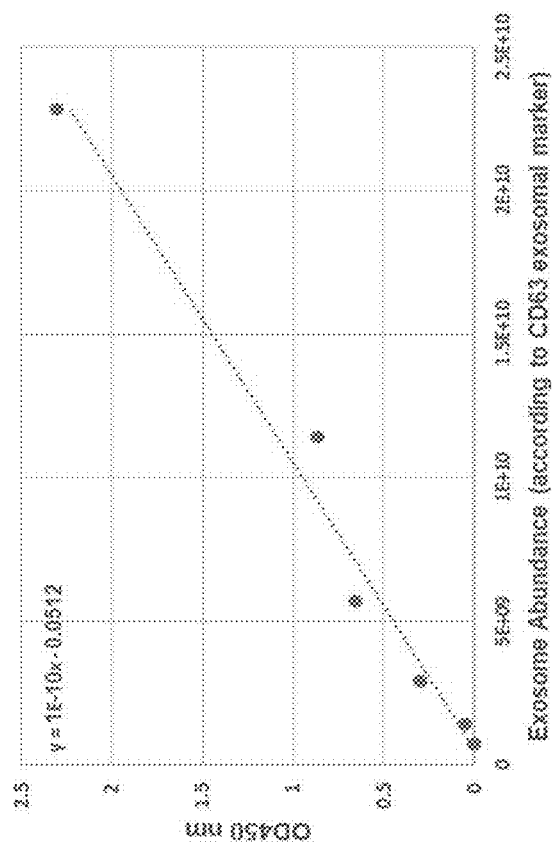

For Batch no. 3, concentration and distribution testing were carried out using NanoSight™ (FIGS. 3A-B). The obtained concentration was $1 \times 10^7 \pm 6.41 \times 10^7$ particles/mL. The concentration was then confirmed by EXO-ELISA™ detecting the exosomal marker CD63. HSP70 was used as another exosomal marker to validate, by a different bioassay, the presence of the exosomes in the solution (FIGS. 4A-4B).

Figure 5A:
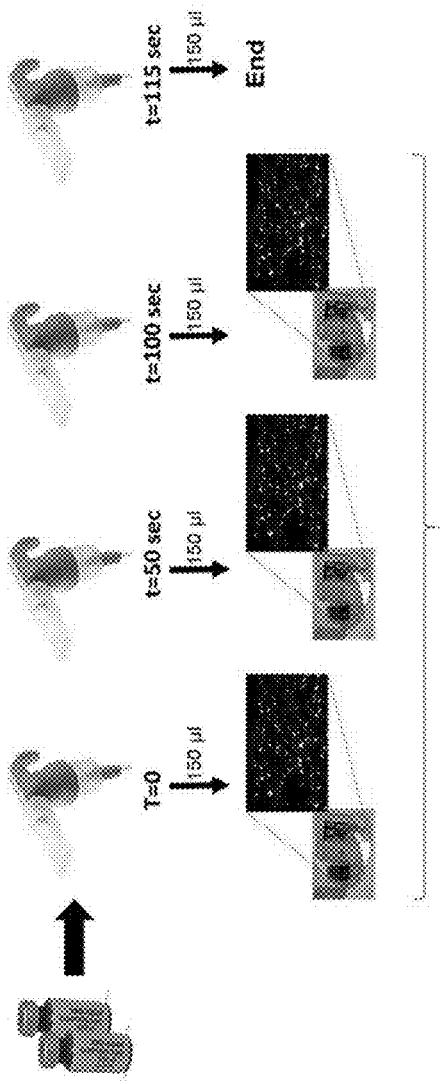
FIGS. 5A-5B illustrate product stability. The active pharmaceutical ingredient (API), was stable throughout the period of use (FIG. 5A) and at various temperatures for the duration of a month (FIG. 5B).
Figure 5B:
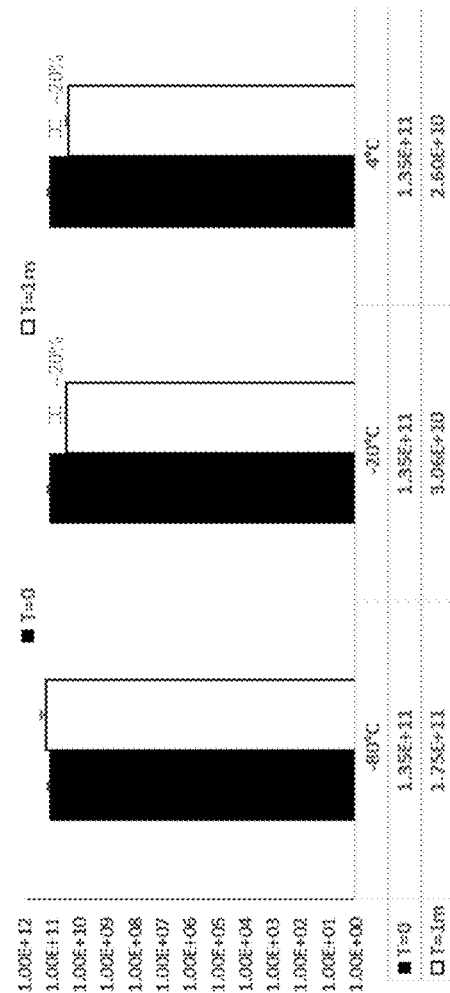

In-use stability of the Exo-CD24 product for the period of its administration was tested by confirming the preservation of the Exo-CD24 product after the vial opening and throughout the inhalation. The test demonstrated that the Exo-CD24 product remained stable throughout the period of use (FIG. 5A). Furthermore, a specially developed lyophilization process ensures stability of the active pharmaceutical ingredient (API) not only at −80° C., but also at −20° C. and 4° C. (FIG. 5B) for the duration of one month.

Example 2

The Active Pharmaceutical Ingredient (API) is of High Purity and Suitable for IV Administration
Cell Cultures for Preparation of Exosomes USDA serum, which received a Certificate of Analysis according to a certified laboratory (Biological Industries) and a Certificate of Origin according to the Ministry of Agricultural and Development Animal Health Division of (Chile), was used only for initial seeding of the cells in the culture vessel. After 48 hours of incubation, in which the cells adhered to the culture vessel, it was aspirated from the culture, washed twice in PBS and then replaced with serum- and protein-free medium (Expi293™) for another 72 hours until the exosomes were harvested. The Expi293™ medium did not contain BSA or any other animal protein (Animal Origin-Free, Chemically Defined, Protein-Free, Serum-Free). Therefore, and in light of the purification stages later in the process that also included a dialysis cycle at a volumetric ratio of about 1:2,000 (2.5 mL in 5 liters), the chance of serum residue was nil. This conclusion was based on the following calculations: Assuming that the rest of the serum after washing and replacing the medium to a serum-free medium is about 5% of the initial level (which is 5%), i.e., a level of 0.25% in the medium. The level of BSA which is the most common protein in calf/bovine serum stands at 45 g/L i.e. a medium of 5% serum contains 2.25 g/L of BSA. It is therefore assumed that after washing and dilution, the medium contains a BSA level of approximately 112.5 mg/L. It is assumed that the precipitation and wash processes lower the level to 5% from its predecessor, i.e. to 5.6 mg/L. The dialysis process mentioned above reduces the presence of BSA to a level of 0.1% from its pre-dialysis level which is about 5.6 mg/L or 5.6 ng/ml. One dose per patient contains an equivalent volume of about 5 microliters or a level of about 2.5 picograms of BSA. At the same time, the maximum level allowed by the WHO is 50 ng of BSA per dose. Therefore, in accordance with the above permit assessment, the level of BSA in the Exo-CD24 product is significantly lower than the maximum level allowed by the WHO.

Figure 5D:
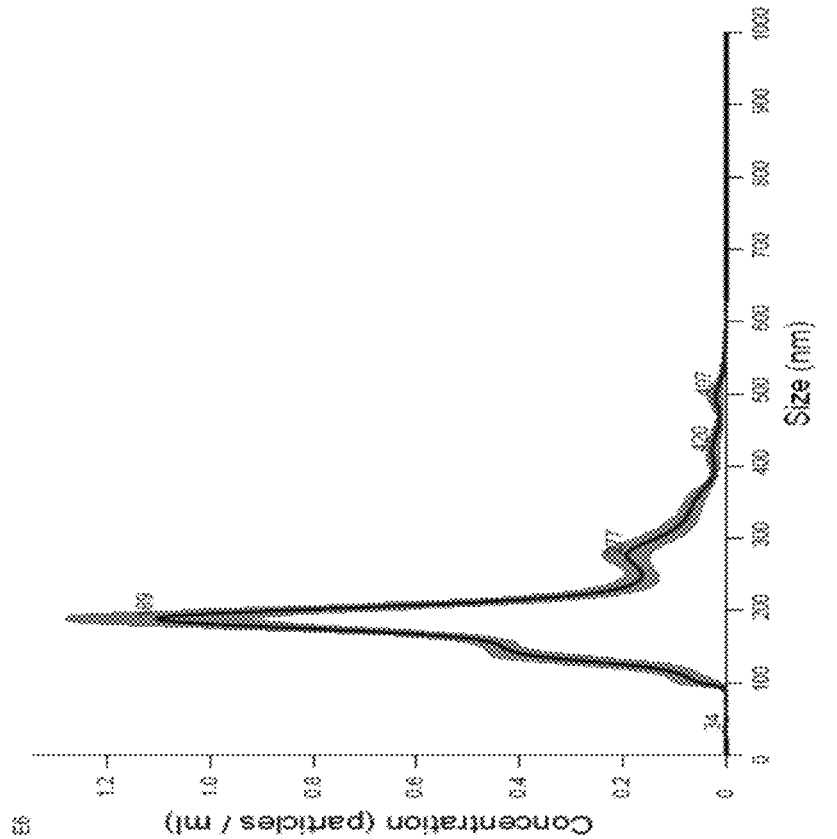
Figure 5C:
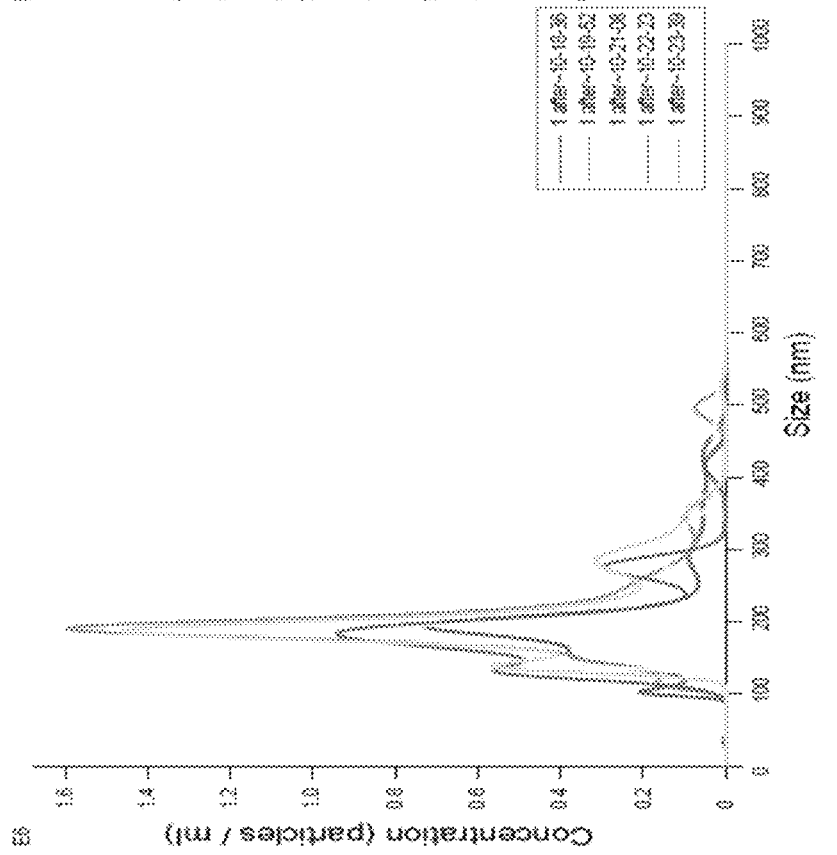
Figure 5H:
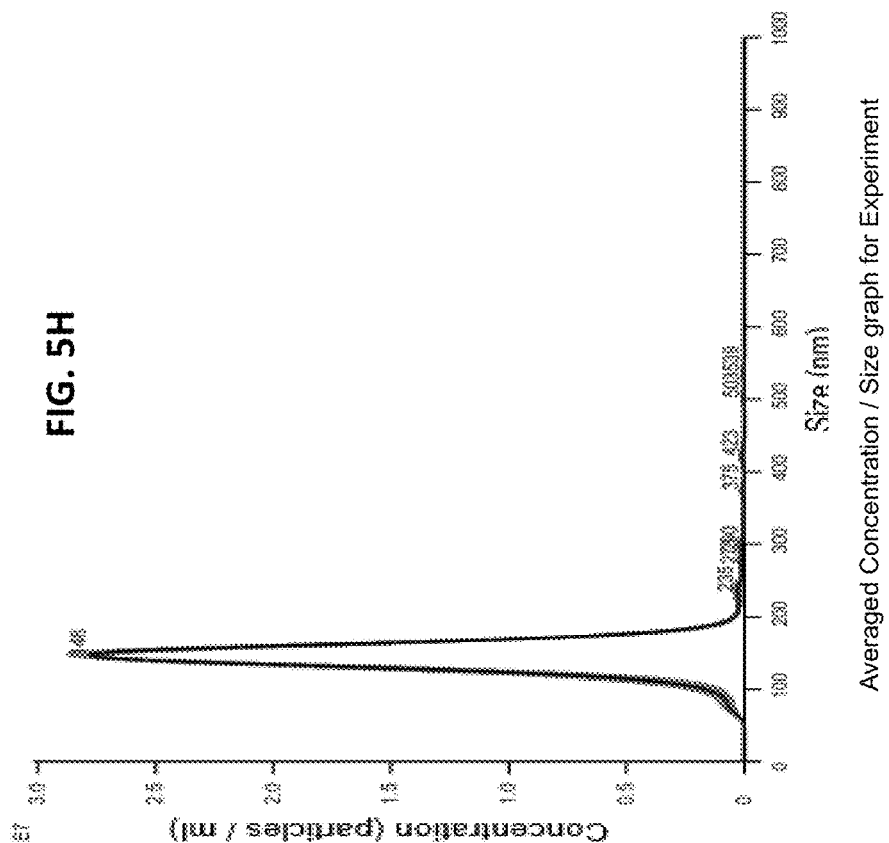
Figure 5G:
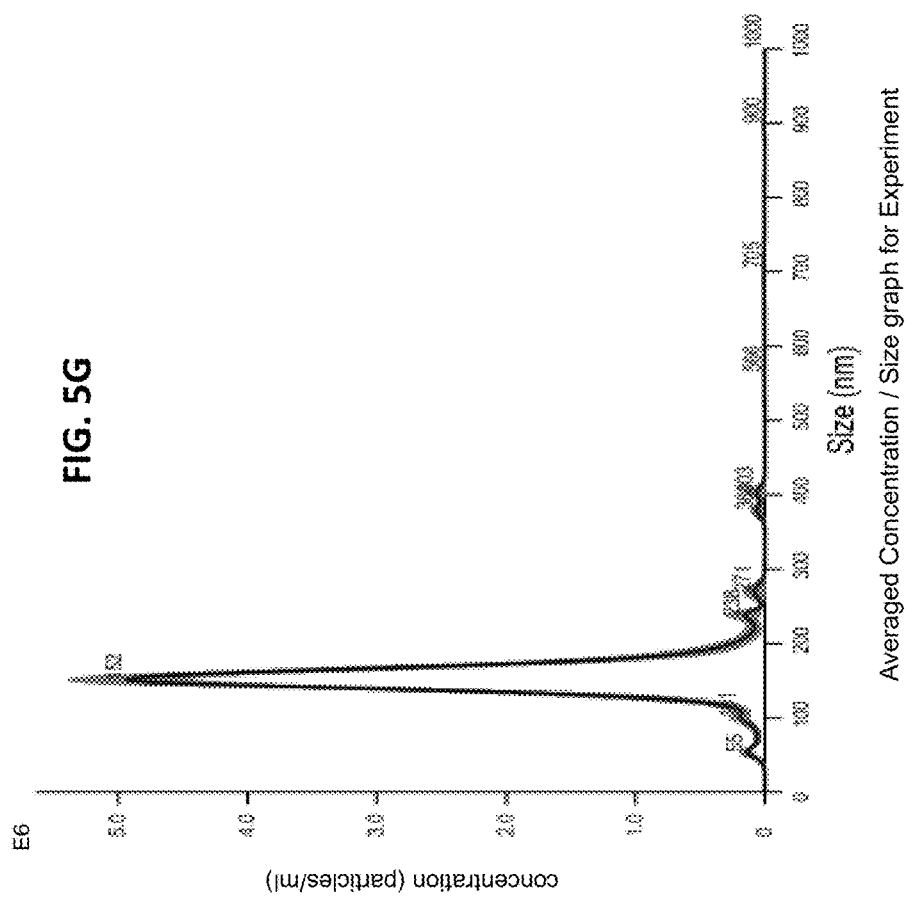

In order to increase the total amount of exosomes generated, different mediums were tested in addition to the chemically defined, serum-free, protein-free Expi293M medium. Specifically, four different mediums were tested:
1. EX-Cell® medium (an animal-protein free, serum-free medium)
2. NutriStem® hPSc medium (a defined, xeno-free, serum-free medium)
3. NutriVerom medium (a chemically defined serum-free, animal component-free medium)
4. Expi293™ medium supplemented with 5% human serum albumin and 14 microU/ml Insulin When the exosomes were tested by NanoSight™, Nano-tracking analysis device, the NutriStem® hPSc medium showed very high background and it was very difficult to see the exosomes (data not shown). The EX-Cell® medium and the NutriVerom medium gave very similar results by means of size distribution and concentration of the particles (as evident in FIGS. 5C-D and FIGS. 5E-F, respectively). Specifically, culture of cells with EX-Cell® medium resulted in particle concentration of $8.48 \times 10^7$ particles/ml (FIGS. 5C-D) and culture of cells with NutriVero™ medium resulted in particle concentration of $5.25 \times 10^7$ particles/ml (FIGS. 5E-F). The best results were obtained with the Expi293, medium supplemented with human serum albumin and insulin. Specifically, culture of cells with the Expi293™ supplemented culture medium resulted in particle concentration of $3 \times 10^8$/ml and their size distribution was uniform (FIGS. 5G-H). Accordingly, these exomes are suitable for pharmaceutical use.

Scale-Up

In order to further increase the total amount of exosomes generated (i.e. cell culture scale-up), while supporting and solving biomanufacturing challenges (e.g. the balance of product quantity, quality, cost and speed), high cell density cultures were developed. These high cell density cultures enable cells to reach steady state and stay in production phase longer than in batch or fed batch culturing.

Figure 6E:
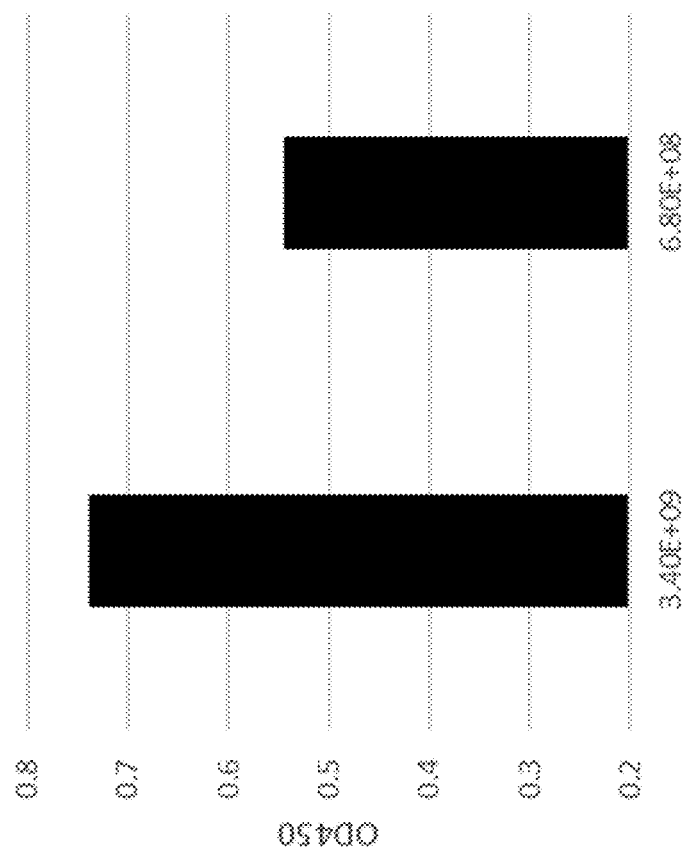
FIG. 6E illustrates the expression of CD24 on the purified exosomal membranes obtained by suspension cultures as examined by ELISA.
Figure 6F:
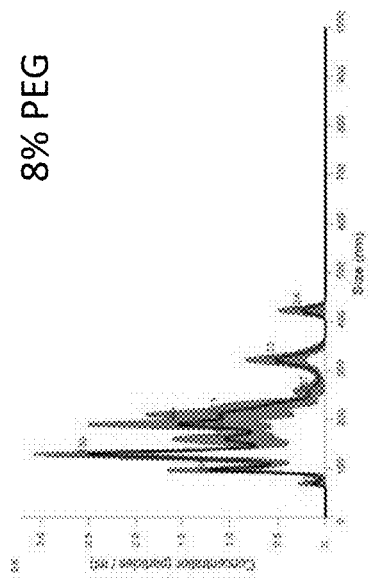
FIGS. 6F-6J illustrate size distribution of the purified exosomes obtained after exosome purification using different PEG solutions, 5-12% PEG, comparing to the standard harvest method using the ExoQuick® reagent.
Figure 6G:
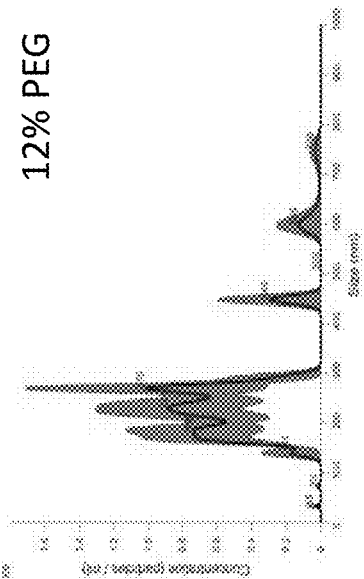
Figure 6H:
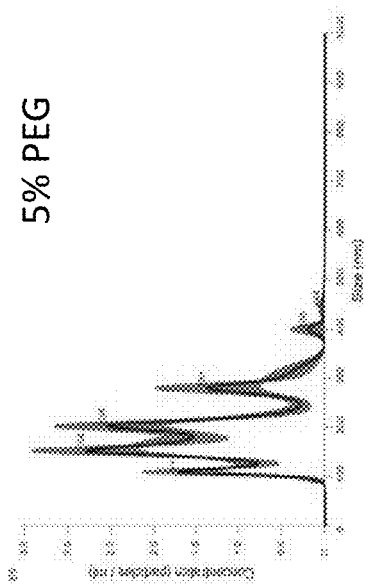
Figure 6I:
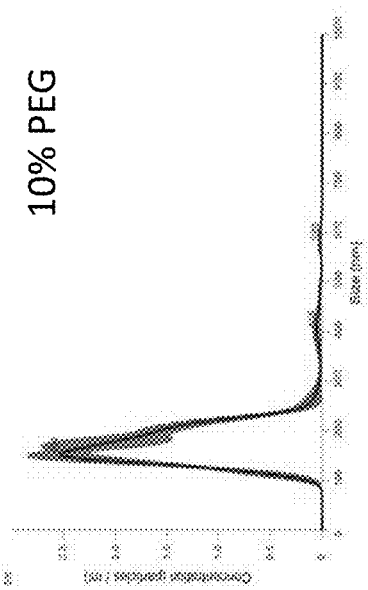
Figure 6J:
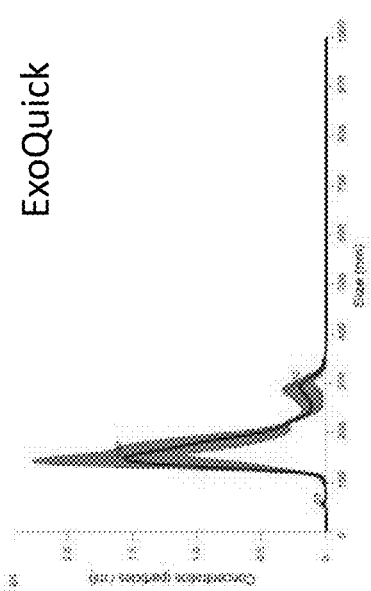
Figure 6K:
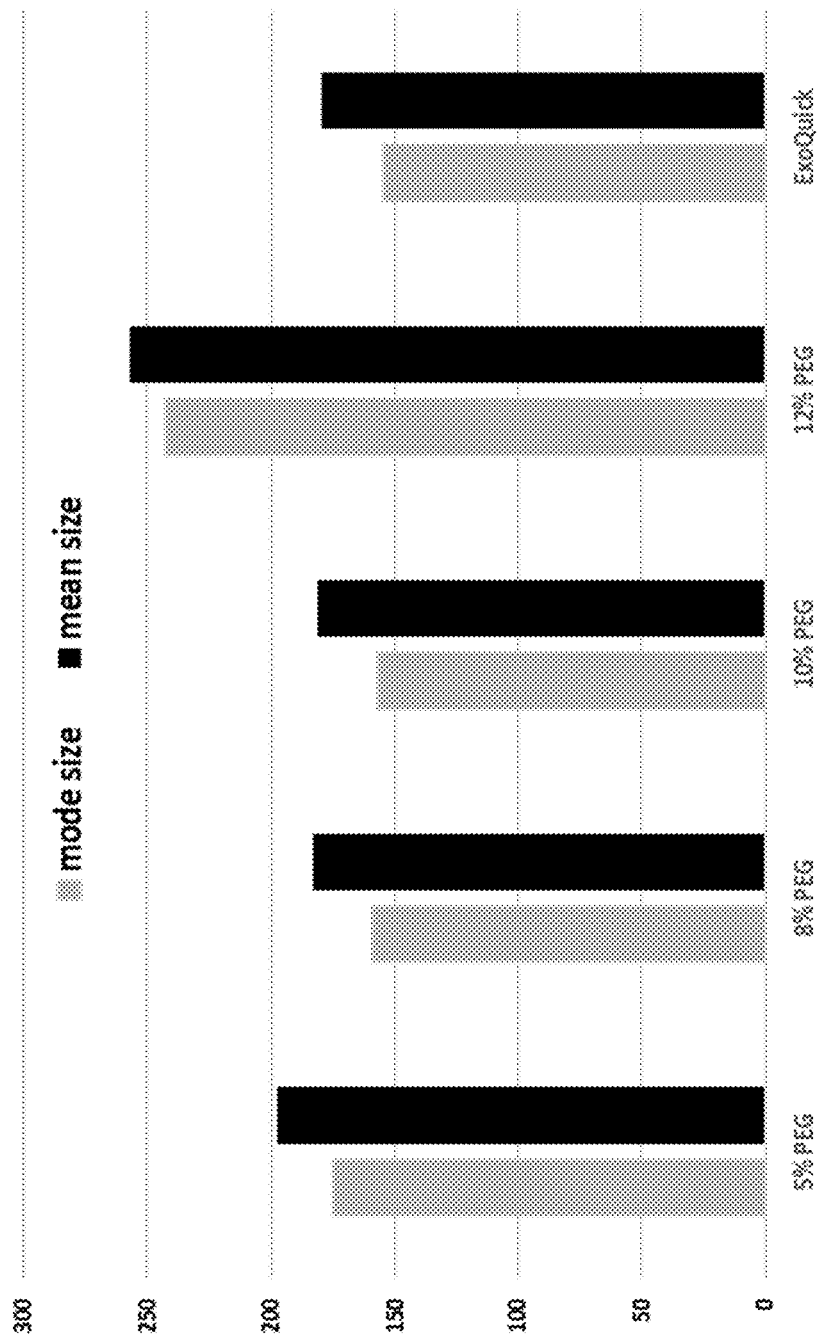
FIGS. 6K-6L illustrate the particles sizes of the exosomes described in FIGS. 6F-J.
Figure 6L:
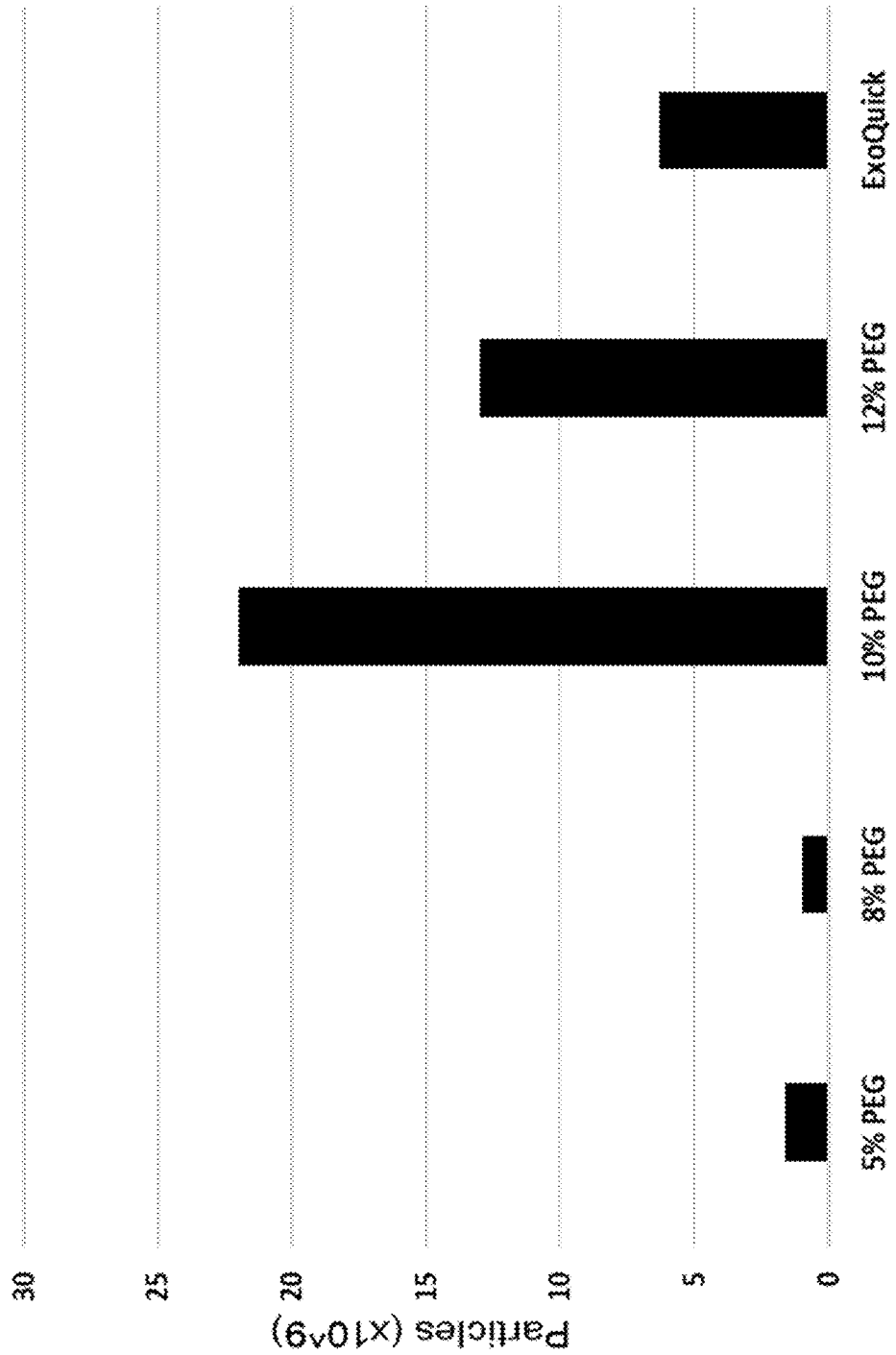

A proof of concept study was carried out which demonstrated the ability of the cells (e.g. T-REx-CD24 clone) to grow in suspension, in a shaker incubator, without serum. The cells were grown to high density culture with Expi293™ medium as discussed above. The medium was replaced with Expi293™ medium supplemented with tetracycline for 72 hours. Then exosomes were collected, purified and examined for size distribution (by NanoSight™)

and for CD24 expression (by FACS analysis, FIG. 6C) and EXO-ELISA™ (FIG. 6E). As evident from FIG. 6C, exosomes obtained from suspension cultures expressed CD24 and their size distribution was verified (FIG. 6D). Accordingly, exomes generated in high density suspension mediums are suitable for pharmaceutical use.

Isolation and Purification of Exosomes

The main component of the precipitation solution is PEG8000 which is present in the solution at a concentration of 15% weight/volume (i.e. 15 gr/100 mL). For the purpose of precipitation, one volume of the PEG solution (3 mL) is added to about 3 volumes (10 mL) of the exosome suspension for less than 5% (weight/volume). The precipitation is performed so that at the end of the process all the liquid is completely aspirated from the test tube and the exosome precipitate remains with a maximum amount of 50 microliters, so that it contains a maximum of 1.25 mg of PEG8000. It is assumed that after this process the PEG level decreases to about 0.1% of its initial level, i.e., 1.25 g or a concentration of 2.5 µg/mL. One dose per patient is at an equivalent volume of about 5 µL containing at most about 5 ng of PEG8000. The maximum permissible threshold level for respiratory exposure to PEG8000 is 5 mg/m³ according to US Occupational Safety and Health Administration (OSHA) permissible exposure limit (PEL). This amount translates to a level of about 30 µg for a full lung volume (about 6 L) while the present teachings relate to about a quantity that is 6,000 times lower for a full lung volume. In light of the above, there is no justification for examining residues of the precipitation solution.

Figure 6N:
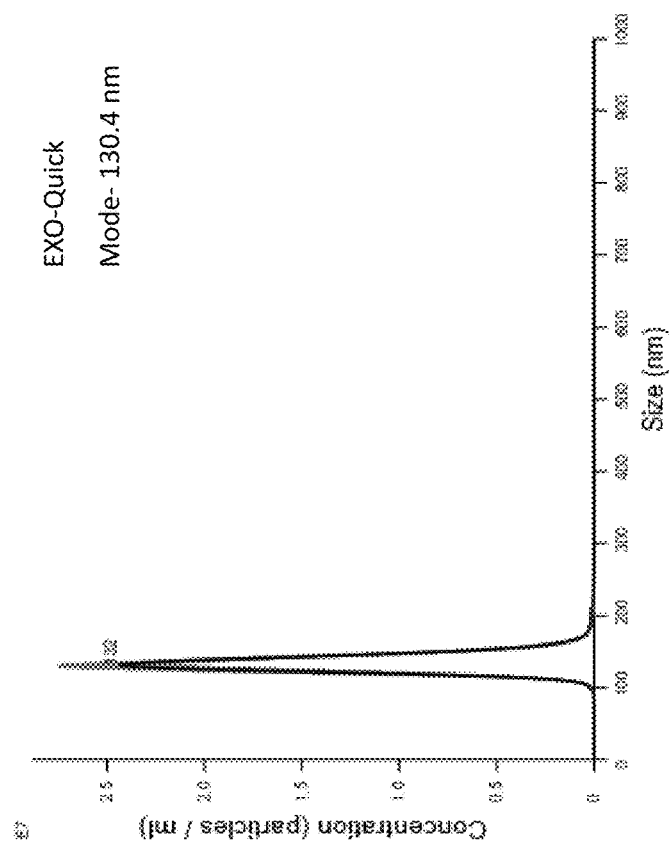
FIGS. 6M-6N illustrate the average sample concentration of the exosomes described in FIGS. 6F-J.
Figure 6M:
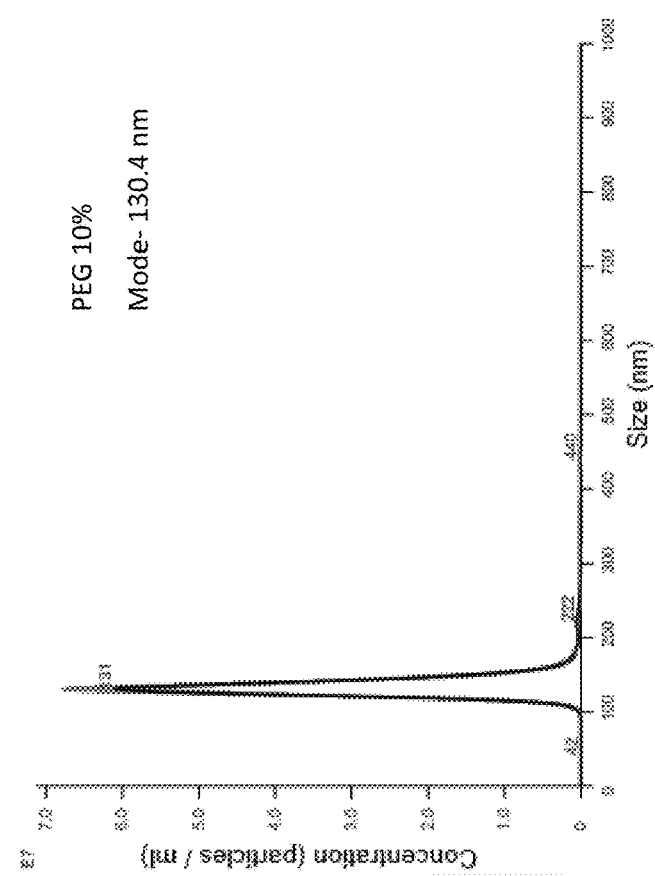

Easy-to-use commercial kits for harvesting exosomes are widely used, but the high-cost of the preparations restricts their utility. In addition, ultracentrifugation eliminates progressively smaller unwanted debris and larger subpopulations of vesicles. However, exosome isolation is complicated by the fact that vesicle subpopulations are not thoroughly defined and may overlap in size and density. Therefore, a method was developed to purify exosomes by adapting methods for isolating viruses using polyethylene glycol (PEG) to enrich exosomes from large volumes of media rapidly and inexpensively using low-speed centrifugation. Specifically, ExoQuick® and Total Exosome Isolation (TEI) reagents contain volume-excluding polymers (e.g.: PEG, dextrans or polyvinyls). However, simple solutions of PEG have been used for over fifty years to concentrate and purify viruses and bacteriophages. Because exosomes and virus particles have similar biophysical properties, it was hypothesized that a PEG-based method used for virus isolation could be modified to enrich and purify exosomes, providing an inexpensive and efficient alternative to commercially available products and ultracentrifugation. This method was evaluated by comparing it to the previously used method for isolation of EXO-CD24 (discussed above). As evident from FIGS. 6F-L, the use of 10% PEG provided the best results. Another experiment showed similar results when 10% PEG was compared to ExoQuick® by means of size distribution (FIGS. 6M-N). Regarding the purity, a secondary PEG treatment (with equal or lower percentage) is being examined for obtaining a purer population of particles and is compared to samples with PEG treatment alone or ExoQuick®. Accordingly, exomes isolated by ExoQuick® and PEG isolation methods are suitable for pharmaceutical use.

Examination of cell debris, HCP and HC DNA were irrelevant because the exosomes are membranal structures that display proteins on their surface and contain proteins, lipids, DNA and RNA. Therefore, a DNA presence test was performed. A sample containing approximately $2.3 \times 10^9$ exosomes per µL was tested using a NanoDrop™ microvolume spectrophotometer. The DNA reading indicated a concentration of 135.5 ng in a microliter. Thus, for the preparation of a treatment dose that includes $1 \times 10^8$, 0.04 µL should be taken from the sample. This means that 100 times dilution is performed and 4 microliters are taken into 3 ml (therefore 75000 times dilution), which leads to an estimate of 7.2 picograms per microliter, which is below the dictation threshold of the device (the detection range is 2-15,000 ng/µL). This is an amount lower than the standard accepted level with antibodies given intravenously (100 picograms per dose).

Example 3

Viral Testing Demonstrated Absence of Viruses

A series of viral tests (using PCR) was carried out for HIV-1/2, HBV, HCV. The upper fluid of the secreting cells was sampled during the preparation of Batch no. 3 and sent to the Clinical Virology Unit in Hadassah University Medical Center. Viral culture was performed in Vero and MRC-5 cells, with negative results. Positive controls showed rapid viral effect, whereas the collected sample remained negative (data not shown). All tests were found to be negative (Table 3, below). An additional series of viral tests was performed as follows:

TABLE 3

| Viral testing | |
|---|---|
| Virus | Test Result |
| Adeno Virus | Not detected |
| Herpes simplex type 1 | Not detected |
| Influenza A | Not detected |
| Herpes simplex type 2 | Not detected |
| Influenza B | Not detected |
| Varicella zoster | Not detected |
| Respiratory syncytial virus | Not detected |
| Human metapneumovirus | Not detected |
| Rhinovirus | Not detected |
| Parainfluenze | Not detected |

Example 4

GMP Production and Sterility Testing

The cells used for exosome secretion were HEK-293 cells (ATCC no. CRL-1573™). These progenitor human kidney cells originate from ATCC, which are known as free of endogenous viruses (as evident from the certificate of analysis provided by the ATCC). *Mycoplasma* and sterility and validation tests were performed for the secreting cells at the certified Hy Laboratories (hylabs) and illustrated no contamination (data not shown).

Example 5

Successful Audit of GMP Facility

An audit of the Accellta clean rooms was carried out. The audit was successful. It was found that the manufacturing process is in accordance with the GMP requirements and confirms with the associated SOPs (data not shown).

Example 6

Examination of CD24 Expression on Exosomes Secreted by the Engineered Cells

The expression of CD24 on the purified exosomal membranes was examined by ELISA and western blot analysis using an anti-CD24 monoclonal antibody. CD63 and/or HSP70 exosomal markers were used as positive controls. As can be seen in FIGS. 6A-B, in both ELISA and Western blot analysis, a high level of CD24 expression is detected following incubation of cells with tetracycline. The expression is exosomal, as the samples also express HSP70.

Example 7

Morphological Characterization of Exo-CD24 by Cryo-TEM

To investigate the morphological nature of the Exo-CD24 exosomal product produced from the CD24-expressing T-REx™-293 cells, the cryo-electron microscopy (EM) technique was employed (FIGS. 7A-B). This technique allows the visualization of the extracellular vesicles' size and morphology, with lipid bilayers and vesicular internal structures. Samples were prepared and applied onto an EM grid that was blotted and plunge frozen. This procedure results in embedding the samples in a thin layer of amorphous ice to preserve them in their native state and to protect from radiation damage. As evident from FIGS. 6A-B, the Exo-CD24 exosomal product express high levels of CD24.

Example 8

Stability of EXO-CD24

Figure 8:
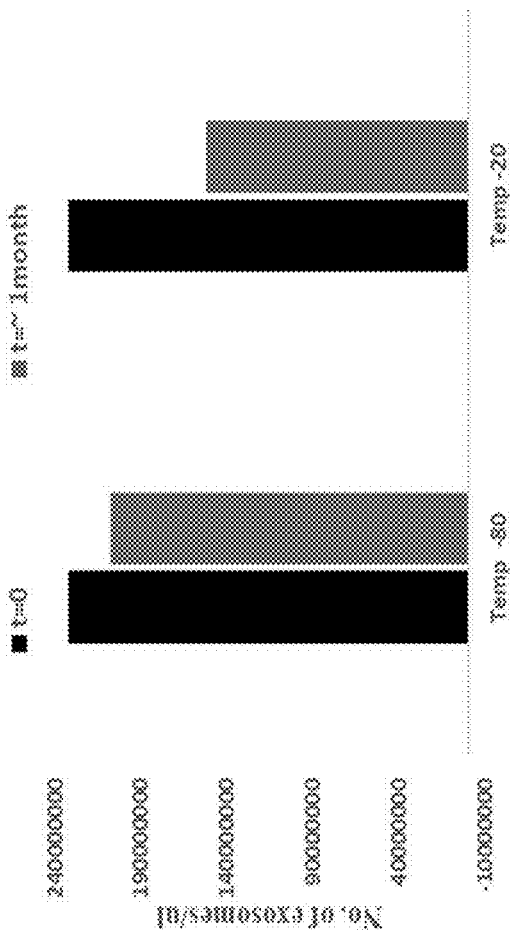
FIG. 8 illustrates a stability test. The purified exosomes were analyzed for CD63 using the ExoELISA-ULTRA™ assay kit at time t=O and about a month later. The concentration of the exosomes was determined according to a calibrated internal standard of exosomes carrying CD63.

To investigate the effect of storage temperature on exosome stability, exosomes derived from an engineering run were incubated at −20° C. and −80° C. for 1 month. A decrease of only about 10% in the stability of the exosomes stored at −80° C. was observed by NanoSight™. In summary, these results (FIG. 8), in line with previous reports in the literature, indicate that storage temperature influences recovery yield of the exosomes, and storage at −80° C. is the favorable condition for preservation of fresh exosomes for clinical application.

Example 9

Figures 9A, 9B:
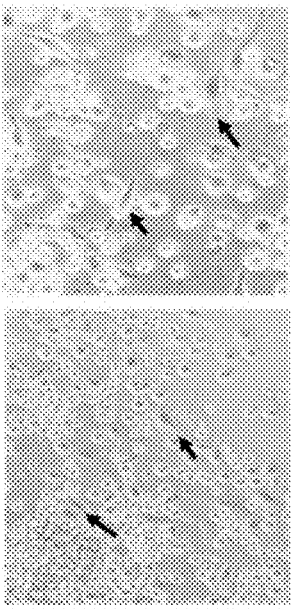
FIGS. 9A-9B illustrate the effect of PMA on differentiation of U937 monocytes to macrophage-like cells. Change in morphology and adherence of monocytes with PMA is presented. Microscopic pictures were taken of the untreated U937 cell (FIG. 9A) and 72-hours 100 ng/mL-treated macrophage-like cell (FIG. 9B). The arrows point to U937 differentiated cells.

EXO-CD24 Affects the Secretion of Pro-Inflammatory Cytokines in a Macrophage Cell Culture Model The effect of Exo-CD24 on the secretion of pro-inflammatory cytokines was studied in an in vitro model that makes use of the human macrophage (Mφ) cell line, U937. U937 cell differentiation was induced by exposure to PMA for 72 hours. Changes in cell morphology were used to assess the differentiation induced by PMA (FIGS. 9A-B). It was demonstrated that monocytes that were not exposed to PMA, grew in suspension showing their known morphological characteristics of small round shape cells (FIG. 9A), while PMA-exposed cells showed reduced proliferation rate (low confluence), different cell shapes and culture properties (adherent cells) (FIG. 9B). PMA inhibits the growth and causes U937 cells to differentiate by activating protein kinase C (PKC) leading to binding of AP1 and other transcriptional factors such as NF-κB (PMA mimics Diacylglycerol (DAG) which is a PKC activator). Exposure of cells to PMA induces adherence and cell cycle arrest followed by differentiation.

After 72 hours, 10 μg/ml hrHMGB1 and Exo-CD24 were added for 24 hours. Biofluids were collected and cytokine levels were examined using "Multi-plex array" (Human XL Cytokine Discovery Fixed Panel, AML). As expected, the expression levels of pro-inflammatory cytokines and chemokines, including MCP-1, MIP-3a, Fractalcine, G-CSF, IL-17E, IL-1α, IL-1β, IL-6, and RANTES were decreased (partially shown in FIGS. 10A-G). At the same time, the levels of other cytokines remained unchanged and some whose level even increased such as IL-4 and IL-7 (data not shown).

Example 10

Murine EXO-CD24 does not have Acute Toxic Effects

In order to examine the toxicity of Exo-CD24 in vivo, exosomes presenting the murine homolog of CD24 (HSA) were developed. For that purpose, high expression of HSA was transiently induced in Expi293F™ cells. These HSA/CD24-presenting exosomes were used to investigate the toxicity of the CD24 expressing exosomes.

A five-day repeated inhalation dose toxicity study in mice was carried out by Science in Action Ltd. Two doses, mid dose and high dose, were studied according to the following test groups:

TABLE 4

| | Test Groups | | |
|---|---|---|---|
| Group | Dosage (murine Exo-CD24/mouse) | Main Study (females) | Recovery (females) |
| Vehicle (saline) | control | 5 | 3 |
| Mid dose | $5 \times 10^8$ | 8 | 3 |
| High dose | $1 \times 10^9$ | 8 | 3 |

On the day of the experiment and after acclimatization, the animals were weighed and divided into the experimental groups described above. The animals received the inhalation treatment: the animals were placed into an inhalation cage (animal cage that is connected to an inhalation/immobilizer) and exposed to aerosol vapours containing the murine Exo-CD24 exosomal product for 20 minutes (the volume of material tested in the liquid—200 microliters per animal). The animals received the treatment every day for five days. They were monitored daily and weighed daily. On the 6th day, one day after the last treatment, eight animals from each group were sacrificed. The remaining three animals were monitored for another week. At the end of the experiment, under full anaesthesia, blood was taken from the heart for blood count and biochemistry. Then the animals were sacrificed with $CO_2$ and the organs mentioned above were taken for histochemical, histological, and pathological tests.

Figure 12:
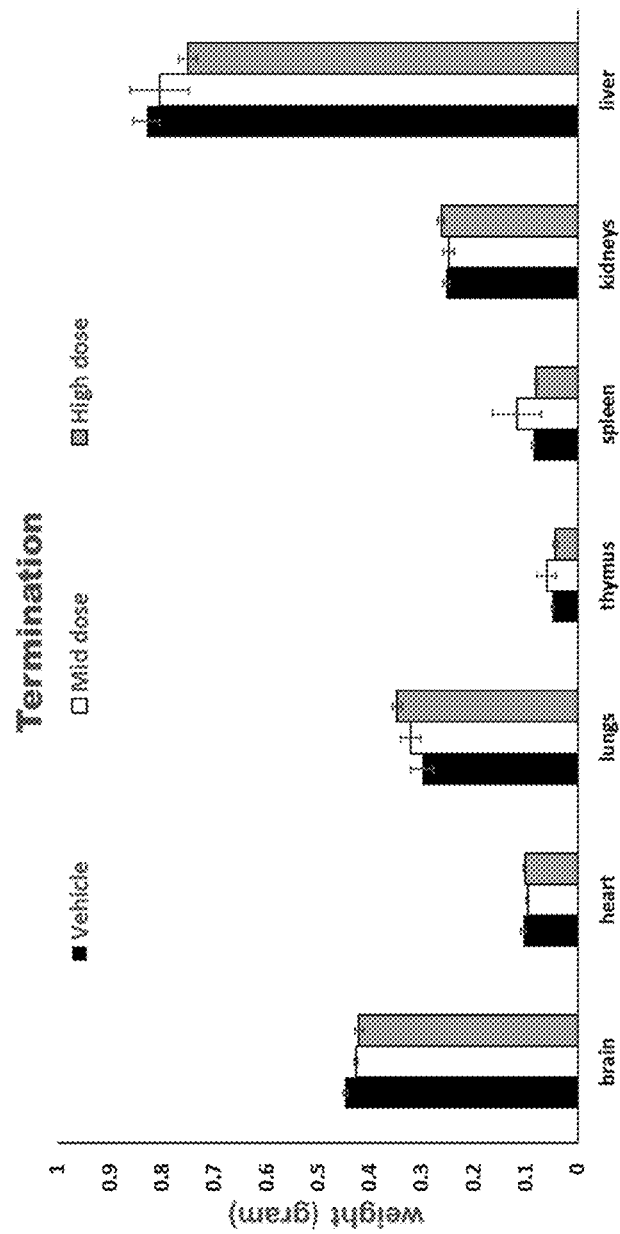
FIG. 12 illustrates animal organ weight at termination of a five-day repeated inhalation administration of murine Exo-CD24. Of note, no differences were observed.
Figure 14:
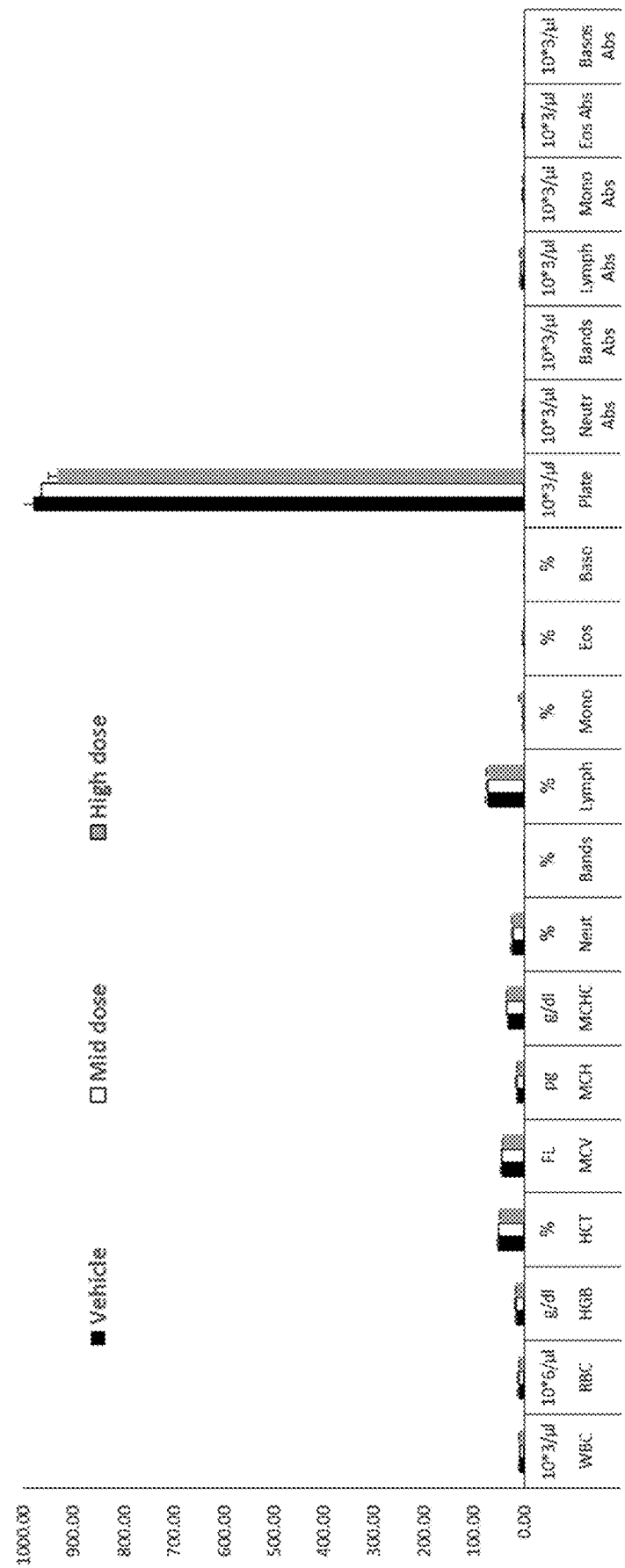
FIG. 14 illustrates animal hematology test markers at termination of a five-day repeated inhalation administration of murine Exo-CD24. Of note, no differences were observed
Figure 15:
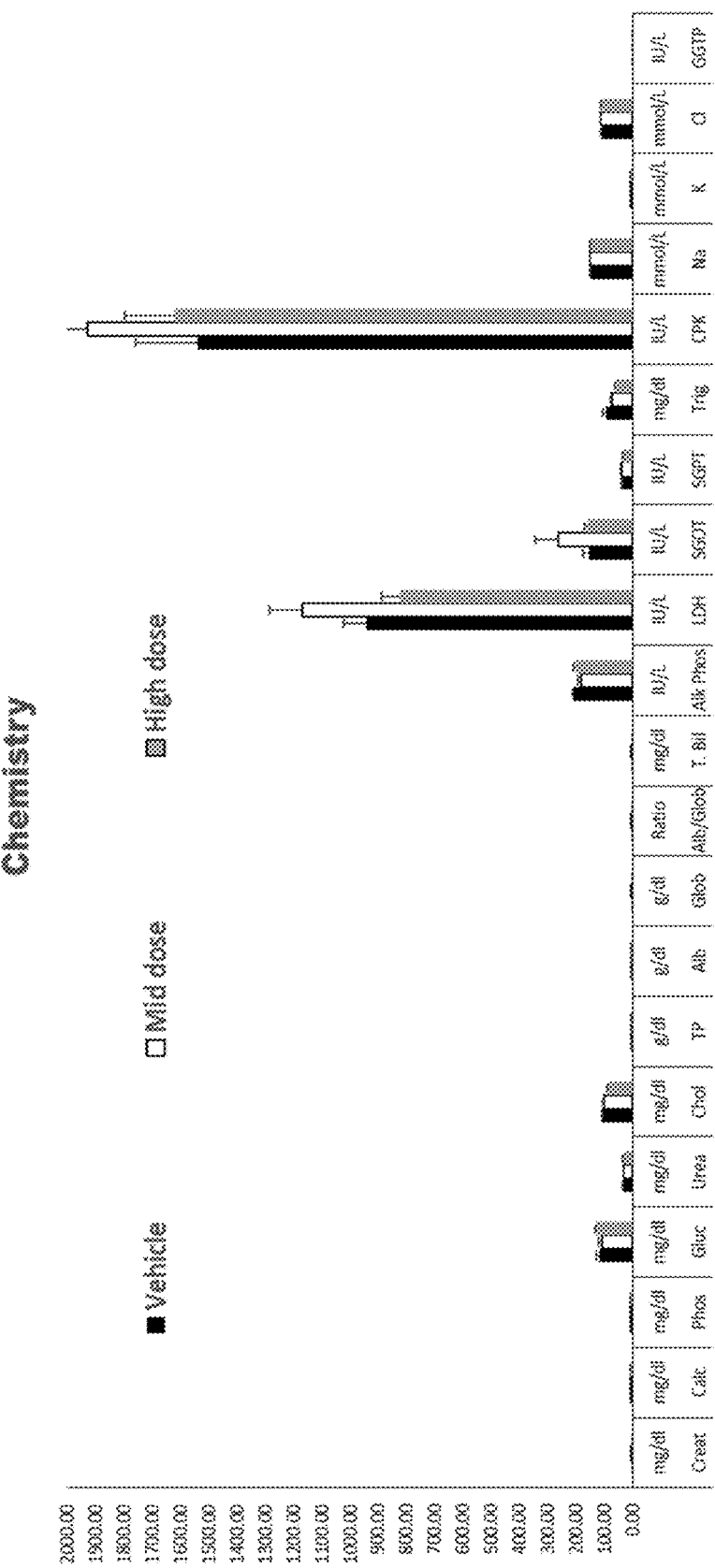
FIG. 15 illustrates animal chemistry test markers at termination of a five-day repeated inhalation administration of murine Exo-CD24. Of note, no differences were observed.

No clinical signs or adverse effects associated with the components of the investigational product (IP) were reported. No differences were observed in mouse weight (FIG. 11), organ weight at termination (FIG. 12), urine markers (FIG. 13), hematology markers (FIG. 14), and chemistry markers (FIG. 15).

Example 11

Murine EXO-CD24 Reduces Lung Damage In Vivo

Figure 16:
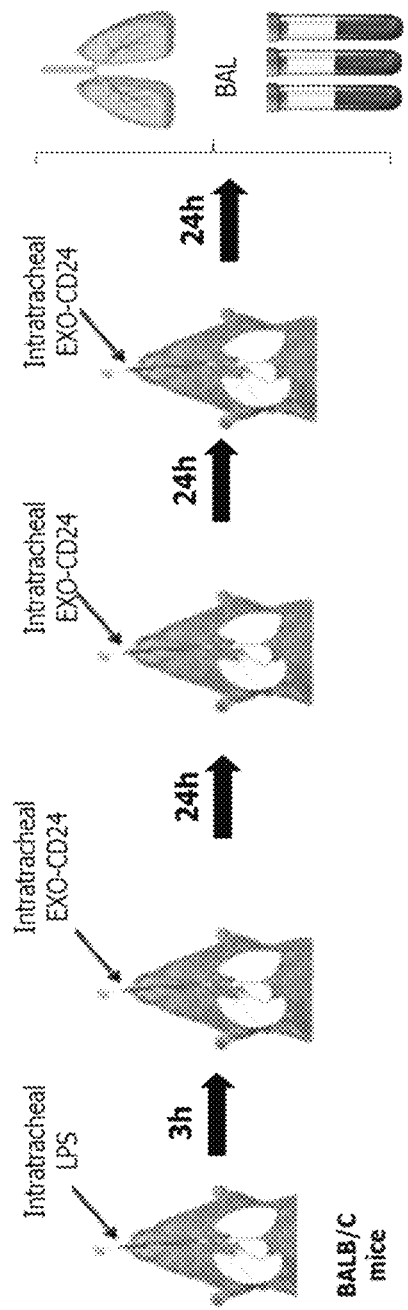
FIG. 16 illustrates the study design for in-vivo evaluation of murine Exo-CD24.
Figures 18A, 18B, 18C, 18D, 18E, 18F, 18G, 18H, 18I, 18J:
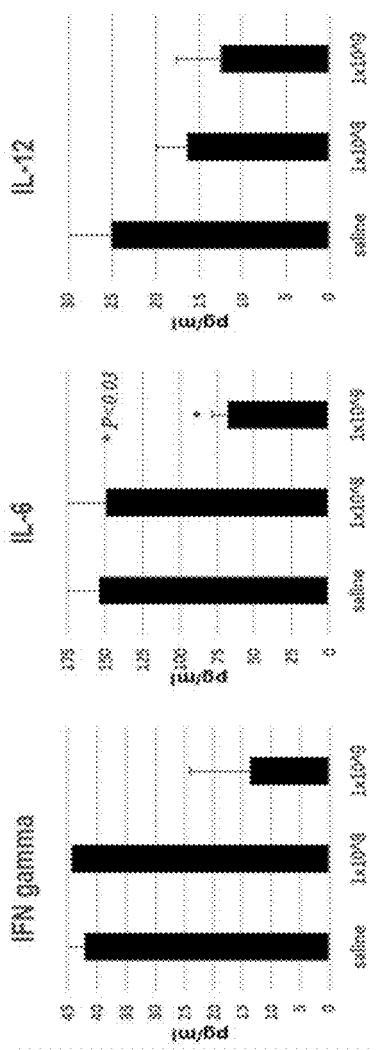
FIGS. 18A-18J illustrate representative cytokines/chemokines levels following in vivo treatment in an ARDS mouse model with murine Exo-CD24.

In order to examine the efficacy of Exo-CD24 in vivo, exosomes presenting the murine homolog of CD24 (HSA) were utilized. These HSA/CD24-presenting exosomes were used to investigate the efficacy of Exo-CD24 product in the acute respiratory distress syndrome (ARDS) model in mice by inhalation (FIG. 16). The study was a component of the development program of these exosomes for the treatment of patients with moderate COVID-19 infection to prevent their deterioration. The use of animals of the ARDS model enabled to test the efficacy of Exo-CD24 exosomes for the inhibition of clinical symptoms, which form the basis of the inflammatory response, and enable further development of this treatment for ARDS. The lipopolysacharide (LPS)-induced ARDS model is an accepted model for human acute respiratory disease caused by the SARS-Cov-2 infection.

The histology examination demonstrated that, in general, the lungs were affected. A multifocal to coalescing distribution of an inflammatory reaction was noticed, composed predominantly by neutrophils. The inflammatory infiltrates were mainly peri-vascular but were also observed around the mid-sized and small bronchioli. Group 3 (saline, FIG. 17A) showed a severe lung injury with a score of 4.7. Groups 1 (low dose of murine Exo-CD24, i.e. $1\times10^8$, FIG. 17B) showed a severe lung injury with a score of 4.6, and Group 2 (high dose of murine Exo-CD24 $1\times10^9$, FIG. 17C) showed an improvement in the inflammatory reaction with a score of 4.0 after only 72 hours (Table 5, below).

TABLE 5

Acute Lung Injury Severity Score (Mean ± SD)

| Group 1<br>Low dose murine<br>Exo-CD24 | Group 2<br>High dose murine<br>Exo-CD24 | Group 3<br>No treatment |
|---|---|---|
| 4.6 ± 0.84 | 4.0 ± 0.81 | 4.7 ± 1.11 |

One mouse in the control (saline) group died from LPS-induced disease, no deaths were recorded among the mice in the murine Exo-CD24 treatment groups.

Example 12

Murine EXO-CD24 Reduces Cytokine Levels In Vivo

Cytokine/Chemokine Multi-plex arrays testing was performed by a high sensitivity bead-based multiplex assay using the Luminex® technology. Cytokine and chemokine biomarkers were simultaneously analyzed with a high sensitivity bead-based multiplex assay using the Luminex® technology. An impressive reduction in cytokine and chemokine levels (IL-12, KC (keratinocytes-derived chemokine), IL-6, TNFα, IFN-gamma, IL-17) was observed in serum and Bronchial Alveolar Lavage (BAL) in a dose-depended manner (FIGS. 18A-J) following low dose or high dose of murine Exo-CD24 treatment described in Table 4, above. At the same time, IL-10 showed a certain increase in the BAL, and IL-13 in the serum (data not shown).

Example 13

Phase I Clinical Trial Results

Figure 19:
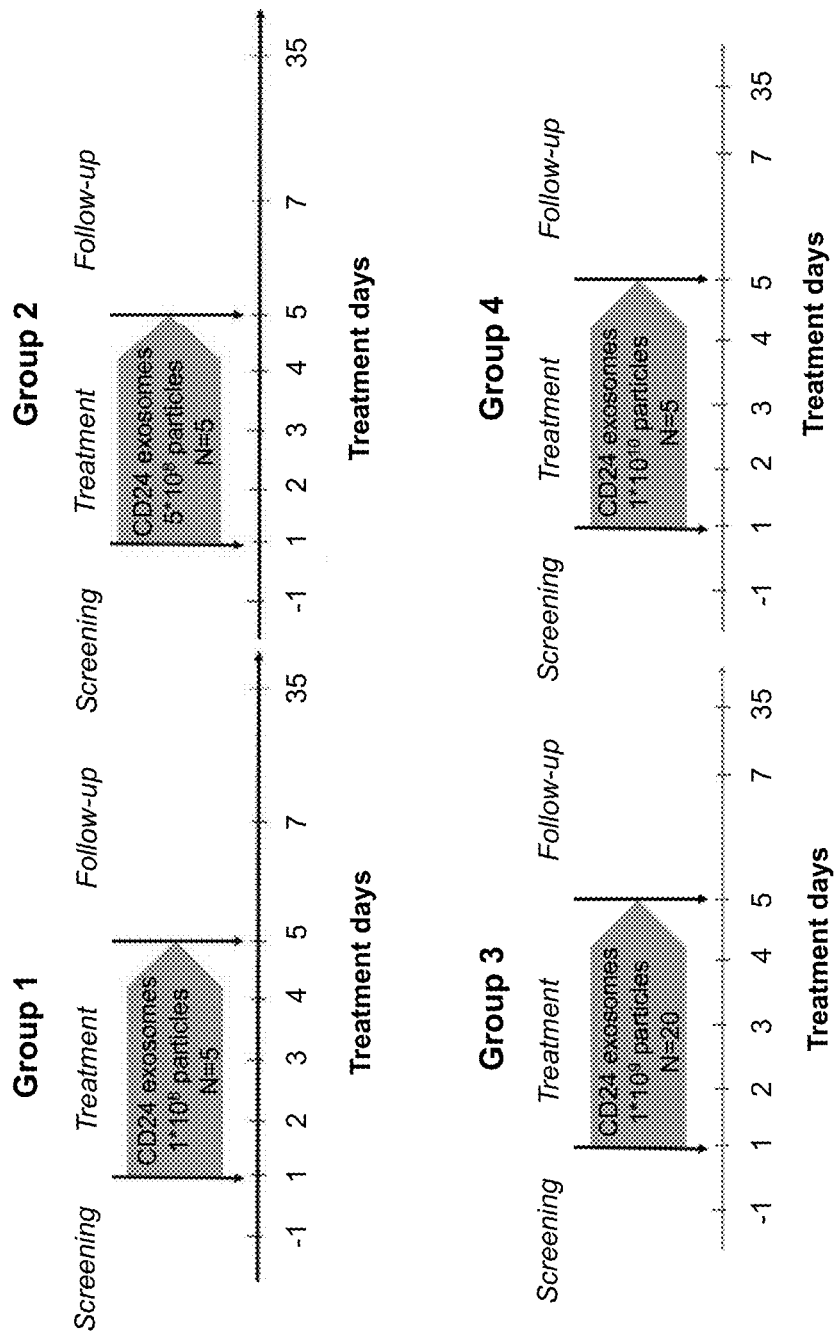
FIG. 19 illustrates the study diagram of a Phase 1, open-label clinical trial.

An overview of the treatment groups in the Phase I clinical trial is shown in FIG. 19.

Group 1: Five participants finished their participation in the First-in-Human Phase I trial. The results of the treatment of these patients (as presented in Table 6, below) illustrate that all five patients showed strong improvements following administration of Exo-CD24 exosomes at a concentration of $1\times10^8$ exosome particles per day for 5 consecutive days. No adverse events or serious adverse events were reported. Safety findings for each individual patient were reported to the Israel Ministry of Health. All five patients had a severe case of COVID-19 when they were hospitalized. Some of the patients' condition deteriorated during hospitalization, but within one or two days of treatment with Exo-CD24, they stabilized and subsequently their condition improved. Following treatment and a 30-day follow-up period following the end of treatment, all patients were fully cleared from the virus. Most of the patients returned to full function, whereas one of the patients has retained symptoms of a known pre-existing lung condition.

Chest X-rays confirmed a marked improvement in the patients' lungs, demonstrating a reduction in lung abnormalities and opacity. An example is shown in FIGS. 20A-B.

Group 2: The results of the next five participants are shown in Table 7, below. All five patients showed strong improvements following administration of Exo-CD24 exosomes at a concentration of $5\times10^8$ exosome particles per day for 5 consecutive days, without adverse events or serious adverse events. Safety findings for each individual patient were reported to the Israel Ministry of Health. All five patients had a severe case of COVID-19 when they were hospitalized. Some of the patients' condition deteriorated during hospitalization, but within one or two days of treatment with Exo-CD24, they stabilized and subsequently their condition improved. Following treatment and a 30-day follow-up period following the end of treatment, all patients were fully cleared from the virus, except patient 9. Most of the patients returned to full function.

Group 3: 20 participants finished their participation in which each subject was administered Exo-CD24 exosomes at a concentration of $1\times10^9$ exosome particles per day for 5 consecutive days. An overview of patient results in Group 3 is shown in Tables 8A-B, below.

TABLE 6

Results of Group 1 trial participants (Nos. 1-5)

| Patient identifier | 01-GOS-001 | 01-KAE-002 | 01-YTO-003 | 01-KOI-004 | 01-NAE-005 |
|---|---|---|---|---|---|
| Age (years) | 69 | 52 | 37 | 54 | 69 |
| Gender | Male | Male | Female | Male | Male |
| COVID-19 Severity | Severe | Severe | Severe | Severe | Severe |
| EXO-CD24 Dosage (exosomes/dose) | $1 \times 10^8$ | $1 \times 10^8$ | $1 \times 10^8$ | $1 \times 10^8$ | $1 \times 10^8$ |
| Diagnosis Date COVID-19 | 2 Sep. 2020 | 30 Sep. 2020 | 3 Nov. 2020 | 12 Nov. 2020 | 16 Nov. 2020 |
| Time from diagnosis to first treatment | 24 | 10 | 3 | 9 | 13 |

TABLE 6-continued

Results of Group 1 trial participants (Nos. 1-5)

| Patient identifier | 01-GOS-001 | 01-KAE-002 | 01-YTO-003 | 01-KOI-004 | 01-NAE-005 |
|---|---|---|---|---|---|
| COVID-19 standard of care treatments | Actmera ®, Eliquis ®, NEXIUM ®, Dexamethasone, Remdesivir, Clexane | Dexamethasone, Remdesivir, Clexane | Clexane, NEXIUM ® | Dexamethasone, Remdesivir, Clexane | Dexamethasone, Remdesivir, Clexane, TAVANIC |
| $SpO_2$ before treatment (%) | 90 | 91 | 94 | 90 | 90 |
| $SpO_2$ following treatment (%) | 97 | 97 | 98 | 96 | 97 |
| Respiratory rate before treatment (breaths/min) | 28 | 30 | 28 | 28 | 30 |
| Respiratory rate after treatment (breaths/min) | 18 | 18 | 20 | 14 | 16 |
| CRP level before treatment (mg/L) | 75.62 | 243.41 | 12.73 | 14.29 | 93.74 |
| CRP level following treatment (mg/L) | 14.42 | 0.53 | 26.63 | 1.97 | 8.80 |
| Adverse effect | none | none | none | none | none |
| Serious adverse effect | none | none | none | none | none |

TABLE 7

Results of Group 2 trial participants (Nos. 6-10)

| Patient identifier | 01-YAY-006 | 01-BAE-007 | 01-BEI-008 | 01-AYM-009 | 01-YAS-010 |
|---|---|---|---|---|---|
| Age (years) | 47 | 46 | 47 | 55 | 62 |
| Gender | Male | Male | Male | Female | Male |
| COVID-19 Severity | Severe | Severe | Severe | Severe | Severe |
| EXO-CD24 Dosage (exosomes/dose) | $5 \times 10^8$ | $5 \times 10^8$ | $5 \times 10^8$ | $5 \times 10^8$ | $5 \times 10^8$ |
| Diagnosis Date COVID-19 | 24 Nov. 2020 | 14 Dec. 2020 | 15 Dec. 2020 | 18 Dec. 2020 | 18 Dec. 2020 |
| Time from diagnosis to first treatment | 11 | 6 | 3 | 6 | 7 |
| COVID-19 standard of care treatments | Azithromycin, Acetylcysteine, Dexamethasone, Remdesivir, Clexane, Inhaler ICS. | Dexamethasone, Remdesivir, Clexane | Dexamethasone, Remdesivir, Clexane, PPI | Dexamethasone, Clexane | Dexamethasone, Azenil |
| $SpO_2$ before treatment (%) | 90 | 90 | 92 | 90 | 90 |
| $SpO_2$ following treatment (%) | 96 | 98 | 96 | 93 | 92 |
| Respiratory rate before treatment (breaths/min) | 30 | 28 | 30 | 29 | 30 |
| Respiratory rate after treatment (breaths/min) | 18 | 12 | 17 | 22 | 24 |
| CRP level before treatment (mg/L) | 120.65 | 115.65 | 148.32 | 136.48 | 109.00 |
| CRP level following treatment (mg/L) | 41.50 | 2.53 | 41.38 | 37.79 | 11.24 |
| Adverse effect | none | none | none | none | none |
| Serious adverse effect | none | none | none | none | none |

TABLE 8A

Results of Group 3 trial participants (Nos. 11-20)

| Patient identifier | 01-COY-011 | 01-ZIY-012 | 01-BEZ-013 | 01-BAH-014 | 01-HEE-015 | 01-MAY-016 | 01-ANV-017 | 01-ELG-018 | 01-ZEO-019 | 01-LIO-020 |
|---|---|---|---|---|---|---|---|---|---|---|
| Age (years) | 48 | 55 | 63 | 72 | 77 | 52 | 52 | 71 | 56 | 64 |
| Gender | Male | Male | Female | Male | Female | Male | Female | Male | Female | Male |
| COVID-19 Severity | Severe | Severe | Severe | Severe | Severe | Severe | Severe | Severe | Severe | Severe |
| EXO-CD24 Dosage (exosomes/dose) | $1 \times 10^9$ | $1 \times 10^9$ | $1 \times 10^9$ | $1 \times 10^9$ | $1 \times 10^9$ | $1 \times 10^9$ | $1 \times 10^9$ | $1 \times 10^9$ | $1 \times 10^9$ | $1 \times 10^9$ |
| Diagnosis Date COVID-19 | 23 Dec. 2020 | 23 Dec. 2020 | 22 Dec. 2020 | 29 Dec. 2020 | 21 Dec. 2020 | 3 Jan. 2021 | 28 Dec. 2020 | 10 Jan. 2021 | 10 Jan. 2021 | 28 Dec. 2020 |
| Time from diagnosis to first treatment | 10 | 14 | 18 | 12 | 19 | 9 | 16 | 3 | 3 | 19 |
| COVID-19 standard of care treatments | Dexamethasone, Remdesivir, Clexane, Rocephin ® | Dexamethasone, Remdesivir, Clexane, Sopa K | Dexamethasone, Remdesivir, Clexane | Dexamethasone, Clexane | Clexane | Dexamethasone, Clexane, Aerovent, Solvex | Dexamethasone, Nexium ® | Dexamethasone, Remdesivir, Nexium ® | Dexamethasone, Clexane | Clexane |
| SpO2 before treatment (%) | 90 | 90 | 90 | 91 | 90 | 90 | 91 | 91 | 90 | 90 |
| SpO2 following treatment (%) | 95 | 96 | 96 | 95 | 94 | 96 | 96 | 96 | 94 | 94 |
| Respiratory rate before treatment (breaths/min) | 30 | 30 | 30 | 30 | 30 | 30 | 28 | 28 | 30 | 30 |
| Respiratory rate after treatment (breaths/min) | 16 | 12 | 18 | 16 | 22 | 20 | 22 | 22 | 24 | 19 |
| CRP level before treatment (mg/L) | 210.76 | 239.80 | 6.14 | 89.20 | 237.33 | 40.60 | 48.64 | 100.90 | 200.00 | 180.08 |
| CRP level following treatment (mg/L) | 15.40 | 10.13 | 0.75 | 4.18 | 39.90 | 6.13 | 8.72 | 39.40 | 68.64 | 7.65 |
| Adverse effect | None | None | None | None | None | None | None | None | None | None |
| Serious adverse effect | None | None | None | None | None | None | None | None | None | None |

TABLE 8B

Results of Group 3 trial participants (#21-30)

| Patient identifier | 01-SHZ-021 | 01-HAY-022 | 01-ROT-023 | 01-FRK-024 | 01-GRM-025 | 01-SHR-026 | 01-ZER-027 | 01-COS-028 | 01-ABI-029 | 01-BAN-030 |
|---|---|---|---|---|---|---|---|---|---|---|
| Age (years) | 68 | 60 | 43 | 71 | 73 | 50 | 55 | 54 | 58 | 54 |
| Gender | Male | Male | Female | Female | Female | Male | Male | Female | Male | Male |
| COVID-19 Severity | Severe | Severe | Severe | Severe | Severe | Severe | Severe | Severe | Severe | Severe |
| EXO-CD24 Dosage (exosomes/dose) | $1 \times 10^9$ | $1 \times 10^9$ | $1 \times 10^9$ | $1 \times 10^9$ | $1 \times 10^9$ | $1 \times 10^9$ | $1 \times 10^9$ | $1 \times 10^9$ | $1 \times 10^9$ | $1 \times 10^9$ |
| Diagnosis Date COVID-19 | 7 Jan. 2021 | 15 Jan. 2021 | 17 Jan. 2021 | 19 Jan. 2021 | 17 Jan. 2021 | 13 Jan. 2021 | 17 Jan. 2021 | 11 Jan. 2021 | 14 Jan. 2021 | 20 Jan. 2021 |
| Time from diagnosis to first treatment | 10 | 6 | 2 | 2 | 5 | 9 | 6 | 13 | 13 | 7 |

TABLE 8B-continued

Results of Group 3 trial participants (#21-30)

| Patient identifier | 01-SHZ-021 | 01-HAY-022 | 01-ROT-023 | 01-FRK-024 | 01-GRM-025 | 01-SHR-026 | 01-ZER-027 | 01-COS-028 | 01-ABI-029 | 01-BAN-030 |
|---|---|---|---|---|---|---|---|---|---|---|
| COVID-19 standard of care treatments | | Dexamethasone, Nexium ® Remdesivir, Clexane, Plasma | Dexamethasone, Clexane, Remdesivir | Dexamethasone, Clexane | Dexamethasone, Clexane, Moxypen Forte ® | Nexium ®, Dexamethasone, Remdesivir, Clexane | Clexane | Dexamethasone, Remdesivir, Clexane | Actmera ®, Dexamethasone, Remdesivir | Nexium ®, Dexamethasone |
| SpO$_2$ before treatment (%) | 90 | 90 | | 91 | 90 | 92 | 92 | 90 | 93 | 93 |
| SpO$_2$ following treatment (%) | 94 | 95 | | 95 | 95 | 96 | 95 | 95 | 96 | 97 |
| Respiratory rate before treatment (breaths/min) | 30 | 27 | | 24 | 23 | 23 | 24 | 26 | 23 | 23 |
| Respiratory rate after treatment (breaths/min) | 20 | 12 | | 18 | 12 | 16 | 18 | 18 | 16 | 14 |
| CRP level before treatment (mg/L) | 141.43 | 85.62 | | 73.24 | 400.37 | 187 | 117.24 | 86.62 | 4.77 | 84.56 |
| CRP level following treatment (mg/L) | 155.79 | 4.22 | | 5.39 | 12.64 | 4.31 | 53.6 | 6.77 | 3.1 | 17.91 |
| Adverse effect | None | None | | None | None | None | None | None | None | None |
| Serious adverse effect | None | None | | None | None | None | None | None | None | None |

Group 4: 5 participants took part in this trial in which each subject was administered Exo-CD24 at a concentration of $1 \times 10^{10}$ exosome particles per day for 5 consecutive days. An overview of patient results in Group 3 is shown in Table 9, below.

TABLE 9

Results of Group 4 trial participants

| Patient no. | 031 | 032 | 033 | 034 | 035 |
|---|---|---|---|---|---|
| Age | 33 | 48 | 35 | 59 | 52 |
| Gender | Male | Female | Male | Female | Male |
| Severity | Severe | Moderate-Severe | Severe | Severe | Severe |
| Dosage | $1 \times 10^{10}$ | $1 \times 10^{10}$ | $1 \times 10^{10}$ | $1 \times 10^{10}$ | $1 \times 10^{10}$ |
| Diagnosis Date | 5 Feb. 2021 | 5 Feb. 2021 | 6 Feb. 2021 | 31 Jan. 2021 | 1 Feb. 2021 |
| Days from Diagnosis to treatment | 7 | 7 | 6 | 13 | 12 |
| COVID-19 Treatments* | Nexium ® Dexamethasone, Clexane | Dexamethasone, Clexane | Dexamethasone, Remdesivir, Clexane | Nexium ®, Dexamethasone, Clexane | Nexium ®, Dexamethasone, Clexane |
| SpO$_2$ before treatment | 90 | 92 | 90 | 90 | 90 |
| SpO$_2$ after treatment | 96 | 97 | 96 | 95 | 95 |
| Respiratory rate before treatment | 25 | 24 | 24 | 23 | 27 |
| Respiratory rate after treatment | 15 | 14 | 14 | 16 | 12 |

TABLE 9-continued

| Results of Group 4 trial participants | | | | | |
|---|---|---|---|---|---|
| Patient no. | 031 | 032 | 033 | 034 | 035 |
| CRP level before treatment | 16.07 | 43.52 | 37.53 | 154.66 | 98.18 |
| CRP level after treatment | 1.84 | 2.69 | 3 | 19.55 | 7.18 |
| Adverse effect | none | none | none | none | none |
| Serious adverse effect | none | none | none | none | none |

Figure 21:
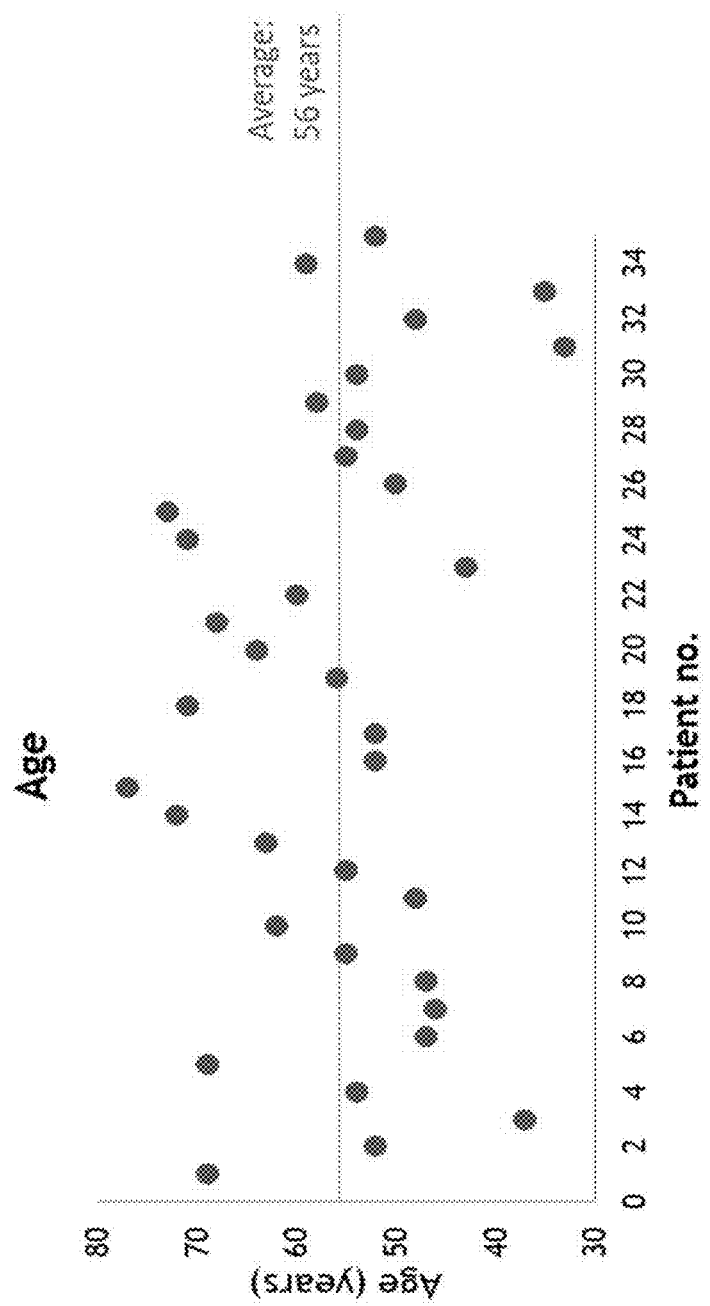
FIG. 21 illustrates the age of the Phase 1 clinical trial participants.
Figure 22:
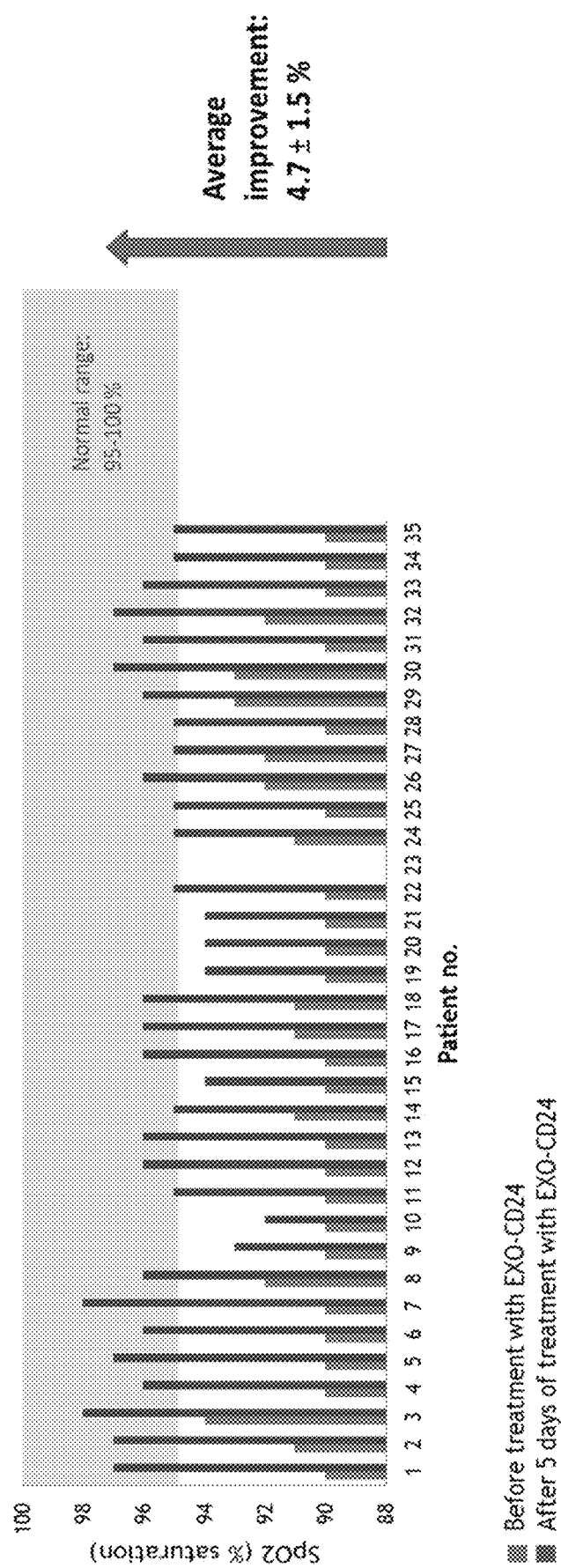
FIG. 22 illustrates an increase in blood saturation (SpO2) levels in 30 severe COVID-19 patients, before (light bars) and after (dark bars) treatment with Exo-CD24.
Figure 23:
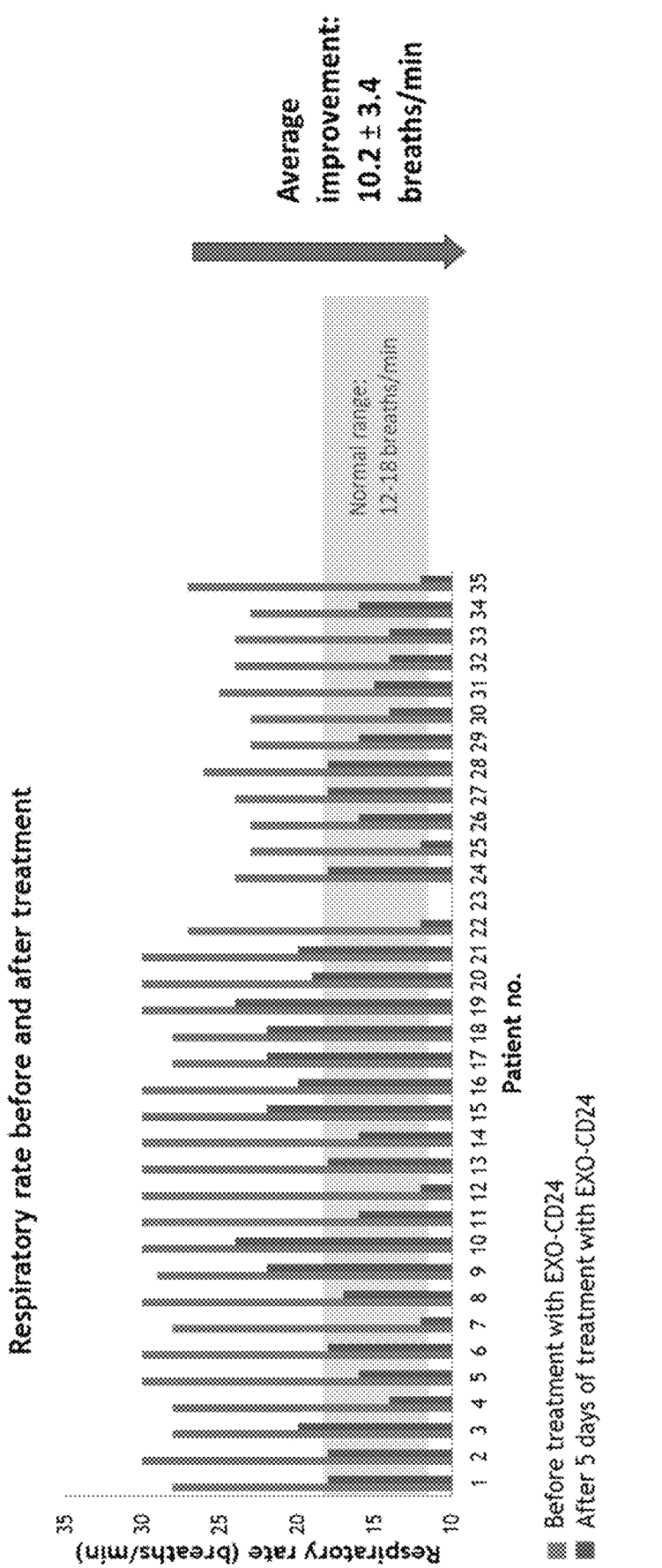
FIG. 23 illustrates a decrease in respiratory rate in 30 severe COVID-19 patients before (light bars) and after (dark bars) treatment with EXO-CD24.
Figure 24:
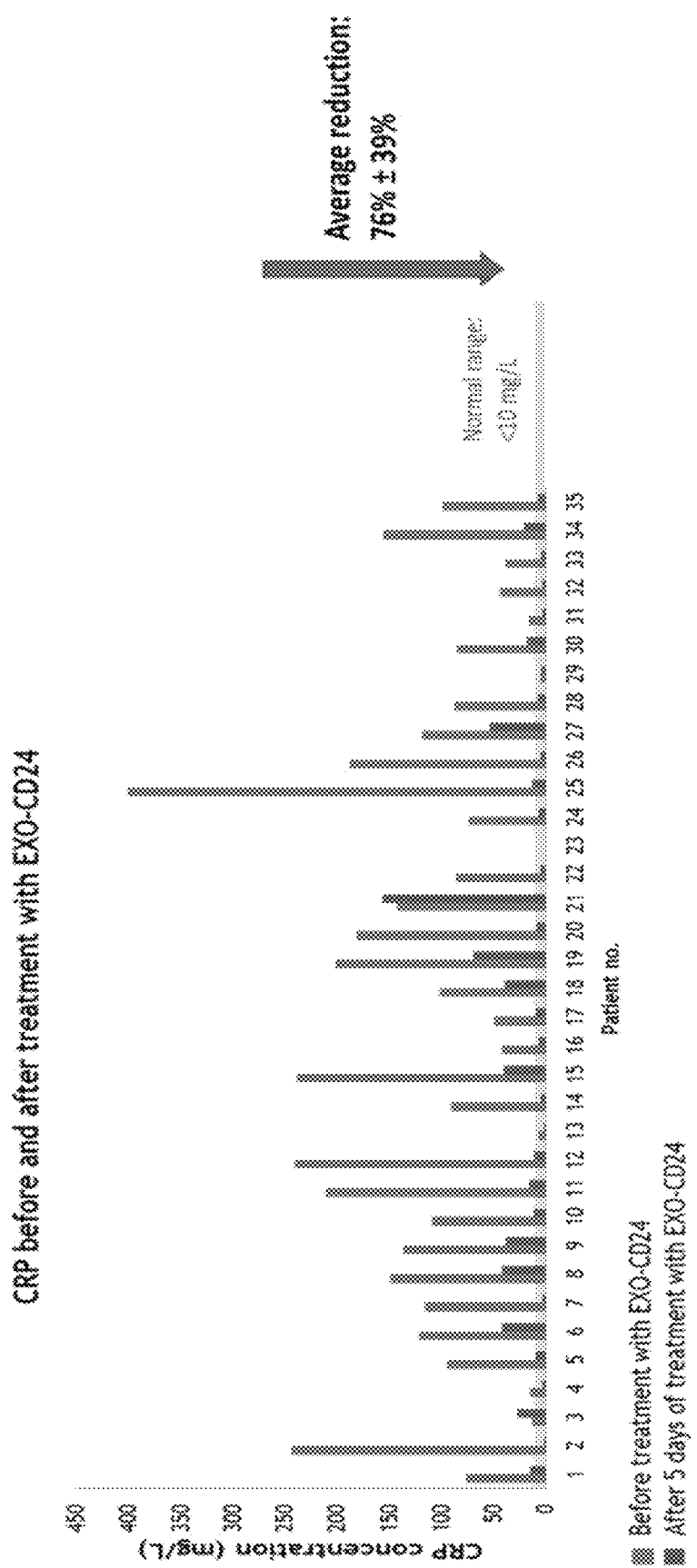
FIG. 24 illustrates a decrease in blood C-reactive protein level in 30 severe COVID-19 patients, before (light bars) and after (dark bars) treatment with EXO-CD24.

Summary of all 35 study participants: The average patient age was 56±10.1 years old (FIG. 21). 33% of the patients were female. No adverse effects were observed during the 7-day follow-up period, nor in the period leading up to the 35-day follow-up visit. The virus was not detected in any of the patients at the 35-day follow-up visit. On average, respiratory rate in the patients improved by 10.2±3.4 breaths/min, e.g. decreased from 27.4±2.8 breaths/min to 17.2±3.5 breaths/min (FIG. 23) and a dramatic improvement in inflammation indices was observed following treatment (CRP, IL-6, and pro-inflammatory cytokines and chemokines etc, data not shown). The average relative CRP level reduction was 76%±39% (FIG. 24) from 116.3±85.5% to 20.17±29.5%. Oxygen saturation increased by an average of 4.7.7±1.5%, e.g. from 90.7±1.1% to 95.6±1.3% (FIG. 22). Most of the patients returned to full function, whereas one of the patients has retained symptoms of a known pre-existing lung condition. Chest X-rays confirmed a marked improvement in the patients' lungs, demonstrating a reduction in lung abnormalities and opacity.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating a subject having a disease consisting of a coronavirus infection, the method comprising:
   (a) isolating exosomes from a biological sample comprising cells genetically modified to present CD24 so as to obtain a preparation of the exosomes substantially devoid of intact cells; and
   (b) administering to the subject via inhalation a therapeutically effective amount of the preparation of the exosomes,
   thereby treating the coronavirus infection in the subject.

2. The method of claim 1, further comprising genetically modifying cells to present CD24 to obtain said cells modified to present CD24 prior to said isolating exosomes from a biological sample.

3. The method of claim 2, further comprising culturing the cells modified to present CD24 prior to said isolating exosomes from a biological sample.

4. The method of claim 3, wherein the cells are cultured in a serum-free culture medium.

5. The method of claim 3, wherein the cells are cultured in a suspension culture in the absence of insulin and albumin or wherein the cells are cultured in a 2D culture comprising insulin and albumin.

6. The method of claim 1, wherein said CD24 is as set forth in SEQ ID NO: 9 or encodable by SEQ ID NO: 8.

7. The method of claim 1, wherein said exosomes have a mean particle diameter of about 80 to about 220 nm.

8. The method of claim 1, wherein said cells are cells of an animal or a human tissue.

9. The method of claim 1, wherein said cells am fibroblast cells or kidney cells.

10. The method of claim 1, wherein said cells are human embryonic kidney 293 cells (HEK-293) cells.

11. The method of claim 1, wherein said cells are human embryonic kidney 293 cells (HEK-293 cells) stably expressing the tetracycline repressor protein and genetically modified with a plasmid comprising CD24 gene cloned downstream to tetracycline-operator sequences and wherein said CD24 expression is inducible by tetracycline.

12. A method of treating a cytokine storm syndrome associated with acute respiratory distress syndrome (ARDS) in a subject in need thereof, the method comprising administering to the subject via inhalation a therapeutically effective amount of a composition comprising exosomes presenting heterologous CD24 on their surface, wherein said exosomes are obtained from cells genetically modified to present said CD24, and wherein the composition is substantially devoid of intact cells, thereby treating the cytokine storm syndrome in the subject.

13. The method of claim 1, wherein said coronavirus is severe acute respiratory syndrome coronavirus 2 (SARS-CoV-2).

14. The method of claim 5, wherein said coronavirus is severe acute respiratory syndrome coronavirus 2 (SARS-CoV-2).

* * * * *

```
                      SEQUENCE LISTING

Sequence total quantity: 9
SEQ ID NO: 1            moltype = DNA  length = 49
FEATURE                 Location/Qualifiers
misc_feature            1..49
                        note = Forward primer NheI-kozak-HAS
source                  1..49
                        mol_type = other DNA
                        organism = synthetic construct
SEQUENCE: 1
atatatgcta gcgctaccgg actcagatct gccatgggca gagcgatgg               49

SEQ ID NO: 2            moltype = DNA  length = 49
FEATURE                 Location/Qualifiers
misc_feature            1..49
                        note = Reverse primer HSA-EcoRI
source                  1..49
                        mol_type = other DNA
                        organism = synthetic construct
SEQUENCE: 2
atatatgaat tcgaagcttg agctcgtact aacagtagag atgtagaag               49

SEQ ID NO: 3            moltype = DNA  length = 1604
FEATURE                 Location/Qualifiers
misc_feature            1..1604
                        note = NA seq of CD24/HSA-IRES-GFP
source                  1..1604
                        mol_type = other DNA
                        organism = synthetic construct
SEQUENCE: 3
atgggcagag caatggtggc caggctcggg ctggggctgc tgctgctggc actgctccta    60
cccacgcaga tttattccag tgaaacaaca actgaactt  caagtaactc ctcccagagt   120
acttccaact ctgggttggc cccaaatcca actaatgcca ccaccaaggc ggctggtggt   180
```

```
gccctgcagt caacagccag tctcttcgtg gtctcactct ctcttctgca tctctactct    240
taatacgagc tcaagcttcg aattctgcag tcgacggtac cgcggggccc ggatccgccc    300
ctctccctcc ccccccccta acgttactgg ccgaagccgc ttggaataag ccggtgtgc    360
gtttgtctat atgttatttt ccaccatatt gccgtctttt ggcaatgtga gggcccggaa    420
acctggccct gtcttcttga cgagcattcc taggggtctt tcccctctcg ccaaaggaat    480
gcaaggtctg ttgaatgtcg tgaaggaagc agttcctctg gaagcttctt gaagacaaac    540
aacgtctgta gcgacccttt gcaggcagcg gaaccccca cctggcgaca ggtgcctctg    600
cggccaaaag ccacgtgtat aagatacacc tgcaaaggcg gcacaacccc agtgccacgt    660
tgtgagttgg atagttgtgg aaaagagtca aatggctctc tcaagcgtat tcaacaaggg    720
gctgaaggat gcccagaagg tacccccattg tatgggatct gatctgggc ctcggtgcac    780
atgctttaca tgtgtttagt cgaggttaaa aaaacgtcta ggccccccga accacgggga    840
cgtggttttc ctttgaaaaa cacgatgata atatggccac aaccatggtg agcaagggcg    900
aggagctgtt caccggggtg gtgcccatcc tggtcgagct ggacggcgac gtaaacggcc    960
acaagttcag cgtgtccggc gagggcgagg gcgatgccac ctacggcaag ctgaccctga   1020
agttcatctg caccaccggc aagctgcccg tgccctggcc caccctcgtg accaccctga   1080
cctacggcgt gcagtgcttc agccgctacc ccgaccacat gaagcagcac gacttcttca   1140
agtccgccat gcccgaaggc tacgtccagg agcgcaccat cttcttcaag gacgacggca   1200
actacaagac ccgcgccgag gtgaagttca agggcgacac cctggtgaac cgcatcgagc   1260
tgaagggcat cgacttcaag gaggacggca acatcctggg gcacaagctg gagtacaact   1320
acaacagcca caacgtctat atcatggccg acaagcagaa gaacggcatc aaggtgaact   1380
tcaagatccg ccacaacatc gaggacggca gcgtgcagct cgccgaccac taccagcaga   1440
acacccccat cggcgacggc cccgtgctgc tgcccgacaa ccactacctg agcacccagt   1500
ccgccctgag caaagacccc aacgagaagc gcgatcacat ggtcctgctg gagttcgtga   1560
ccgccgccgg gatcactctc ggcatggacg agctgtacaa gtaa                    1604

SEQ ID NO: 4          moltype = DNA  length = 243
FEATURE               Location/Qualifiers
misc_feature          1..243
                      note = NA seq of murine CD24
source                1..243
                      mol_type = other DNA
                      organism = synthetic construct
SEQUENCE: 4
atgggcagag caatggtggc caggctcggg ctggggctgc tgctgctggc actgctccta     60
cccacgcaga tttattccag tgaaacaaca actggaactt caagtaactc ctcccagagt    120
acttccaact ctgggttggc cccaaatcca actaatgcca ccaccaaggc ggctggtggt    180
gccctgcagt caacagccag tctcttcgtg gtctcactct ctcttctgca tctctactct    240
taa                                                                  243

SEQ ID NO: 5          moltype = AA  length = 319
FEATURE               Location/Qualifiers
REGION                1..319
                      note = AA seq of CD24/HSA-IRES-GFP
source                1..319
                      mol_type = protein
                      organism = synthetic construct
SEQUENCE: 5
MGRAMVARLG LGLLLLALLL PTQIYSSETT TGTSSNSSQS TSNSGLAPNP TNATTKAAGG     60
ALQSTASLFV VSLSLLHLYS MVSKGEELFT GVVPILVELD GDVNGHKFSV SGEGEGDATY    120
GKLTLKFICT TGKLPVPWPT LVTTLTYGVQ CFSRYPDHMK QHDFFKSAMP EGYVQERTIF    180
FKDDGNYKTR AEVKFEGDTL VNRIELKGID FKEDGNILGH KLEYNYNSHN VYIMADKQKN    240
GIKVNFKIRH NIEDGSVQLA DHYQQNTPIG DGPVLLPDNH YLSTQSALSK DPNEKRDHMV    300
LLEFVTAAGI TLGMDELYK                                                 319

SEQ ID NO: 6          moltype = AA  length = 80
FEATURE               Location/Qualifiers
REGION                1..80
                      note = AA seq of murine CD24
source                1..80
                      mol_type = protein
                      organism = synthetic construct
SEQUENCE: 6
MGRAMVARLG LGLLLLALLL PTQIYSSETT TGTSSNSSQS TSNSGLAPNP TNATTKAAGG     60
ALQSTASLFV VSLSLLHLYS                                                 80

SEQ ID NO: 7          moltype = DNA  length = 5254
FEATURE               Location/Qualifiers
misc_feature          1..5254
                      note = NA seq of pcDNA4/TO-CD24
source                1..5254
                      mol_type = other DNA
                      organism = synthetic construct
SEQUENCE: 7
acggatcggg agatctcccg atcccctatg gtgcactctc agtacaatct gctctgatgc     60
cgcatagtta agccagtatc tgctccctgc ttgtgtgttg gaggtcgctg agtagtgcgc    120
gagcaaaatt taagctacaa caaggcaagg cttaccgac aattgcatga agaatctgct    180
tagggttagg cgttttgcgc tgcttcgcga tgtacgggcc agatatacgc gttgacattg    240
attattgact agttattaat agtaatcaat tacgggtca ttagttcata gcccatatat    300
ggagttccg gttacataac ttacggtaaa tggcccgcct ggctgaccgc ccaacgaccc    360
```

```
ccgcccattg acgtcaataa tgacgtatgt tcccatagta acgccaatag ggactttcca   420
ttgacgtcaa tgggtggagt atttacggta aactgcccac ttggcagtac atcaagtgta   480
tcatatgcca agtacgcccc ctattgacgt caatgacggt aaatggcccg cctggcatta   540
tgcccagtac atgaccttat gggactttcc tacttggcag tacatctacg tattagtcat   600
cgctattacc atggtgatgc ggttttggca gtacatcaat gggcgtggat agcggtttga   660
ctcacgggga tttccaagtc tccaccccat tgacgtcaat gggagtttgt tttggaacca   720
aaatcaacgg gactttccaa aatgtcgtaa caactccgcc ccattgacgc aaatgggcgg   780
taggcgtgta cggtgggagg tctatataag cagagctctc cctatcagtg atagagatct   840
ccctatcagt gatagagatc gtcgacgagc tcgtttagtg aaccgtcaga tcgcctggag   900
acgccatcca cgctgttttg acctccatag aagacaccgg gaccgatcca gcctccggac   960
tctagcgttt aaacttaagc ttgcaccatg gcagagcaa tggtggccag gctcgggctg  1020
gggctgctgc tgctggcact gctcctaccc acgcagattt attccagtga acaacaact  1080
ggaacttcaa gtaactcctc ccagagtact tccaactctg ggttggcccc aaatccaact  1140
aatgccacca ccaaggcggc tggtggtgcc ctgcagtcaa cagccagtct cttcgtggtc  1200
tcactctctc ttctgcatct ctactcttaa tactctagag ggcccgttta aacccgctga  1260
tcagcctcga ctgtgccttc tagttgccag ccatctgttg tttgcccctc cccgtgcct   1320
tccttgaccc tggaaggtgc cactcccact gtccttcct aataaatga ggaaattgca   1380
tcgcattgtc tgagtaggtg tcattctatt ctggggggtg gggtgggca ggacagcaag   1440
ggggaggatt gggaagacaa tagcaggcat gctgggatg cggtgggctc tatggcttct   1500
gaggcggaaa gaaccagctg gggctctagg ggtatcccc acgcgcctg tagcggcgca   1560
ttaagcgcgg cgggtgtggt ggttacgcgc agcgtgaccg ctacacttgc cagcgcccta   1620
gcgcccgctc ctttcgcttt cttccttcc tttctcgcca cgttcgccgg ctttccccgt   1680
caagctctaa atcggggct ccctttaggg ttccgattta gtgctttacg gcacctcgac   1740
cccaaaaaac ttgattaggg tgatggttca cgtagtgggc catcgccctg atagacggtt   1800
tttcgccctt tgacgttgga gtccacgttc tttaatagtg gactcttgtt ccaaactgga   1860
acaacactca accctatctc ggtctattct tttgatttat aagggatttt gccgatttcg   1920
gcctattggt taaaaaatga gctgatttaa caaaaattta acgcgaatta attctgtgga   1980
atgtgtgtca gttagggtgt ggaaagtccc caggctcccc agcaggcaga agtatgcaaa   2040
gcatgcatct caattagtca gcaaccaggt gtggaaagtc cccaggctcc ccagcaggca   2100
gaagtatgca aagcatgcat ctcaattagt cagcaaccat agtcccgccc ctaactccgc   2160
ccatcccgcc cctaactccg cccagttccg cccattctcc gccccatggc tgactaattt   2220
ttttttattta tgcagaggcc gaggccgcct ctgcctctga gctattccag aagtagtgag   2280
gaggcttttt tggaggccta ggcttttgca aaaagctccc gggagcttgt atatccattt   2340
tcggatctga tcagcacgtg ttgacaatta atcatcggca tagtatatcg gcatagtata   2400
atacgacaag gtgaggaact aaaccatggc caagttgacc agtgccgttc cggtgctcac   2460
cgcgcgcgac gtcgccggag cggtcgagtt ctggaccgac cggctcgggt tctcccggga   2520
cttcgtggag gacgacttcg ccggtgtggt ccgggacgac gtgaccctgt tcatcagcgc   2580
ggtccaggac caggtggtgc cggacaacac cctggcctgg gtgtgggtgc gcggcctgga   2640
cgagctgtac gccgagtggt cggaggtcgt gtccacgaac ttccggacg cctccgggtca   2700
ggccatgacc gagatcggcg agcagccgtg ggggcgggag ttcgccctgc gcgaccggc   2760
cggcaactgc gtgcacttcg tggccgagga gcaggactga cacgtgctac gagatttcga   2820
ttccaccgcc gccttctatg aaaggttggg cttcggaatc gttttccggg acgccggctg   2880
gatgatcctc cagcgcgggg atctcatgct ggagtttctc gcccaccca acttgtttat   2940
tgcagcttat aatggttaca aataaagcaa tagcatcaca aatttcacaa ataaagcatt   3000
ttttttcactg cattctagtt gtggtttgtc aaaactcatc aatgtatctt atcatgtctg   3060
tataccgtcg acctctagct agagcttggc gtaatcatgg tcatagctgt ttcctgtgtg   3120
aaattgttat ccgctcacaa ttccacacaa catacgagcc ggaagcataa agtgtaaagc   3180
ctggggtgcc taatgagtga gctaactcac attaattgcg ttgcgctcac tgcccgcttt   3240
ccagtcggga aacctgtcgt gccagctgca ttaatgaatc ggccaacgcg cggggagagg   3300
cggtttgcgt attgggcgct cttccgcttc ctcgctcact gactcgctgc gctcggtcgt   3360
tcggctgcgg cgagcggtat cagctcactc aaaggcggta atacggttat ccacagaatc   3420
aggggataac gcaggaaaga acatgtgagc aaaaggccag caaaaggcca ggaaccgtaa   3480
aaaggccgcg ttgctggcgt ttttccatag gctccgcccc cctgacgagc atcacaaaaa   3540
tcgacgctca agtcagaggt ggcgaaaccc gacaggacta taaagatacc aggcgtttcc   3600
ccctggaagc tccctcgtgc gctctcctgt tccgaccctg ccgcttaccg gatacctgtc   3660
cgcctttctc ccttcgggaa gcgtggcgct ttctcatagc tcacgctgta ggtatctcag   3720
ttcggtgtag tcgttcgctc caagctgggc tgtgtgcac gaaccccccg ttcagcccga   3780
ccgctgcgcc ttatccggta actatcgtct tgagtccaac ccggtaagac acgacttatc   3840
gccactggca gcagccactg gtaacaggat tagcagagcg aggtatgtag gcggtgctac   3900
agagttcttg aagtggtggc ctaactacgg ctacactaga agaacagtat ttggtatctg   3960
cgctctgctg aagccagtta ccttcggaaa aagagttggt agctcttgat ccggcaaaca   4020
aaccaccgct ggtagcggtt ttttgtttg caagcagcag attacgcgca gaaaaaaagg   4080
atctcaagaa gatcctttga tcttttctac ggggtctgac gctcagtgga acgaaaactc   4140
acgttaagg atttggtca tgagattatc aaaaaggatc ttcacctaga tccttttaaa   4200
ttaaaaatga agttttaaat caatctaaag tatatatgag taaacttggt ctgacagtta   4260
ccaatgctta atcagtgagg cacctatctc agcgatctgt ctatttcgtt catccatagt   4320
tgcctgactc ccgtcgtgt agataactac gatacgggag ggcttaccat ctggccccag   4380
tgctgcaatg ataccgcgag acccacgctc accggctcca gatttatcag caataaacca   4440
gccagccgga agggccgagc gcagaagtgg tcctgcaact ttatccgcct ccatccagtc   4500
tattaattgt tgccgggaag ctagagtaag tagttcgcca gttaatagtt tgcgcaacgt   4560
tgttgccatt gctacaggca tcgtggtgtc acgctcgtcg tttggtatgg cttcattcag   4620
ctccggttcc caacgatcaa ggcgagttac atgatccccc atgttgtgca aaaaagcggt   4680
tagctccttc ggtcctccga tcgttgtcag aagtaagttg gccgcagtgt tatcactcat   4740
ggttatggca gcactgcata attctcttac tgtcatgcca tccgtaagat gcttttctgt   4800
gactggtgag tactcaacca agtcattctg agaatagtgt atgcggcgac cgagttgctc   4860
ttgcccggcg tcaatacggg ataataccgc gccacatagc agaactttaa aagtgctcat   4920
cattggaaaa cgttcttcgg ggcgaaaact ctcaaggatc ttaccgctgt tgagatccag   4980
ttcgatgtaa cccactcgtg cacccaactg atcttcagca tcttttactt tcaccagcgt   5040
ttctgggtga gcaaaaacag gaaggcaaaa tgccgcaaaa aagggaataa gggcgacacg   5100
```

```
gaaatgttga atactcatac tcttcctttt tcaatattat tgaagcattt atcagggtta  5160
ttgtctcatg agcggataca tatttgaatg tatttagaaa aataaacaaa taggggttcc  5220
gcgcacattt ccccgaaaag tgccacctga cgtc                              5254

SEQ ID NO: 8            moltype = DNA  length = 243
FEATURE                 Location/Qualifiers
misc_feature            1..243
                        note = NA seq of human CD24
source                  1..243
                        mol_type = other DNA
                        organism = synthetic construct
SEQUENCE: 8
atgggcagag caatggtggc caggctcggg ctggggctgc tgctgctggc actgctccta  60
cccacgcaga tttattccag tgaaacaaca actggaactt caagtaactc ctcccagagt  120
acttccaact ctgggttggc cccaaatcca actaatgcca ccaccaaggc ggctggtggt  180
gccctgcagt caacagccag tctcttcgtg gtctcactct ctcttctgca tctctactct  240
taa                                                                243

SEQ ID NO: 9            moltype = AA  length = 80
FEATURE                 Location/Qualifiers
REGION                  1..80
                        note = AA seq of human CD24
source                  1..80
                        mol_type = protein
                        organism = synthetic construct
SEQUENCE: 9
MGRAMVARLG LGLLLLALLL PTQIYSSETT TGTSSNSSQS TSNSGLAPNP TNATTKAAGG   60
ALQSTASLFV VSLSLLHLYS                                               80
```